(12) United States Patent
Spiegelman et al.

(10) Patent No.: US 7,371,529 B2
(45) Date of Patent: May 13, 2008

(54) METHODS AND COMPOSITIONS FOR MODULATING GLUCONEOGENESIS USING PGC-1

(75) Inventors: Bruce M. Spiegelman, Waban, MA (US); Clifford Hyunsuk Yoon, Cambridge, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 169 days.

(21) Appl. No.: 11/031,450

(22) Filed: Jan. 6, 2005

(65) Prior Publication Data

US 2005/0234001 A1 Oct. 20, 2005

Related U.S. Application Data

(63) Continuation of application No. 10/066,443, filed on Feb. 5, 2002, now abandoned.

(60) Provisional application No. 60/266,765, filed on Feb. 5, 2001.

(51) Int. Cl.
*C12Q 1/68* (2006.01)
(52) U.S. Cl. ........................................................ 435/6
(58) Field of Classification Search ...................... 435/6
See application file for complete search history.

(56) References Cited

U.S. PATENT DOCUMENTS 6,166,192 A 12/2000 Spiegelman et al.

FOREIGN PATENT DOCUMENTS

| CA | 2290944 | 12/1998 |
|---|---|---|
| CA | 2353086 | 6/2000 |
| WO | WO 98/54220 | 12/1998 |
| WO | WO 00/32215 | 6/2000 |

OTHER PUBLICATIONS

Emilsson et al (Metabolism (2000) 49(12):1610-1615).*
Ayala et al., "Conservation of an Insulin Response Unit Between Mouse and Human Glucose-6-Phosphatase Catalytic Subunit Gene Promoters," Diabetes, 48:1885-1889 (1999).
Barthel et al., "Novel concepts in insulin regulation of hepatic gluconeogenesis," Am. J. Physiol. Endocrinol. Metab., 285:2685-692 (2003).
Boss, O. et al., Role of the $\beta_3$-adrenergic receptor and/or a putative $\beta_4$,-adrenergic receptor on the expression of uncoupling proteins and peroxisome proliferator-activated receptor-$\gamma$ coactivator-1. Biochem. Biophys. Res. Commun. Aug. 11, 1999; 261(3):870-6.
Crawford et al., "Nuclear Factor I Regulates Expression of the Gene for Phosphoenolpyruvate Carboxykinase (GTP)," J. Biol. Chem., 273(22):13387-13390 (1998).
DeFronzo, R.A., "Pathogenesis of type 2 diabetes: metabolic and molecular implications for identifying diabetes genes," Diabetes Rev. 5(3):177-269 (1997).

Gomez-Ambrosi J. et al., "Rapid in vivo PGC-1 mRNA upregulation in brown adipose tissue of Wistar rats by a $\beta_3$- adrenergic agonist and lack of effect of leptin," Mol. Coll. Endocrinol. May 15;176(1-2):85-90 (2001).
Hall, R.K. et al., "The orphan receptors COUP-TF and HNF-4 serve as accessory factors required for induction of phosphoeno/pyruvate carboxykinase gene transcription by glucocorticoids," Proc. Natl. Acad. Sci. U.S.A. 92(2):412-6 (1995).
Hanson, R.W. et al., "Regulation of phosphoenolpyruvate carboxykinase (GTP) gene expressio,". Annu. Rev. Biochem. 66:581-611 (1997).
Herzog et al., "Characterization of the human liver fructose-1,6-bisphosphatase gene promoter," Biochem. J., 351:385-392 (2000).
Hinz, W. et al., "Recombinant human uncoupling protein-3 increases thermogenesis in yeast cells," FEBS Lett. 448(1):57-61 (1999).
Kakuma et al., "Role of leptin in peroxisome proliferator-activated receptor gamma coactivator 1 expression," Endocrinology, 141(12):4576-82 (2000).
Knutti, D. et al., "A tissue-specific coactivator of steroid receptors, identified in a functional genetic screen," Mol. Cell. Biol. (7):2411-22 (2000).
Lehman, J.J. et al., "Peroxisome proliferator-activated receptor $\gamma$ coactivator-1 promotes cardiac mitochondrial biogenesis," J. Clin. Invest. 106(7):847-56 (2000).
Lowell, B.B. et al., "Towards a molecular understanding of adaptive thermogenesis," Nature. 404(6778):652-60 (2000).
Michael, M.D. et al., "Loss of insulin signaling in hepatocytes leads to severe insulin resistance and progressive hepatic dysfunction," Mol. Cell 6(1):87-97 (2000).
Mitchell, J. et al., "Integration of multiple signals through a complex hormone response unit in the phosphoenolpyruvate carboxykinase gene promoter," Mol. Endocrinol. 8(5):585-94 (1994).
Nordlie, R.C. et al., "Regulation of glucose production by the liver," Annu. Rev. Nutr. 19:379 406 (1999).
Olefsky, J.M., "Treatment of insulin resistance with peroxisome proliferator-activated receptor $\gamma$ agonists," J. Clin. Invest. 106(4):467-72 (2000).
Pilkis, S.J. et al., "Molecular physiology of th regulation of hepatic gluconeogenesis and glycolysis," Annu. Rev. Physiol. 54:885-909 (1992).
Puigserver, P. et al., "A cold-inducible coactivator of nuclear receptors linked to adaptive thermogenesis," Cell 92(6):829-39 (1998).
Puigserver, P. et al. "Activation of PPAR $\gamma$ coactivator-1 through transcription factor docking," Science 286(5443):1368-71 (1999).
Radziuk J., Hepatic glycogen in humans. II. Gluconeogenetic formation after oral and intravenous glucose, Am. J. Physiol. 257(2 Pt 1):E158-69 (1989).
Shulman, G.I. et al., "Quantitative comparison of pathways of hepatic glycogen repletion in fed and fasted humans," Am. J. Physiol. 259(3 Pt 1):E335-41 (1990).

(Continued)

*Primary Examiner*—Jeffrey Fredman
(74) *Attorney, Agent, or Firm*—Foley Hoag LLP

(57) ABSTRACT

The invention provides novel methods and compositions for modulating gluconeogenesis through modulation of PGC-1 activity or expression. Also provided are methods for identifying compounds that modulate gluconeogenesis through modulation of PGC-1 activity or expression, as well as methods for identifying compounds that modulate the interaction of PGC-1 with PGC-1 target molecules. Further provided are methods for treating disorders characterized by aberrant gluconeogenesis.

8 Claims, 13 Drawing Sheets

OTHER PUBLICATIONS

Spiegelman, B.M., "PPAR- γ: adipogenic regulator and thiazolidinedione receptor," Diabetes 47(4):507-14 (1998).

Tcherepanova I. et al., "Modulation of estrogen receptor-α transcriptional activity by the coactivator PGC-1," J. Biol. Chem. 275(21):16302-8 (2000).

Vega, R.B. et al., "The coactivator PGC-1 cooperates with peroxisome proliferator-activated receptor α in transcriptional control of nuclear genes encoding mitochondrial fatty acid oxidation enzymes," Mol. Cell. Biol. 20(5):1868-76 (2000).

Vidal-Puig, A. et al., "UCP3: an uncoupling protein homologue expressed preferentially and abundantly in skeletal muscle and brown adipose tissue," Biochem. Biophys. Res. Commun. 235(1):79-82 (1997).

Vidal-Puig, A. et al., "Metabolism. Controlling the glucose factory," Nature 413(6852):125-6 (2001).

Wiemsperger, N.F. et al., "The antihyperglycaemic effect of metformin: therapeutic and cellular mechanisms," Drugs 58 Suppl 1:31-9 (1999).

Wu, Z. et al., "Mechanisms controlling mitochondrial biogenesis and respiration through the thermogenic coactivator PGC-1," Cell. 98(1):115-24 (1999).

Yoon, J.C. et al., "Control of hepatic gluconeogenesis through the transcriptional coactivator PGC-1," Nature 413(6852):131-8 (2001).

Yu et al., "Impact of endotoxin on UCP homolog mRNA abundance, thermoregulation, and mitochondrial proton leak kinetics," Am. J. Physiol. Endocrinol. Metab., 279:E433-446 (Aug. 2000).

Zhang, C.-Y. et al. ,"Assessment of uncoupling activity of uncoupling protein 3 using a yeast heterologous expression system," FEBS Lett. 449(2-3):129-34 (1999).

* cited by examiner

METHODS AND COMPOSITIONS FOR MODULATING GLUCONEOGENESIS USING PGC-1

RELATED APPLICATIONS

This application in a continuation application of U.S. application Ser. No. 10/066,443, filed Feb. 5, 2002, now abandoned which claims the benefit of U.S. Provisional Application Ser. No. 60/266,765, filed Feb. 5, 2001, the entire contents of which are incorporated herein by this reference.

GOVERNMENT SUPPORT

Work described herein was supported under grant 5R01DK54477-03 awarded by the National Institutes of Health. The U.S. government may have certain rights in this invention.

BACKGROUND OF THE INVENTION

All mammalian cells use glucose as a major energy source; certain cell types such as neurons and blood cells being especially dependent on it. Therefore, homeostatic mechanisms are in place to maintain blood glucose levels within a narrow range, protecting the body against prolonged periods of fasting and against excessively high levels following the ingestion of a meal. These goals are met chiefly through the production of glucose by the liver and the peripheral uptake by tissues such as the skeletal muscle, fat, and the liver.

The liver can produce glucose by breaking down glycogen (glycogenolysis) and converting certain precursor molecules such as lactate, pyruvate, glycerol, and alanine, into glucose (gluconeogenesis). Glycogenolysis occurs on a more rapid time scale, beginning within two to three hours after a meal in humans, but gluconeogenesis assumes a much greater importance as the liver glycogen stores become depleted (Nordlie, R. C., and Foster, J. D. (1999) *Annu. Rev. Nutr.* 19:379-406; Pilkis, S. J. and Granner, D. K. (1992) *Annu. Rev. Physiol.* 54:885-909, and references therein). The activation of glycogenolysis is primarily mediated by glycogen phosphorylase, which is in turn regulated allosterically and by cAMP-dependent protein kinase. The rate of gluconeogenesis is controlled by the available supply of precursors, as well as the activities of the multiple enzymes in the pathway, such as phosphoenolpyruvate carboxykinase (PEPCK), fructose-1,6-bisphosphatase, and glucose-6-phosphatase. These enzymes are regulated allosterically by intracellular metabolites in some cases and also at the level of the enzyme amount by extracellular hormones. The transcriptional control of the PEPCK gene by hormones is a particularly well-studied example.

Hormones are the principal means by which the body regulates systemic carbohydrate metabolism, including the response of the liver to fasting and feeding. Following a meal, the rise in plasma glucose immediately leads to increased secretion of insulin by the pancreatic β-cells, which lowers glucose by stimulating peripheral glucose uptake and suppressing hepatic glucose production. In the fasted state, on the other hand, insulin secretion diminishes, glucagon secretion goes up, and the catecholamines and the glucocorticoids increase relative to insulin. The counter-regulatory hormones such as glucagon and catecholamines enhance hepatic glucose output by stimulating both gluconeogenesis and glycogenolysis. Glucocorticoids also increase gluconeogenesis (hence their name). A careful coordination of the effects of these hormones is critical for fine-tuning the level of hepatic glucose production and is therefore a requisite part of achieving systemic normoglycemia.

Diabetes mellitus is broadly classified into type 1 (also known as insulin-dependent or IDDM) and type 2 (also known as non-insulin dependent or NIDDM) diabetes. The former is caused by an absolute deficiency of insulin, usually due to an autoimmune process affecting the β-cells of the pancreas, while the latter is caused by a combination of genetic and environmental factors that result in insulin resistance and relative insulin deficiency. Type 2 diabetes accounts for approximately 80% of the diabetic population. Other types of diabetes, such as maturity onset diabetes of the young (MODY) due to specific genetic mutations, are occasionally placed together in a third category.

The metabolic disturbances that underlie type 2 diabetes include impaired insulin secretion by pancreatic β-cells, reduced insulin-stimulated glucose uptake by skeletal muscle and adipose tissue, and increased hepatic glucose production (DeFronzo, R. A. (1997) *Diabetes Rev.* 5(3):177-269, and references therein). It is generally, although not universally, believed that the peripheral insulin resistance precedes the β-cell defect, as insulin resistance and compensatory hyperinsulinemia can be detected for an extended period of time well before any occurrence of glucose intolerance. Ultimately, however, the β-cells are unable to keep up, leading to a deterioration of glucose homeostasis and overt diabetes. The major site of insulin resistance depends on nutritional state. In the fasted state, the liver is the main source of hyperglycemia. In the fed or insulin-stimulated state, on the other hand, both inefficient glucose uptake by muscle and fat and impaired suppression of hepatic glucose output (HGO) contribute to postprandial hyperglycemia. While the liver can produce glucose by either glycogenolysis or gluconeogenesis, approximately 90% of the increase in HGO above baseline is attributed to accelerated gluconeogenesis (DeFronzo (1997) supra).

While type 2 diabetes is widely recognized as a polygenic disease, useful insights have been obtained from targeted gene disruptions in animals, for example, those involving the insulin receptor (IR), insulin receptor substrates (IRS), the p85 regulatory subunit of PI 3-kinase, and the Glut4 transporter. The use of the Cre/loxP system has also allowed a genetic dissection at the tissue level. A tissue-specific inactivation of the IR gene in the pancreatic β-cell (BIRKO) has been shown to produce a defect in acute phase glucose-stimulated insulin secretion, similar to that seen in type 2 diabetes (Kulkarni, R. N. et al. (1999) *Cell* 96:329-339). The IR deficiency in muscle (MIRKO) showed alterations of fat metabolism associated with diabetes, but unexpectedly the whole-body glucose disposal did not change significantly, suggesting that other tissues may compensate (Bruning, J. C. et al. (1998) *Mol. Cell* 2:559-569). On the other hand, the liver-specific IR knockout (LIRKO) generated mice with severe insulin resistance, glucose intolerance, and a failure of insulin to suppress HGO (Michael, M. D. et al. (2000) *Mol. Cell* 6:87-97).

Not surprisingly, oral pharmacological agents currently available for treatment of type 2 diabetes target some of these affected tissues. Sulfonylureas and repaglinide act on the β-cells to stimulate insulin secretion, and the TZDs and metformin improve insulin sensitivity in peripheral tissues such as muscle and/or liver (DeFronzo, R. A. (1999) *Ann. Intern. Med.* 31:281-303). However, there exists a need for additional therapeutic options which target the other major parameter of systemic glucose homeostasis, hepatic glucose output.

SUMMARY OF THE INVENTION

The present invention is based on the discovery that PGC-1 can stimulate glucose production by activating multiple key enzymes of the gluconeogenic pathway. Accordingly, the present invention provides methods for modulating gluconeogenesis comprising contacting a cell (e.g., a hepatocyte such as a primary hepatocyte or a Fao hepatoma cell) with an agent that modulates PGC-1 expression or activity, such that gluconeogenesis is modulated. In one embodiment, PGC-1 expression or activity is increased, thereby increasing gluconeogenesis. In another embodiment, PGC-1 expression or activity is decreased, thereby decreasing gluconeogenesis. The methods of the present invention may be performed both in vitro and in vivo.

In one embodiment, the agent used to modulate PGC-1 expression or activity is a PGC-1 nucleic acid molecule. The human PGC-1 nucleic acid molecule comprising the nucleic acid sequence of SEQ ID NO:4 or the mouse PGC-1 nucleic acid molecule comprising the nucleic acid sequence of SEQ ID NO:1, may be used. In one embodiment, nucleotides 515-529 of SEQ ID NO:1 are deleted. In another embodiment, nucleotides 518-532 of SEQ ID NO:4 are deleted. In yet another embodiment, the PGC-1 nucleic acid molecule is an antisense PGC-1 nucleic acid molecule.

In another embodiment, the PGC-1 nucleic acid molecule encodes a dominant negative PGC-1 polypeptide. In one embodiment the dominant negative polypeptide has a mutated LXXLL motif, e.g., wherein at least one of the leucine residues of the LXXLL motif is substituted with another amino acid residue, for example alanine. In a preferred embodiment, the leucine residue at the fourth position of the LXXLL motif is substituted with alanine. In another embodiment, the LXXLL motif is deleted.

In another embodiment, the agent is a PGC-1 polypeptide. In one embodiment, the human PGC-1 polypeptide comprising a polypeptide sequence of SEQ ID NO:5 is used. In this embodiment, amino acid residues 144-148 of SEQ ID NO:5 may be deleted. In another embodiment, the mouse PGC-1 polypeptide comprising the polypeptide sequence of SEQ ID NO:2 is used. In yet another embodiment, amino acid residues 142-146 of SEQ ID NO:2 may be deleted. In another embodiment, the agent is a polypeptide that binds to PGC-1.

In another embodiment, the PGC-1 polypeptide is a dominant negative PGC-1 polypeptide. In one embodiment the dominant negative polypeptide has a mutated LXXLL motif, e.g., wherein at least one of the leucine residues of the LXXLL motif is substituted with another amino acid residue, for example alanine. In a preferred embodiment, the leucine residue at the fourth position of the LXXLL motif is substituted with alanine. In another embodiment, the LXXLL motif is deleted In another embodiment, the invention provides a method for identifying a compound capable of modulating gluconeogenesis comprising contacting a cell (e.g., a hepatocyte such a primary hepatocyte or a Fao hepatoma cell) with a compound and determining whether PGC-1 expression or activity is modulated. In one embodiment, the compound is a small molecule.

In yet another embodiment, the invention provides a method for identifying a compound (e.g., a small molecule) capable of treating a disorder characterized by aberrant gluconeogenesis (e.g., diabetes such as type 1 diabetes, type 2 diabetes, or maturity onset diabetes of the young; obesity; or a disorder characterized by underproduction of glucose) comprising assaying the ability of the compound to modulate the expression or activity of PGC-1 to thereby identify a compound capable of treating a disorder characterized by aberrant gluconeogenesis.

In one embodiment, the compound causes an increase in PGC-1 expression or activity. Such a compound may be useful in treating disorders characterized by underproduction of glucose, e.g., hepatic enzyme abnormalities leading to hypoglycemia. In another embodiment, the compound causes a decrease in PGC-1 expression or activity. Such a compound may be used to treat disorders characterized by overproduction of glucose, e.g., diabetes (e.g., type 1 diabetes, type 2 diabetes, or maturity onset diabetes of the young) or obesity.

It will be appreciated that PGC-1 expression or activity may be determined by methods known to those skilled in the art. For example, PGC-1 expression may be measured by Northern blotting. In addition, the expression or activity of the gluconeogenic enzymes (e.g., phosphoenolpyruvate carboxykinase, glucose-6-phosphatase, and/or fructose-1,6-bisphosphatase) may be determined (e.g., by Northern blotting or by measurement of expression or activity of a phosphoenolpyruvate carboxykinase, glucose-6-phosphatase, or fructose-1,6-bisphosphatase promoter/enhancer reporter gene). In another embodiment, glucose output from the cell is measured (e.g., by measuring glucose concentration in the culture medium using a calorimetric glucose assay kit).

In still another embodiment, the invention provides a method for identifying a compound which inhibits the interaction of the PGC-1 protein with a target molecule (e.g., HNF-4α, FKHR, or the phosphoenolpyruvate carboxykinase promoter) comprising contacting, in the presence of the compound, the PGC-1 protein and the target molecule under conditions which allow binding of the target molecule to the PGC-1 protein to form a complex, and detecting the formation of a complex of the PGC-1 protein and the target molecule in which the ability of the compound to inhibit interaction between the PGC-1 protein and the target molecule is indicated by a decrease in complex formation, as compared to the amount of complex formed in the absence of the compound.

In another embodiment, the invention provides a method for treating a subject (e.g., a human) having a disorder characterized by aberrant gluconeogenesis comprising administering to the subject an agent capable of modulating PGC-1 expression or activity, such that the disorder is treated. In one embodiment, PGC-1 expression or activity is increased, resulting in an increase in gluconeogenesis. Such a method would therefore be useful in treating a subject having a disorder characterized by underproduction of glucose, e.g., hepatic enzyme abnormalities leading to hypoglycemia. In another embodiment, PGC-1 expression or activity is decreased, resulting in a decrease in gluconeogenesis. Such a method would therefore be useful in treating a subject having a disorder characterized by overproduction of glucose, e.g., diabetes (e.g., type 1 diabetes, type 2 diabetes, or maturity onset diabetes of the young) or obesity.

In one embodiment, the agent is a PGC-1 nucleic acid molecule (e.g., a human PGC-1 nucleic acid molecule) comprising a nucleic acid sequence of SEQ ID NO:4. In one embodiment, nucleotides 515-529 of SEQ ID NO:1 are deleted. In another embodiment, nucleotides 518-532 of SEQ ID NO:4 are deleted.

In another embodiment, the PGC-1 nucleic acid molecule encodes a dominant negative PGC-1 polypeptide. In one embodiment the dominant negative polypeptide has a mutated LXXLL motif, e.g., wherein at least one of the leucine residues of the LXXLL motif is substituted with another amino acid residue, for example alanine. In a preferred embodiment, the leucine residue at the fourth position of the LXXLL motif is substituted with alanine. In another embodiment, the LXXLL motif is deleted. In another embodiment, the PGC-1 nucleic acid molecule is an antisense PGC-1 nucleic acid molecule.

The agent capable of modulating PGC-1 expression or activity may be a PGC-1 nucleic acid molecule. In such an embodiment, the nucleic acid molecule may be administered to the subject via a vector. In a preferred embodiment, the vector is an adenoviral vector.

BRIEF DESCRIPTION OF THE DRAWING

FIG. 12A depicts the results using wild type FKHR, the wild type G6 Pase promoter, and cells treated with cAMP/dexamethasone or cAMP/dexamethasone/insulin. FIG. 12B depicts the results using a constitutively active mutant of FKHR ("3A") and a mutant G6 Pase promoter in which the insulin response units have been mutated.

DETAILED DESCRIPTION OF THE INVENTION

Figure 1:
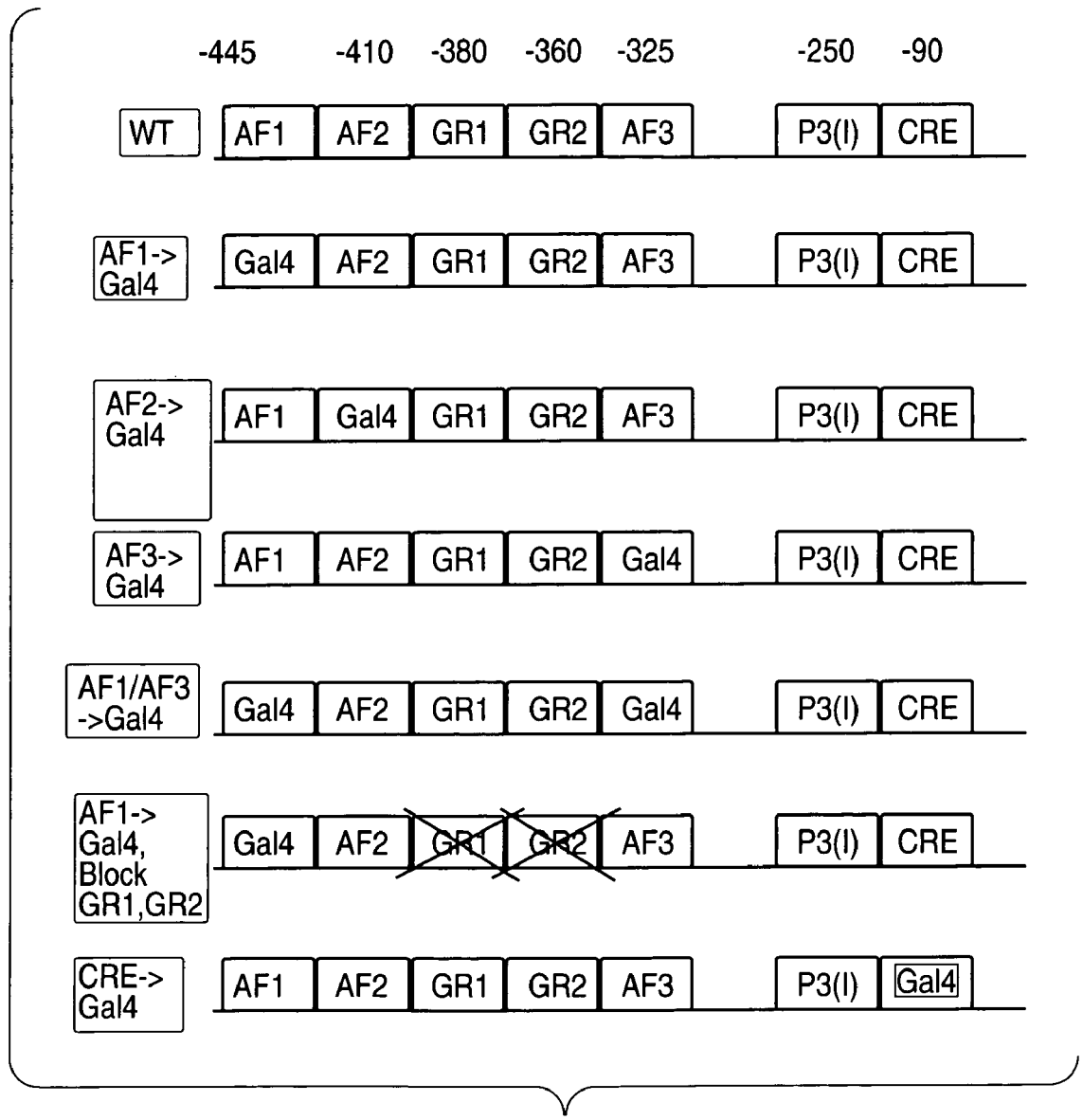
FIG. 1 depicts a schematic diagram of the −467 wild type phosphoenolpyruvate carboxykinase (PEPCK) promoter and the mutant promoters used in reporter assays. The arrows indicate a substitution of a particular element with the Gal4 DNA binding site. GR1 and GR2 mutations involved block mutations.

The present invention is based on the discovery that PGC-1 can stimulate glucose production in hepatocytes by activating multiple key enzymes of the gluconeogenic pathway. PGC-1 levels are induced in hepatocytes by cAMP and glucocorticoids, and its regulation in vivo coincides with hormonal changes that favor gluconeogenesis, e.g., as in fasting. These results indicate a regulatory role of PGC-1 in hepatic responses to fasting and implicate PGC-1 as a key hormone-regulated modulator of hepatic gluconeogenesis. The discovery further suggests that PGC-1 can direct distinct sets of target genes tailored to a particular tissue environment and physiology, making it a tightly controlled, yet versatile regulator, of different metabolic processes in multiple tissues.

PGC-1 is a recently described coactivator of nuclear receptors and has been shown to play a major role in cellular respiration and adaptive thermogenesis in tissues such as brown fat and skeletal muscle (Puigserver, P. et al. (1998) *Cell* 92:829-839; Wu, Z. et al. (1999) *Cell* 98:115-124). The discoveries of the instant invention implicate PGC-1 as a major regulator of gluconeogenesis.

More specifically, it has been found that expression of PGC-1 induces expression of the key gluconeogenic genes phosphoenolpyruvate carboxykinase (PEPCK), glucose-6-phosphatase, and fructose-1,6-bisphosphatese, causing increased glucose production in cells. PGC-1 also interacts directly with the PEPCK promoter and with HNF-4α and FKHR, key gluconeogenic transcription factors. Moreover, it has been found that the induction of these gluconeogenic genes and the resulting increase in glucose production, is dose specific.

The instant invention therefore provides methods and compositions for modulating gluconeogenesis using PGC-1 and modulators thereof. Accordingly, one aspect of the invention pertains to PGC-1 molecules, referred to herein as PGC-1 nucleic acid and protein molecules, which comprise a family of molecules having certain conserved structural and functional features, and which play a role in or function in gluconeogenesis associated activities. The term "family" when referring to the protein and nucleic acid molecules of the invention is intended to mean two or more proteins or nucleic acid molecules having a common structural domain and having sufficient amino acid or nucleotide sequence homology as defined herein. Such family members can be naturally occurring and can be from either the same or different species. For example, a family can contain a first protein of human origin, as well as other, distinct proteins of human origin or alternatively, can contain homologues of non-human origin. Members of a family may also have common functional characteristics.

Another aspect of the invention pertains to methods for treating a subject, e.g., a human, having a disease or disorder characterized by (or associated with) aberrant or abnormal PGC-1 nucleic acid expression and/or PGC-1 protein activity. These methods include the step of administering a PGC-1 modulator to the subject such that treatment occurs. The language "aberrant or abnormal PGC-1 expression" refers to expression of a non-wild-type PGC-1 protein or a non-wild-type level of expression of a PGC-1 protein. Aberrant or abnormal PGC-1 protein activity refers to a non-wild-type PGC-1 protein activity or a non-wild-type level of PGC-1 protein activity. As the PGC-1 protein is involved in, for example, a pathway involving gluconeogenesis, aberrant or abnormal PGC-1 protein activity or nucleic acid expression interferes with the normal glucose homeostasis functions. Non-limiting examples of disorders or diseases characterized by or associated with abnormal or aberrant PGC-1 protein activity or nucleic acid expression (also referred to as PGC-1 associated disorders) include diabetes, e.g., type 1 diabetes, type 2 diabetes, and maturity onset diabetes of the young (MODY); and disorders characterized by underproduction of glucose, e.g., hepatic enzyme abnormalities which result in hypoglycemia; and hypoglycemia, e.g., secondary hypoglycemia caused by other diseases, disorders, or conditions. PGC-1 associated disorders may also be any disorder or condition that is affected by abnormalities of glucose homeostasis, e.g., weight disorders such as obesity, cachexia, anorexia, and disorders associated with insufficient insulin activity. Disorders associated with body weight are disorders associated with abnormal body weight or abnormal control of body weight. As used herein, the language "diseases associated with or characterized by insufficient insulin activity" include disorders or diseases in which there is an abnormal utilization of glucose due to abnormal insulin function. Abnormal insulin function includes any abnormality or impairment in insulin production, e.g., expression and/or transport through cellular organelles, such as insulin deficiency resulting from, for example, loss of β cells as in IDDM (type 1 diabetes), secretion, such as impairment of insulin secretory responses as in NIDDM (type 2 diabetes), the form of the insulin molecule itself, e.g., primary, secondary or tertiary structure, effects of insulin on target cells, e.g., insulin-resistance in bodily tissues, e.g., peripheral tissues, and responses of target cells to insulin. See Braunwald, E. et al. eds. Harrison's Principles of Internal Medicine, Eleventh Edition (McGraw-Hill Book Company, New York, 1987) pp. 1778-1797; Robbins, S. L. et al. Pathologic Basis of Disease, 3rd Edition (W.B. Saunders Company, Philadelphia, 1984) p. 972 for further descriptions of abnormal insulin activity in IDDM and NIDDM and other forms of diabetes. The terms "treating" or "treatment", as used herein, refer to reduction or alleviation of at least one adverse effect or symptom of a disorder or disease, e.g., a disorder or disease characterized by or associated with abnormal or aberrant PGC-1 protein activity or PGC-1 nucleic acid expression.

As used herein, a PGC-1 modulator is a molecule which can modulate PGC-1 nucleic acid expression and/or PGC-1 protein activity. For example, a PGC-1 modulator can modulate, e.g., upregulate (activate) or downregulate (suppress), PGC-1 nucleic acid expression. In another example, a PGC-1 modulator can modulate (e.g., stimulate or inhibit) PGC-1 protein activity. If it is desirable to treat a disorder or disease characterized by (or associated with) aberrant or abnormal (non-wild-type) PGC-1 nucleic acid expression and/or PGC-1 protein activity by inhibiting PGC-1 nucleic acid expression, a PGC-1 modulator can be an antisense molecule, e.g., a ribozyme, as described herein. Examples of antisense molecules which can be used to inhibit PGC-1 nucleic acid expression include antisense molecules which are complementary to a portion of the 5' untranslated region of SEQ ID NO:1 or SEQ ID NO:4 which also includes the start codon and antisense molecules which are complementary to a portion of the 3' untranslated region of SEQ ID NO:1 or SEQ ID NO:4.

A PGC-1 modulator which inhibits PGC-1 nucleic acid expression can also be a small molecule or other drug, e.g., a small molecule or drug identified using the screening assays described herein, which inhibits PGC-1 nucleic acid expression. A PGC-1 molecule of the invention can thus also be used as a target to screen molecules, e.g., which can modulate PGC-1 activity.

If it is desirable to treat a disease or disorder characterized by (or associated with) aberrant or abnormal (non-wild-type) PGC-1 nucleic acid expression and/or PGC-1 protein activity by stimulating PGC-1 nucleic acid expression, a PGC-1 modulator can be, for example, a nucleic acid molecule encoding PGC-1 (e.g., a nucleic acid molecule comprising a nucleotide sequence homologous to the nucleotide sequence of SEQ ID NO:1 or SEQ ID NO:4) or a small molecule or other drug, e.g., a small molecule (peptide) or drug identified using the screening assays described herein, which stimulates PGC-1 nucleic acid expression.

Alternatively, if it is desirable to treat a disease or disorder characterized by (or associated with) aberrant or abnormal (non-wild-type) PGC-1 nucleic acid expression and/or PGC-1 protein activity by inhibiting PGC-1 protein activity, a PGC-1 modulator can be an anti-PGC-1 antibody or a small molecule or other drug, e.g., a small molecule or drug identified using the screening assays described herein, which inhibits PGC-1 protein activity. In a preferred embodiment, a PGC-1 modulator is a PGC-1 dominant negative, e.g., a PGC-1 polypeptide wherein the LXXLL motif is deleted or mutated, or a PGC-1 nucleic acid molecule which encodes a PGC-1 polypeptide wherein the LXXLL motif is deleted or mutated.

If it is desirable to treat a disease or disorder characterized by (or associated with) aberrant or abnormal (non-wild-type) PGC-1 nucleic acid expression and/or PGC-1 protein activity by stimulating PGC-1 protein activity, a PGC-1 modulator can be an active PGC-1 protein or portion thereof (e.g., a PGC-1 protein or portion thereof having an amino acid sequence which is homologous to the amino acid sequence of SEQ ID NO:2 or SEQ ID NO:5 or a portion thereof) or a small molecule or other drug, e.g., a small molecule or drug identified using the screening assays described herein, which stimulates PGC-1 protein activity.

In addition, a subject having a glucose homeostasis disorder, e.g., diabetes, can be treated according to the present invention by administering to the subject a PGC-1 protein or portion thereof or a nucleic acid encoding a PGC-1 protein or portion thereof such that treatment occurs. Similarly, a subject having a disorder associated with insufficient insulin activity can be treated according to the present invention by administering to the subject a PGC-1 protein or portion thereof or a nucleic acid encoding a PGC-1 protein or portion thereof such that treatment occurs.

Other aspects of the invention pertain to methods for modulating a cell associated activity. These methods include contacting the cell with an agent (or a composition which includes an effective amount of an agent) which modulates PGC-1 protein activity or PGC-1 nucleic acid expression such that a cell associated activity is altered relative to a cell associated activity of the cell in the absence of the agent. As used herein, "a cell associated activity" refers to a normal or abnormal activity or function of a cell. Examples of cell associated activities include proliferation, migration, differentiation, production or secretion of molecules, such as proteins, cell survival, and thermogenesis. In a preferred embodiment, the cell associated activity is gluconeogenesis and the cell is a hepatocyte. The term "altered" as used herein refers to a change, e.g., an increase or decrease, of a cell associated activity. In one embodiment, the agent stimulates PGC-1 protein activity or PGC-1 nucleic acid expression. Examples of such stimulatory agents include an active PGC-1 protein, a nucleic acid molecule encoding PGC-1 that has been introduced into the cell, and a modulatory agent which stimulates PGC-1 protein activity or PGC-1 nucleic acid expression and which is identified using the drug screening assays described herein. In another embodiment, the agent inhibits PGC-1 protein activity or PGC-1 nucleic acid expression. Examples of such inhibitory agents include a nucleic acid molecule encoding a dominant negative PGC-1 protein, a dominant negative PGC-1 protein, an antisense PGC-1 nucleic acid molecule, an anti-PGC-1 antibody, and a modulatory agent which inhibits PGC-1 protein activity or PGC-1 nucleic acid expression and which is identified using the drug screening assays described herein. These modulatory methods can be performed in vitro (e.g., by culturing the cell with the agent) or, alternatively, in vivo (e.g., by administering the agent to a subject). In a preferred embodiment, the modulatory methods are performed in vivo, i.e., the cell is present within a subject, e.g., a mammal, e.g., a human, and the subject has a disorder or disease characterized by or associated with abnormal or aberrant PGC-1 protein activity or PGC-1 nucleic acid expression.

A nucleic acid molecule, a protein, a PGC-1 modulator, a compound etc. used in the methods of treatment can be incorporated into an appropriate pharmaceutical composition described herein and administered to the subject through a route which allows the molecule, protein, modulator, or compound etc. to perform its intended function. Examples of routes of administration are also described herein.

The nucleotide sequence of the mouse PGC-1 cDNA and the predicted amino acid sequence of the mouse PGC-1 protein are shown in SEQ ID NOs:1 and 2, respectively. The nucleotide sequence of the human PGC-1 cDNA and the predicted amino acid sequence of the human PGC-1 protein are shown in SEQ ID NOs:4 and 5, respectively. The mouse PGC-1 gene, which is approximately 3066 nucleotides in length, encodes a full length protein having a molecular weight of approximately 120 kD and which is approximately 797 amino acid residues in length. The human PGC-1 gene, which is approximately 3023 nucleotides in length, encodes a full length protein having a molecular weight of approximately 120 kD and which is approximately 798 amino acid residues in length. PGC-1 family member proteins include several domains/motifs. These domains/motifs include: two putative tyrosine phosphorylation sites (amino acid residues 204-212 and 378-385 of SEQ ID NO:2, and amino acid residues 205-213 and 379-386 of SEQ ID NO:5), three putative cAMP phosphorylation sites (amino acid residues 238-241, 373-376, and 655-658 of SEQ ID NO:2, and 239-242, 374-377, and 656-658 of SEQ ID NO:5), a serine-arginine (SR) rich domain (amino acid residues 562-600 of SEQ ID NO:2, and 563-601 of SEQ ID NO:5), an RNA binding motif (amino acid residues 656-709 of SEQ ID NO:2, and 657-710 of SEQ ID NO:5), and an LXXLL motif (amino acids 142-146 of SEQ ID NO:2, 144-148 of SEQ ID NO:5; SEQ ID NO:3) which mediates interaction with HNF-4α and nuclear receptors. As used herein, a tyrosine phosphorylation site is an amino acid sequence which includes at least one tyrosine residue which can be phosphorylated by a tyrosine protein kinase. Typically, a tyrosine phosphorylation site is characterized by a lysine or an arginine about seven residues to the N-terminal side of the phosphorylated tyrosine. An acidic residue (asparagine or glutamine) is often found at either three or four residues to the N-terminal side of the tyrosine (Patschinsky, T. et al. (1982) *Proc. Natl. Acad. Sci. USA* 79:973-977); Hunter, T. (1982) *J. Biol. Chem.* 257:4843-4848; Cooper, J. A. et al. (1984) *J. Biol. Chem.* 259:7835-7841). As used herein, a "cAMP phosphorylation site" is an amino acid sequence which includes a serine or threonine residue which can be phosphorylated by a cAMP-dependent protein kinase. Typically, the cAMP phosphorylation site is characterized by at least two consecutive basic residues to the N-terminal side of the serine or threonine (Fremisco, J. R. et al. (1980) *J. Biol. Chem.* 255:4240-4245; Glass, D. B. and Smith, S. B. (1983) *J. Biol. Chem.* 258:14797-14803; Glass, D. B. et al. (1986) *J. Biol. Chem.* 261:2987-2993). As used herein, a "serine-arginine rich domain" or an "SR rich domain" is an amino acid sequence which is rich in serine and arginine residues. Typically, SR rich domains are domains which interact with the CTD domain of RNA polymerase II or are involved in splicing functions. As used herein, an "RNA binding motif" is an amino acid sequence which can bind an RNA molecule or a single stranded DNA molecule. RNA binding motifs are described in Lodish, H., Darnell, J., and Baltimore, D. *Molecular Cell Biology*, 3rd ed. (W.H. Freeman and Company, New York, N.Y., 1995). As used herein, an "LXXLL motif" (SEQ ID NO:3) refers to a motif wherein L represents leucine and X can be any amino acid, and which mediates an interaction between a nuclear receptor and a coactivator (Heery et al. (1997) *Nature* 397:733-736; Torchia et al. (1997) *Nature* 387:677-684).

The methods of the present invention also utilize the mouse and/or human HNF-4α molecules. The nucleotide and predicted polypeptide sequences of mouse HNF-4α are described in GenBank Accession Nos. NM_008261 and NP_032287, respectively. (further described in Hata, S. et al. (1995) *Biochim. Biophys. Acta.* 1260:55-61 and Nakhei, H. et al. (1998) *Nucleic Acids Res.* 26:497-504). The nucleotide and predicted polypeptide sequences of human HNF-4α are described in GenBank Accession Nos. NM_000457 and NP_000448, respectively (further described in Drewes, T. et al. (1996) *Mol. Cell. Biol.* 16:925-931; Winter, W. E. et al. (1999) *Endocrinol. Metab. Clin. North Am.* 28(4):765-785; Argyrokastritis, A. et al. (1997) *Hum. Genet.* 99:233-236; Yamagata, K. et al. (1996) *Nature* 384:458-460; Kritis, A. A. et al. (1996) *Gene* 173:275-280; Chartier, F. L. et al. (1994) *Gene* 147:269-272; and Bell, G. I. et al. (1991) *Proc. Natl. Acad. Sci. USA* 88:1484-1488).

The methods of the present invention still further utilize the mouse and/or human FKHR molecules. The nucleotide and predicted polypeptide sequences of mouse FKHR are described in GenBank Accession Nos. NM_019739 and NP_062713, respectively. (further described in Nakae, J. et al. (1999) *J. Biol. Chem.* 274:15982-15985 and Biggs, W. H. III et al. (2001) *Mamm. Genome* 12:416-425). The nucleotide and predicted polypeptide sequences of human FKHR are described in GenBank Accession Nos. NM_002015 and NP_002006, respectively (further described in Galili, N. et al. (1993) *Nat. Genet.* 5:230-235, with published erratum (1994) *Nat. Genet.* 6:214; Fredericks, W. J. et al. (1995) *Mol. Cell. Biol.* 15:1522-1535; Sublett, J. E. et al. (1995) *Oncogene* 11:545-552; Anderson, M. J. et al. (1998) *Genomics* 47:187-199; and Medema, R. H. et al. (2000) *Nature* 404: 782-787).

The methods of the present invention may therefore utilize PGC-1 protein or a biologically active portion or fragment, to: 1) modulate the expression of phosphoenolpyruvate carboxykinase (PEPCK), glucose-6-phosphatase, and/or fructose-1,6-bisphosphatase; 2) bind to and/or modulate the activity of the PEPCK promoter; 3) bind to and/or modulate the activity of HNF-4α; 4) bind to and/or modulate the activity of FKHR; 5) modulate glucose output from a cell; 6) modulate gluconeogenesis; 7) modulate glucose homeostasis; 8) treat diseases or disorders characterized by increased PGC-1 expression or activity, e.g., diabetes or obesity; and 9) treat diseases or disorders associated with decreased PGC-1 expression or activity, e.g., diseases or disorders characterized by underproduction of glucose.

Various aspects of the invention are described in further detail in the following subsections:

I. Isolated Nucleic Acid Molecules

One aspect of the invention pertains to methods utilizing isolated nucleic acid molecules that encode PGC-1 or biologically active portions thereof, as well as nucleic acid fragments sufficient for use as hybridization probes to identify PGC-1-encoding nucleic acid (e.g., PGC-1 mRNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated PGC-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a brown adipocyte). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of SEQ ID NO:1, SEQ ID NO:4 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1, SEQ ID NO:4 or a portion thereof (e.g., 400, 450, 500, or more nucleotides), can be isolated using standard molecular biology techniques and the sequence information provided herein. For example, a human PGC-1 cDNA can be isolated from a human liver, heart, kidney, or brain cell line (from Stratagene, LaJolla, Calif., or Clontech, Palo Alto, Calif.) using all or portion of SEQ ID NO:1 or SEQ ID NO:4 as a hybridization probe and standard hybridization techniques (e.g., as described in Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989). Moreover, a nucleic acid molecule encompassing all or a portion of SEQ ID NO:1 or SEQ ID NO:4 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1 or SEQ ID NO:4 can be isolated by the polymerase chain reaction using oligonucleotide primers designed based upon the sequence of SEQ ID NO:1 or SEQ ID NO:4 or the homologous nucleotide sequence. For example, mRNA can be isolated from liver cells, heart cells, kidney cells, brain cells, or brown adipocytes (e.g., by the guanidinium-thiocyanate extraction procedure of Chirgwin et al. (1979) *Biochemistry* 18: 5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO:1 or SEQ ID NO:4 or to the homologous nucleotide sequence. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a PGC-1 nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:1 or SEQ ID NO:4 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1 or SEQ ID NO:4. The sequence of SEQ ID NO:1 corresponds to the mouse PGC-1 cDNA. This cDNA comprises sequences encoding the PGC-1 protein (i.e., "the coding region", from nucleotides 92 to 2482), as well as 5' untranslated sequences (nucleotides 1 to 91) and 3' untranslated sequences (nucleotides 2483 to 3066). Alternatively, the nucleic acid molecule can comprise only the coding region of SEQ ID NO:1 (e.g., nucleotides 92 to 2482) or the homologous nucleotide sequence. The sequence of SEQ ID NO:4 corresponds to the human PGC-1 cDNA. This cDNA comprises sequences encoding the PGC-1 protein (i.e., "the coding region", from nucleotides 89 to 2482), as well as 5' untranslated sequences (nucleotides 1 to 88) and 3' untranslated sequences (nucleotides 2513 to 3023). Alternatively, the nucleic acid molecule can comprise only the coding region of SEQ ID NO:4 (e.g., nucleotides 89 to 2482) or the homologous nucleotide sequence.

In another preferred embodiment, an isolated nucleic acid molecule of the invention comprises a nucleic acid molecule which is a complement of the nucleotide sequence shown in SEQ ID NO:1 or SEQ ID NO:4 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1 or SEQ ID NO:4. A nucleic acid molecule which is complementary to the nucleotide sequence shown in SEQ ID NO:1 or SEQ ID NO:4 or to a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1 or SEQ ID NO:4 is one which is sufficiently complementary to the nucleotide sequence shown in SEQ ID NO:1 or SEQ ID NO:4 or to the homologous sequence such that it can hybridize to the nucleotide sequence shown in SEQ ID NO:1 or SEQ ID NO:4 or to the homologous sequence, thereby forming a stable duplex.

In still another preferred embodiment, an isolated nucleic acid molecule of the invention comprises a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1 or SEQ ID NO:4 or a portion of this nucleotide sequence. In an additional preferred embodiment, an isolated nucleic acid molecule of the invention comprises a nucleotide sequence which hybridizes, e.g., hybridizes under stringent conditions, to the nucleotide sequence shown in SEQ ID NO:1 or SEQ ID NO:4 or to a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1 or SEQ ID NO:4.

Moreover, the nucleic acid molecule of the invention can comprise only a portion of the coding region of SEQ ID NO:1 or SEQ ID NO:4 or the coding region of a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1 or SEQ ID NO:4, for example a fragment which can be used as a probe or primer or a fragment encoding a biologically active portion of PGC-1. The nucleotide sequence determined from the cloning of the PGC-1 gene from a mouse or human allows for the generation of probes and primers designed for use in identifying and/or cloning other PGC-1 family members, as well as PGC-1 homologues in other cell types, e.g. from other tissues, as well as PGC-1 homologues from other mammals such as rats or monkeys. The probe/primer typically comprises substantially purified oligonucleotide. The oligonucleotide typically comprises a region of nucleotide sequence that hybridizes under stringent conditions to at least about 12, preferably at least about 25, more preferably about 40, 50 or 75 consecutive nucleotides of SEQ ID NO:1 or SEQ ID NO:4 sense, an anti-sense sequence of SEQ ID NO:1 or SEQ ID NO:4, or naturally occurring mutants thereof. Primers based on the nucleotide sequence in SEQ ID NO:1 or SEQ ID NO:4 can be used in PCR reactions to clone PGC-1 homologues.

In an exemplary embodiment, a nucleic acid molecule of the present invention comprises a nucleotide sequence which is about 100, preferably 100-200, preferably 200-300, more preferably 300-400, and even more preferably 400-487 nucleotides in length and hybridizes under stringent hybridization conditions to a nucleic acid molecule of SEQ ID NO:1 or SEQ ID NO:4.

Probes based on the PGC-1 nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress a PGC-1 protein, such as by measuring a level of a PGC-1-encoding nucleic acid in a sample of cells from a subject e.g., detecting PGC-1 mRNA levels or determining whether a genomic PGC-1 gene has been mutated or deleted.

In one embodiment, the nucleic acid molecule of the invention encodes a protein or portion thereof which includes an amino acid sequence which is sufficiently homologous to an amino acid sequence of SEQ ID NO:2 or SEQ ID NO:5 such that the protein or portion thereof maintains one or more of the following biological activities: 1) it can modulate the expression of phosphoenolpyruvate carboxykinase (PEPCK), glucose-6-phosphatase, and/or fructose-1,6-bisphosphatase; 2) it can bind to and/or modulate the activity of the PEPCK promoter; 3) it can bind to and/or modulate the activity of HNF-4α; 4) it can bind to and/or modulate the activity of FKHR; 5) it can modulate glucose output from a cell; 6) it can modulate gluconeogenesis; 7) it can modulate glucose homeostasis; 8) it can treat diseases or disorders characterized by increased PGC-1 expression or activity, e.g., diabetes or obesity; and 9) it can treat diseases or disorders associated with decreased PGC-1 expression or activity, e.g., diseases or disorders characterized by underproduction of glucose.

As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO:2 or SEQ ID NO:5) amino acid residues to an amino acid sequence of SEQ ID NO:2 or SEQ ID NO:5 such that the protein or portion thereof maintains one or more of the following biological activities: 1) it can modulate the expression of phosphoenolpyruvate carboxykinase (PEPCK), glucose-6-phosphatase, and/or fructose-1,6-bisphosphatase; 2) it can bind to and/or modulate the activity of the PEPCK promoter; 3) it can bind to and/or modulate the activity of HNF-4α; 4) it can bind to and/or modulate the activity of FKHR; 5) it can modulate glucose output from a cell; 6) it can modulate gluconeogenesis; 7) it can modulate glucose homeostasis; 8) it can treat diseases or disorders characterized by increased PGC-1 expression or activity, e.g., diabetes or obesity; and 9) it can treat diseases or disorders associated with decreased PGC-1 expression or activity, e.g., diseases or disorders characterized by underproduction of glucose.

In another embodiment, the protein is at least about 50%, preferably at least about 60%, more preferably at least about 70%, yet more preferably at least about 80%, still more preferably at least about 90%, and most preferably at least about 95% or more homologous to the entire amino acid sequence of SEQ ID NO:2 or SEQ ID NO:5.

Portions of proteins encoded by the PGC-1 nucleic acid molecule of the invention are preferably biologically active portions of the PGC-1 protein. As used herein, the term "biologically active portion of PGC-1" is intended to include a portion, e.g., a domain/motif, of PGC-1 that has one or more of the following activities: 1) it can modulate the expression of phosphoenolpyruvate carboxykinase (PEPCK), glucose-6-phosphatase, and/or fructose-1,6-bisphosphatase; 2) it can bind to and/or modulate the activity of the PEPCK promoter; 3) it can bind to and/or modulate the activity of HNF-4α; 4) it can bind to and/or modulate the activity of FKHR; 5) it can modulate glucose output from a cell; 6) it can modulate gluconeogenesis; 7) it can modulate glucose homeostasis; 8) it can treat diseases or disorders characterized by increased PGC-1 expression or activity, e.g., diabetes or obesity; and 9) it can treat diseases or disorders associated with decreased PGC-1 expression or activity, e.g., diseases or disorders characterized by underproduction of glucose.

Standard binding assays, e.g., immunoprecipitations and yeast two-hybrid assays, as described herein, can be performed to determine the ability of a PGC-1 protein or a biologically active portion thereof to interact with (e.g., bind to) HNF-4α, FKHR, the PEPCK promoter, PPARγ, C/EBPα, or nuclear hormone receptors. If a PGC-1 family member is found to interact with HNF-4α, FKHR, the PEPCK promoter, PPARγ, C/EBPα, and/or nuclear hormone receptors, then they are also likely to be modulators of the activity of HNF-4α, FKHR, the PEPCK promoter, PPARγ, C/EBPα, and nuclear hormone receptors.

To determine whether a PGC-1 family member of the present invention modulates PEPCK, glucose-6-phosphatase, fructose-1,6-bisphosphatase, and/or UCP expression, in vitro transcriptional assays can be performed. To perform such an assay, the full length promoter/enhancer region of the gene of interest (e.g., PEPCK, glucose-6-phosphatase, fructose-1,6-bisphosphatase, or UCP) can be linked to a reporter gene such as chloramphenicol acetyltransferase (CAT) or luciferase and introduced into host cells (e.g., liver cells such as Fao hepatoma cells, or COS cells). The same host cells can then be transfected a nucleic acid molecule encoding the PGC-1 molecule. In some embodiments, nucleic acid molecules encoding HNF-4α, FKHR, and/or PPARγ/RXRα can also be transfected. The effect of the PGC-1 molecule can be measured by testing CAT or luciferase activity and comparing it to CAT or luciferase activity in cells which do not contain nucleic acid encoding the PGC-1 molecule. An increase or decrease in CAT or luciferase activity indicates a modulation of expression of the gene of interest. Because PEPCK, glucose-6-phosphatase and fructose-1,6-bisphosphatase are known to critical components of the gluconeogenic pathway, this assay can also measure the ability of the PGC-1 molecule to modulate gluconeogenesis. In another embodiment, because UCP expression is known to be a critical component in the cascade of events leading to elevated thermogenesis, this assay can also measure the ability of the PGC-1 molecule to modulate thermogenesis in adipocytes.

The above described assay for testing the ability of a PGC-1 molecule to modulate PEPCK, glucose-6-phosphatase and/or fructose-1,6-bisphosphatase expression can also be used to test the ability of the PGC-1 molecule to modulate gluconeogenesis, e.g., de novo synthesis of glucose, as opposed to production of glucose via glycogenolysis, the breakdown of glycogen into glucose. If a PGC-1 molecule can modulate PEPCK, glucose-6-phosphatase and/or fructose-1,6-bisphosphatase expression, it can most likely modulate gluconeogenesis. Alternatively, the ability of a PGC-1 molecule to modulate gluconeogenesis can be measured by introducing a PGC-1 molecule into a cell, e.g., a liver cell such as a Fao hepatoma cell, and measuring the glucose released from the cell into the culture medium, as compared to the amount of glucose released from a control cell which does not contain the PGC-1 molecule.

The above described assay for testing the ability of a PGC-1 molecule to modulate UCP expression can also be used to test the ability of the PGC-1 molecule to modulate adipogenesis, e.g., differentiation of white adipose tissue to brown adipose tissue, as UCP expression is specific to brown adipose tissue. If a PGC-1 molecule can modulate UCP expression is can most likely modulate the differentiation of white adipose tissue to brown adipose tissue.

Alternatively, the ability of a PGC-1 molecule to modulate the differentiation of white adipose tissue to brown adipose tissue can be measured by introducing a PGC-1 molecule into a cell, e.g., a white adipocyte, and measuring the number of mitochondria in the cell as compared to the number of mitochondria in a control cell which does not contain the PGC-1 molecule. As brown adipocytes are known to contain substantially greater numbers of mitochondria than white adipocytes, an increase or decrease in the number of mitochondria (or in a mitochondrial marker such as cytochrome c oxidase) in the test cell as compared to the control cell indicates that the PGC-1 molecule can modulate differentiation of white adipose tissue to brown adipose tissue.

The ability of a PGC-1 molecule to modulate insulin sensitivity of a cell can be determined by performing an assay in which cells, e.g., muscle cells, liver cells, or adipocytes, are transformed to express the PGC-1 protein, incubated with radioactively labeled glucose ($^{14}$C glucose), and treated with insulin. An increase or decrease in glucose in the cells containing PGC-1 as compared to the control cells indicates that the PGC-1 can modulate insulin sensitivity of the cells. Alternatively, the cells containing PGC-1 can be incubated with a radioactively labeled phosphate source (e.g., [$^{32}$P]ATP) and treated with insulin. Phosphorylation of proteins in the insulin pathway, e.g., insulin receptor, can then be measured. An increase or decrease in phosphorylation of a protein in the insulin pathway in cells containing PGC-1 as compared to the control cells indicates that the PGC-1 can modulate insulin sensitivity of the cells.

In one embodiment, the biologically active portion of PGC-1 comprises at least one domain or motif. Examples of such domains/motifs include a tyrosine phosphorylation site, a cAMP phosphorylation site, a serine-arginine (SR) rich domain, an RNA binding motif, and an LXXLL (SEQ ID NO:3) motif which mediates interaction with HNF-4α and nuclear receptors. In one embodiment, the biologically active portion of the protein which includes the domain or motif can modulate differentiation of white adipocytes to brown adipocytes and/or thermogenesis in brown adipocytes. In a preferred embodiment, the domain or motif can modulate gluconeogenesis. These domains are described in detail herein. Additional nucleic acid fragments encoding biologically active portions of PGC-1 can be prepared by isolating a portion of SEQ ID NO:1 or SEQ ID NO:4 or a homologous nucleotide sequence, expressing the encoded portion of PGC-1 protein or peptide (e.g., by recombinant expression in vitro) and assessing the activity of the encoded portion of PGC-1 protein or peptide.

In another embodiment, a PGC-1 nucleic acid molecule encodes a PGC-1 protein which is a "dominant negative". As used herein, the "dominant negative" refers to a protein or polypeptide, or the nucleic acid molecule which encodes it, that, when expressed in a cell, inhibits the activity of its wild type homologue (e.g., the endogenous gene or an exogenously supplied wild type homologue). For example, in a preferred embodiment, a dominant negative PGC-1 molecule is one which, when expressed in a cell (e.g., a liver cell), inhibits at least one or more activities (as described herein) of the wild type PGC-1 gene. In a preferred embodiment, a dominant negative PGC-1 molecule downregulates gluconeogenesis, either partially or completely. In another preferred embodiment, a dominant negative PGC-1 molecule is incapable of binding to HNF-4α but is still capable of binding to other transcription factors, e.g., general transcription factors. Such a dominant negative acts via "squelching". As used herein, the term "squelching" refers to a process by which a dominant negative molecule is expressed at a level such that it binds the majority of certain transcription factors in a cell, leaving none available to bind to the wild-type molecule, effectively rendering the wild type molecule inactive. Depending on the degree of downregulation desired, different dominant negative forms of PGC-1 can be produced which inhibit wild type PGC-1 activities at different levels. In a preferred embodiment, a dominant negative PGC-1 polypeptide comprises a sequence of SEQ ID NO:2 or SEQ ID NO:5, wherein the LXXLL motif (SEQ ID NO:3) is mutated. In one embodiment, one or more of the leucine residues of the LXXLL motif can be substitute with an alternate amino acid residue (e.g., alanine) such that the mutated LXXLL motif no longer mediates binding to HNF-4α or to nuclear receptors. In a preferred embodiment, the leucine residue at the fourth position of the LXXLL motif is substituted with alanine. In another embodiment, at least 1, 2, 3, 4, or 5 amino acid residues of the LXXLL motif are deleted. The mouse LXXLL can be found at amino acid residues 142-146 of SEQ ID NO:2 (encoded by nucleotides 515-529 of SEQ ID NO:1), while the human LXXLL motif can be found at amino acid residues 144-148 of SEQ ID NO:5 (encoded by nucleotides 518-532 of SEQ ID NO:4). Preferably, a PGC-1 polypeptide with a mutated or deleted LXXLL motif is incapable of binding to HNF-4α (see Example section).

The invention further encompasses nucleic acid molecules that differ from the nucleotide sequence shown in SEQ ID NO:1 or SEQ ID NO:4 (and portions thereof) due to degeneracy of the genetic code and thus encode the same PGC-1 protein as that encoded by the nucleotide sequence shown in SEQ ID NO:1 or SEQ ID NO:4. In another embodiment, an isolated nucleic acid molecule of the invention has a nucleotide sequence encoding a protein having an amino acid sequence shown in SEQ ID NO:2 or SEQ ID NO:5 or a protein having an amino acid sequence which is at least about 50%, preferably at least about 60%, more preferably at least about 70%, yet more preferably at least about 80%, still more preferably at least about 90%, and most preferably at least about 95% or more homologous to the amino acid sequence of SEQ ID NO:2 or SEQ ID NO:5.

In addition to the mouse and human PGC-1 nucleotide sequences shown in SEQ ID NO:1 and SEQ ID NO:4, it will be appreciated by those skilled in the art that DNA sequence polymorphisms that lead to changes in the amino acid sequences of PGC-1 may exist within a population (e.g., a mammalian population, e.g., a human population). Such genetic polymorphism in the PGC-1 gene may exist among individuals within a population due to natural allelic variation. As used herein, the terms "gene" and "recombinant gene" refer to nucleic acid molecules comprising an open reading frame encoding a PGC-1 protein, preferably a mammalian, e.g., human, PGC-1 protein. Such natural allelic variations can typically result in 1-5% variance in the nucleotide sequence of the PGC-1 gene. Any and all such nucleotide variations and resulting amino acid polymorphisms in PGC-1 that are the result of natural allelic variation and that do not alter the functional activity of PGC-1 are intended to be within the scope of the invention. Moreover, nucleic acid molecules encoding PGC-1 proteins from other species, and thus which have a nucleotide sequence which differs from the mouse or human sequences of SEQ ID NO:1 and SEQ ID NO:4, are intended to be within the scope of the invention. Nucleic acid molecules corresponding to natural allelic variants and homologues of the mouse or human PGC-1 cDNAs of the invention can be isolated based on their homology to the mouse or human PGC-1 nucleic acid sequences disclosed herein using the mouse or human cDNA, or a portion thereof, as a hybridization probe according to standard hybridization techniques under stringent hybridization conditions (as described herein).

Moreover, nucleic acid molecules encoding other PGC-1 family members and thus which have a nucleotide sequence which differs from the PGC-1 sequences of SEQ ID NO:1 or SEQ ID NO:4 are intended to be within the scope of the invention. For example, a PGC-3 cDNA can be identified based on the nucleotide sequence of human PGC-1 or mouse PGC-1. (It should be noted that a gene called PPARγ coactivator 2, or PGC-2, has already been described in the literature (Castillo, G. et al. (1999) *EMBO J.* 18(13):3676-87). However, PGC-2 is both structurally and functionally unrelated to PGC-1.) Moreover, nucleic acid molecules encoding PGC-1 proteins from different species, and thus which have a nucleotide sequence which differs from the PGC-1 sequences of SEQ ID NO:1 or SEQ ID NO:4 are intended to be within the scope of the invention. For example, rat or monkey PGC-1 cDNA can be identified based on the nucleotide sequence of a human PGC-1.

Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1 or SEQ ID NO:4 or a nucleotide sequence which is about 60%, preferably at least about 70%, more preferably at least about 80%, still more preferably at least about 90%, and most preferably at least about 95% or more homologous to the nucleotide sequence of SEQ ID NO:1 or SEQ ID NO:4. In other embodiments, the nucleic acid is at least 30, 50, 100, 250 or 500 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to the sequence of SEQ ID NO:1, SEQ ID NO:4 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural human PGC-1.

In addition to naturally-occurring allelic variants of the PGC-1 sequence that may exist in the population, the skilled artisan will further appreciate that changes can be introduced by mutation into the nucleotide sequence of SEQ ID NO:1 or SEQ ID NO:4, thereby leading to changes in the amino acid sequence of the encoded PGC-1 protein, without altering the functional ability of the PGC-1 protein. For example, nucleotide substitutions leading to amino acid substitutions at "non-essential" amino acid residues can be made in the sequence of SEQ ID NO:1 or SEQ ID NO:4. A "non-essential" amino acid residue is a residue that can be altered from the wild-type sequence of PGC-1 (e.g., the sequence of SEQ ID NO:2 or SEQ ID NO:5) without altering the activity of PGC-1, whereas an "essential" amino acid residue is required for PGC-1 activity. For example, amino acid residues involved in the interaction of PGC-1 to HNF-4α (e.g., those present in an LXXLL motif) are most likely essential residues of PGC-1. Other amino acid residues, however, (e.g., those that are not conserved or only semi-conserved between mouse and human) may not be essential for activity and thus are likely to be amenable to alteration without altering PGC-1 activity. Furthermore, amino acid residues that are essential for PGC-1 functions related to thermogenesis and/or adipogenesis, but not essential for PGC-1 functions related to gluconeogenesis, are likely to be amenable to alteration.

Accordingly, another aspect of the invention pertains to nucleic acid molecules encoding PGC-1 proteins that contain changes in amino acid residues that are not essential for PGC-1 activity. Such PGC-1 proteins differ in amino acid sequence from SEQ ID NO:2 or SEQ ID NO:5 yet retain at least one of the PGC-1 activities described herein. In one embodiment, the isolated nucleic acid molecule comprises a nucleotide sequence encoding a protein, wherein the protein comprises an amino acid sequence at least about 60% homologous to the amino acid sequence of SEQ ID NO:2 or SEQ ID NO:5 and is capable of modulating gluconeogenesis. Preferably, the protein encoded by the nucleic acid molecule is at least about 70% homologous, preferably at least about 80-85% homologous, still more preferably at least about 90%, and most preferably at least about 95% homologous to the amino acid sequence of SEQ ID NO:2 or SEQ ID NO:5.

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (J. Mol. Biol. (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a PGC-1 protein homologous to the protein of SEQ ID NO:2 or SEQ ID NO:5 can be created by introducing one or more nucleotide substitutions, additions or deletions into the nucleotide sequence of SEQ ID NO:1 or SEQ ID NO:4 or a homologous nucleotide sequence such that one or more amino acid substitutions, additions or deletions are introduced into the encoded protein. Mutations can be introduced into SEQ ID NO:1 or SEQ ID NO:4 or the homologous nucleotide sequence by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in PGC-1 is preferably replaced with another amino acid residue from the same side chain family. Alternatively, in another embodiment, mutations can be introduced randomly along all or part of a PGC-1 coding sequence, such as by saturation mutagenesis, and the resultant mutants can be screened for a PGC-1 activity described herein to identify mutants that retain PGC-1 activity. Following mutagenesis of SEQ ID NO:1 or SEQ ID NO:4, the encoded protein can be expressed recombinantly (as described herein) and the activity of the protein can be determined using, for example, assays described herein.

In addition to the nucleic acid molecules encoding PGC-1 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PGC-1 coding strand, or to only a portion thereof. In one embodiment, an antisense nucleic acid molecule is antisense to a "coding region" of the coding strand of a nucleotide sequence encoding PGC-1. The term "coding region" refers to the region of the nucleotide sequence comprising codons which are translated into amino acid residues (e.g., the entire coding region of SEQ ID NO:1 comprises nucleotides 92 to 2482, the entire coding region of SEQ ID NO:4 comprises nucleotides 89 to 2482). In another embodiment, the antisense nucleic acid molecule is antisense to a "noncoding region" of the coding strand of a nucleotide sequence encoding PGC-1. The term "noncoding region" refers to 5' and 3' sequences which flank the coding region that are not translated into amino acids (i.e., also referred to as 5' and 3' untranslated regions).

Given the coding strand sequences encoding PGC-1 disclosed herein (e.g., SEQ ID NO:1 and SEQ ID NO:4), antisense nucleic acids of the invention can be designed according to the rules of Watson and Crick base pairing. The antisense nucleic acid molecule can be complementary to the entire coding region of PGC-1 mRNA, but more preferably is an oligonucleotide which is antisense to only a portion of the coding or noncoding region of PGC-1 mRNA. For example, the antisense oligonucleotide can be complementary to the region surrounding the translation start site of PGC-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a PGC-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585-591)) can be used to catalytically cleave PGC-1 mRNA transcripts to thereby inhibit translation of PGC-1 mRNA. A ribozyme having specificity for a PGC-1-encoding nucleic acid can be designed based upon the nucleotide sequence of a PGC-1 cDNA disclosed herein (e.g., SEQ ID NO:1 or SEQ ID NO:4). For example, a derivative of a Tetrahymena L-19 IVS RNA can be constructed in which the nucleotide sequence of the active site is complementary to the nucleotide sequence to be cleaved in a PGC-1-encoding mRNA. See, e.g., Cech et al. U.S. Pat. No. 4,987,071 and Cech et al. U.S. Pat. No. 5,116,742. Alternatively, PGC-1 mRNA can be used to select a catalytic RNA having a specific ribonuclease activity from a pool of RNA molecules. See, e.g., Bartel, D. and Szostak, J. W. (1993) *Science* 261:1411-1418.

Alternatively, PGC-1 gene expression can be inhibited by targeting nucleotide sequences complementary to the regulatory region of the PGC-1 (e.g., the PGC-1 promoter and/or enhancers) to form triple helical structures that prevent transcription of the PGC-1 gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15.

II. Recombinant Expression Vectors and Host Cells

Another aspect of the invention pertains to the use of vectors, preferably expression vectors, containing a nucleic acid encoding PGC-1 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Adenoviral vectors comprising a PGC-1 nucleic acid molecule are preferred.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PGC-1 proteins, mutant forms of PGC-1, fusion proteins, etc.).

The recombinant expression vectors of the invention can be designed for expression of PGC-1 in prokaryotic or eukaryotic cells. For example, PGC-1 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the PGC-1 is cloned into a pGEX expression vector to create a vector encoding a fusion protein comprising, from the N-terminus to the C-terminus, GST-thrombin cleavage site-PGC-1. The fusion protein can be purified by affinity chromatography using glutathione-agarose resin. Recombinant PGC-1 unfused to GST can be recovered by cleavage of the fusion protein with thrombin.

Examples of suitable inducible non-fusion *E. coli* expression vectors include pTrc (Amann et al., (1988) *Gene* 69:301-315) and pET11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the PGC-1 expression vector is a yeast expression vector. Examples of vectors for expression in yeast *S. cerivisae* include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, PGC-1 can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195).

When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PGC-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, PGC-1 protein can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding PGC-1 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) PGC-1 protein. Accordingly, the invention further provides methods for producing PGC-1 protein using the host cells of the invention. In one embodiment, the method comprises culturing the host cell of invention (into which a recombinant expression vector encoding PGC-1 has been introduced) in a suitable medium until PGC-1 is produced. In another embodiment, the method further comprises isolating PGC-1 from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as glucose homeostasis disorders, weight disorders or disorders associated with insufficient insulin activity. For example, in one embodiment, a host cell of the invention is a fertilized oocyte or an embryonic stem cell into which PGC-1-coding sequences have been introduced. Such host cells can then be used to create non-human transgenic animals in which exogenous PGC-1 sequences have been introduced into their genome or homologous recombinant animals in which endogenous PGC-1 sequences have been altered. Such animals are useful for studying the function and/or activity of PGC-1 and for identifying and/or evaluating modulators of PGC-1 activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous PGC-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing PGC-1-encoding nucleic acid into the male pronuclei of a fertilized oocyte, e.g., by microinjection, retroviral infection, and allowing the oocyte to develop in a pseudopregnant female foster animal. The human PGC-1 cDNA sequence can be introduced as a transgene into the genome of a nonhuman animal. Alternatively, a nonhuman homologue of the human PGC-1 gene (SEQ ID NO:4), such as a mouse PGC-1 gene (SEQ ID NO:1), can used as a transgene. Intronic sequences and polyadenylation signals can also be included in the transgene to increase the efficiency of expression of the transgene. A tissue-specific regulatory sequence(s) can be operably linked to the PGC-1 transgene to direct expression of PGC-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the PGC-1 transgene in its genome and/or expression of PGC-1 mRNA in tissues or cells of the animals. A transgenic founder animal can then be used to breed additional animals carrying the transgene. Moreover, transgenic animals carrying a transgene encoding PGC-1 can further be bred to other transgenic animals carrying other transgenes.

To create a homologous recombinant animal, a vector is prepared which contains at least a portion of a PGC-1 gene into which a deletion, addition or substitution has been introduced to thereby alter, e.g., functionally disrupt, the PGC-1 gene. The PGC-1 gene can be a human gene (e.g., from a human genomic clone isolated from a human genomic library screened with the cDNA of SEQ ID NO:1), but more preferably, is a nonhuman homologue of a human PGC-1 gene. For example, a mouse PGC-1 gene can be used to construct a homologous recombination vector suitable for altering an endogenous PGC-1 gene in the mouse genome. In a preferred embodiment, the vector is designed such that, upon homologous recombination, the endogenous PGC-1 gene is functionally disrupted (i.e., no longer encodes a functional protein; also referred to as a "knock out" vector). Alternatively, the vector can be designed such that, upon homologous recombination, the endogenous PGC-1 gene is mutated or otherwise altered but still encodes functional protein (e.g., the upstream regulatory region can be altered to thereby alter the expression of the endogenous PGC-1 protein). In the homologous recombination vector, the altered portion of the PGC-1 gene is flanked at its 5' and 3' ends by additional nucleic acid of the PGC-1 gene to allow for homologous recombination to occur between the exogenous PGC-1 gene carried by the vector and an endogenous PGC-1 gene in an embryonic stem cell. The additional flanking PGC-1 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced PGC-1 gene has homologously recombined with the endogenous PGC-1 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated PGC-1 Proteins and Anti-PGC-1 Antibodies

Another aspect of the invention pertains to the use of isolated PGC-1 proteins, and biologically active portions thereof, as well as peptide fragments suitable for use as immunogens to raise anti-PGC-1 antibodies. An "isolated"

or "purified" protein or biologically active portion thereof is substantially free of cellular material when produced by recombinant DNA techniques, or chemical precursors or other chemicals when chemically synthesized. The language "substantially free of cellular material" includes preparations of PGC-1 protein in which the protein is separated from cellular components of the cells in which it is naturally or recombinantly produced. In one embodiment, the language "substantially free of cellular material" includes preparations of PGC-1 protein having less than about 30% (by dry weight) of non-PGC-1 protein (also referred to herein as a "contaminating protein"), more preferably less than about 20% of non-PGC-1 protein, still more preferably less than about 10% of non-PGC-1 protein, and most preferably less than about 5% non-PGC-1 protein. When the PGC-1 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of PGC-1 protein in which the protein is separated from chemical precursors or other chemicals which are involved in the synthesis of the protein. In one embodiment, the language "substantially free of chemical precursors or other chemicals" includes preparations of PGC-1 protein having less than about 30% (by dry weight) of chemical precursors or non-PGC-1 chemicals, more preferably less than about 20% chemical precursors or non-PGC-1 chemicals, still more preferably less than about 10% chemical precursors or non-PGC-1 chemicals, and most preferably less than about 5% chemical precursors or non-PGC-1 chemicals. In preferred embodiments, isolated proteins or biologically active portions thereof lack contaminating proteins from the same animal from which the PGC-1 protein is derived. Typically, such proteins are produced by recombinant expression of, for example, a human PGC-1 protein in a nonhuman cell.

An isolated PGC-1 protein or a portion thereof of the invention has one or more of the following biological activities: 1) it can modulate the expression of phosphoenolpyruvate carboxykinase (PEPCK), glucose-6-phosphatase, and/or fructose-1,6-bisphosphatase; 2) it can bind to and/or modulate the activity of the PEPCK promoter; 3) it can bind to and/or modulate the activity of HNF-4α; 4) it can bind to and/or modulate the activity of FKHR; 5) it can modulate glucose output from a cell; 6) it can modulate gluconeogenesis; 7) it can modulate glucose homeostasis; 8) it can treat diseases or disorders characterized by increased PGC-1 expression or activity, e.g., diabetes or obesity; and 9) it can treat diseases or disorders associated with decreased PGC-1 expression or activity, e.g., diseases or disorders characterized by underproduction of glucose.

In preferred embodiments, the protein or portion thereof comprises an amino acid sequence which is sufficiently homologous to an amino acid sequence of SEQ ID NO:2 or SEQ ID NO:5 such that the protein or portion thereof maintains the ability to modulate gluconeogenesis. The portion of the protein is preferably a biologically active portion as described herein. In another preferred embodiment, the PGC-1 protein (i.e., amino acid residues 1-797 and amino acid residues 1-798) has an amino acid sequence shown in SEQ ID NO:2 or SEQ ID NO:5, respectively, or an amino acid sequence which is at least about 50%, preferably at least about 60%, more preferably at least about 70%, yet more preferably at least about 80%, still more preferably at least about 90%, and most preferably at least about 95% or more homologous to the amino acid sequence shown in SEQ ID NO:2 or SEQ ID NO:5. In yet another preferred embodiment, the PGC-1 protein has an amino acid sequence which is encoded by a nucleotide sequence which hybridizes, e.g., hybridizes under stringent conditions, to the nucleotide sequence of SEQ ID NO:1 or SEQ ID NO:4 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO:1, SEQ ID NO:4. The preferred PGC-1 proteins of the present invention also preferably possess at least one of the PGC-1 biological activities described herein. For example, a preferred PGC-1 protein of the present invention includes an amino acid sequence encoded by a nucleotide sequence which hybridizes, e.g., hybridizes under stringent conditions, to the nucleotide sequence of SEQ ID NO:1 or SEQ ID NO:4 and which can modulate gluconeogenesis.

In other embodiments, the PGC-1 protein is substantially homologous to the amino acid sequence of SEQ ID NO:2 or SEQ ID NO:5 and retains the functional activity of the protein of SEQ ID NO:2 or SEQ ID NO:5 yet differs in amino acid sequence due to natural allelic variation or mutagenesis, as described in detail in subsection I above. Accordingly, in another embodiment, the PGC-1 protein is a protein which comprises an amino acid sequence which is at least about 50%, preferably at least about 60%, more preferably at least about 70%, yet more preferably at least about 80%, still more preferably at least about 90%, and most preferably at least about 95% or more homologous to the amino acid sequence of SEQ ID NO:2, SEQ ID NO:5.

Biologically active portions of the PGC-1 protein include peptides comprising amino acid sequences derived from the amino acid sequence of the PGC-1 protein, e.g., the amino acid sequence shown in SEQ ID NO:2 or SEQ ID NO:5 or the amino acid sequence of a protein homologous to the PGC-1 protein, which include fewer amino acids than the full length PGC-1 protein or the full length protein which is homologous to the PGC-1 protein, and exhibit at least one activity of the PGC-1 protein. Typically, biologically active portions (peptides, e.g., peptides which are, for example, 5, 10, 15, 20, 30, 35, 36, 37, 38, 39, 40, 50, 100 or more amino acids in length) comprise a domain or motif, e.g., a tyrosine phosphorylation site, a cAMP phosphorylation site, a serine-arginine (SR) rich domain, and/or an RNA binding motif, with at least one activity of the PGC-1 protein. In a preferred embodiment, the biologically active portion of the protein which includes one or more the domains/motifs described herein can modulate differentiation of adipocytes and/or thermogenesis in brown adipocytes. Moreover, other biologically active portions, in which other regions of the protein are deleted, can be prepared by recombinant techniques and evaluated for one or more of the activities described herein. Preferably, the biologically active portions of the PGC-1 protein include one or more selected domains/motifs or portions thereof having biological activity.

In a preferred embodiment, the PGC-1 polypeptide is a dominant negative, as described herein. In one embodiment, a dominant negative PGC-1 polypeptide comprises an amino acid sequence of SEQ ID NO:2 or SEQ ID NO:5, wherein the LXXLL motif (e.g., amino acid residues 142-146 of SEQ ID NO:2 or amino acid resides 144-148 of SEQ ID NO:5, also set forth as SEQ ID NO:3) is mutated. In one embodiment, one or more of the leucine residues of the LXXLL motif can be substituted with an alternate amino acid residue (e.g., alanine) such that the mutated LXXLL motif no longer mediates binding to HNF-4α or to nuclear receptors. In a preferred embodiment, the leucine residue at the fourth position of the LXXLL motif is substituted with alanine. In another embodiment, at least 1, 2, 3, 4, or 5 amino acid residues of the LXXLL motif are deleted.

PGC-1 proteins are preferably produced by recombinant DNA techniques. For example, a nucleic acid molecule encoding the protein is cloned into an expression vector (as described above), the expression vector is introduced into a host cell (as described above) and the PGC-1 protein is expressed in the host cell. The PGC-1 protein can then be isolated from the cells by an appropriate purification scheme using standard protein purification techniques. Alternative to recombinant expression, a PGC-1 protein, polypeptide, or peptide can be synthesized chemically using standard peptide synthesis techniques. Moreover, native PGC-1 protein can be isolated from cells (e.g., brown adipocytes), for example using an anti-PGC-1 antibody (described further below).

The invention also provides PGC-1 chimeric or fusion proteins. As used herein, a PGC-1 "chimeric protein" or "fusion protein" comprises a PGC-1 polypeptide operatively linked to a non-PGC-1 polypeptide. A "PGC-1 polypeptide" refers to a polypeptide having an amino acid sequence corresponding to PGC-1, whereas a "non-PGC-1 polypeptide" refers to a polypeptide having an amino acid sequence corresponding to a protein which is not substantially homologous to the PGC-1 protein, e.g., a protein which is different from the PGC-1 protein and which is derived from the same or a different organism. Within the fusion protein, the term "operatively linked" is intended to indicate that the PGC-1 polypeptide and the non-PGC-1 polypeptide are fused in-frame to each other. The non-PGC-1 polypeptide can be fused to the N-terminus or C-terminus of the PGC-1 polypeptide. For example, in one embodiment the fusion protein is a GST-PGC-1 fusion protein in which the PGC-1 sequences are fused to the C-terminus of the GST sequences. Such fusion proteins can facilitate the purification of recombinant PGC-1. In another embodiment, the fusion protein is a PGC-1 protein containing a heterologous signal sequence at its N-terminus. In certain host cells (e.g., mammalian host cells), expression and/or secretion of PGC-1 can be increased through use of a heterologous signal sequence.

Preferably, a PGC-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A PGC-1-encoding nucleic acid can be cloned into such an expression vector such that the fusion moiety is linked in-frame to the PGC-1 protein.

The present invention also pertains to homologues of the PGC-1 proteins which function as either a PGC-1 agonist (mimetic) or a PGC-1 antagonist. In a preferred embodiment, the PGC-1 agonists and antagonists stimulate or inhibit, respectively, a subset of the biological activities of the naturally occurring form of the PGC-1 protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the PGC-1 protein.

Homologues of the PGC-1 protein can be generated by mutagenesis, e.g., discrete point mutation or truncation of the PGC-1 protein. As used herein, the term "homologue" refers to a variant form of the PGC-1 protein which acts as an agonist or antagonist of the activity of the PGC-1 protein. An agonist of the PGC-1 protein can retain substantially the same, or a subset, of the biological activities of the PGC-1 protein. An antagonist of the PGC-1 protein can inhibit one or more of the activities of the naturally occurring form of the PGC-1 protein, by, for example, competitively binding to a downstream or upstream member of the PGC-1 cascade which includes the PGC-1 protein. Thus, the mammalian PGC-1 protein and homologues thereof of the present invention can be, for example, either positive or negative regulators of adipocyte differentiation and/or thermogenesis in brown adipocytes.

In an alternative embodiment, homologues of the PGC-1 protein can be identified by screening combinatorial libraries of mutants, e.g., truncation mutants, of the PGC-1 protein for PGC-1 protein agonist or antagonist activity. In one embodiment, a variegated library of PGC-1 variants is generated by combinatorial mutagenesis at the nucleic acid level and is encoded by a variegated gene library. A variegated library of PGC-1 variants can be produced by, for example, enzymatically ligating a mixture of synthetic oligonucleotides into gene sequences such that a degenerate set of potential PGC-1 sequences is expressible as individual polypeptides, or alternatively, as a set of larger fusion proteins (e.g., for phage display) containing the set of PGC-1 sequences therein. There are a variety of methods which can be used to produce libraries of potential PGC-1 homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PGC-1 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the PGC-1 protein coding can be used to generate a variegated population of PGC-1 fragments for screening and subsequent selection of homologues of a PGC-1 protein. In one embodiment, a library of coding sequence fragments can be generated by treating a double stranded PCR fragment of a PGC-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PGC-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PGC-1 homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PGC-1 homologues (Arkin and Youvan (1992) *Proc. Natl. Acad. Sci. USA* 89:7811-7815; Delagrave et al. (1993) *Protein Engineering* 6(3):327-331).

An isolated PGC-1 protein, or a portion or fragment thereof, can be used as an immunogen to generate antibodies that bind PGC-1 using standard techniques for polyclonal and monoclonal antibody preparation. The full-length PGC-1 protein can be used or, alternatively, the invention provides antigenic peptide fragments of PGC-1 for use as immunogens. The antigenic peptide of PGC-1 comprises at least 8 amino acid residues of the amino acid sequence shown in SEQ ID NO:2, SEQ ID NO:5 or a homologous amino acid sequence as described herein and encompasses an epitope of PGC-1 such that an antibody raised against the peptide forms a specific immune complex with PGC-1. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of PGC-1 that are located on the surface of the protein, e.g., hydrophilic regions.

A PGC-1 immunogen typically is used to prepare antibodies by immunizing a suitable subject, (e.g., rabbit, goat, mouse or other mammal) with the immunogen. An appropriate immunogenic preparation can contain, for example, recombinantly expressed PGC-1 protein or a chemically synthesized PGC-1 peptide. The preparation can further include an adjuvant, such as Freund's complete or incomplete adjuvant, or similar immunostimulatory agent. Immunization of a suitable subject with an immunogenic PGC-1 preparation induces a polyclonal anti-PGC-1 antibody response.

Accordingly, another aspect of the invention pertains to anti-PGC-1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as PGC-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind PGC-1. The term "monoclonal antibody" or "monoclonal antibody composition", as used herein, refers to a population of antibody molecules that contain only one species of an antigen binding site capable of immunoreacting with a particular epitope of PGC-1. A monoclonal antibody composition thus typically displays a single binding affinity for a particular PGC-1 protein with which it immunoreacts.

Polyclonal anti-PGC-1 antibodies can be prepared as described above by immunizing a suitable subject with a PGC-1 immunogen. The anti-PGC-1 antibody titer in the immunized subject can be monitored over time by standard techniques, such as with an enzyme linked immunosorbent assay (ELISA) using immobilized PGC-1. If desired, the antibody molecules directed against PGC-1 can be isolated from the mammal (e.g., from the blood) and further purified by well known techniques, such as protein A chromatography to obtain the IgG fraction. At an appropriate time after immunization, e.g., when the anti-PGC-1 antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) Yale *J. Biol. Med.,* 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a PGC-1 immunogen as described above, and the culture supernatants of the resulting hybridoma cells are screened to identify a hybridoma producing a monoclonal antibody that binds PGC-1.

Any of the many well known protocols used for fusing lymphocytes and immortalized cell lines can be applied for the purpose of generating an anti-PGC-1 monoclonal antibody (see, e.g., G. Galfre et al. (1977) *Nature* 266:55052; Gefter et al. *Somatic Cell Genet.,* cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PGC-1, e.g., using a standard ELISA assay.

Alternative to preparing monoclonal antibody-secreting hybridomas, a monoclonal anti-PGC-1 antibody can be identified and isolated by screening a recombinant combinatorial immunoglobulin library (e.g., an antibody phage display library) with PGC-1 to thereby isolate immunoglobulin library members that bind PGC-1. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-PGC-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-PGC-1 antibody (e.g., monoclonal antibody) can be used to isolate PGC-1 by standard techniques, such as affinity chromatography or immunoprecipitation. An anti-PGC-1 antibody can facilitate the purification of natural PGC-1 from cells and of recombinantly produced PGC-1 expressed in host cells. Moreover, an anti-PGC-1 antibody can be used to detect PGC-1 protein (e.g., in a cellular lysate or cell supernatant) in order to evaluate the abundance and pattern of expression of the PGC-1 protein. Anti-PGC-1 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

IV. Pharmaceutical Compositions

The PGC-1 nucleic acid molecules, PGC-1 proteins, PGC-1 modulators, and anti-PGC-1 antibodies (also referred to herein as "active compounds") of the invention can be incorporated into pharmaceutical compositions suitable for administration to a subject, e.g., a human. Such compositions typically comprise the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a PGC-1 protein or anti-PGC-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

Viral vectors include, for example, recombinant retroviruses, adenovirus, adeno-associated virus, and herpes simplex virus-1. Retrovirus vectors and adeno-associated virus vectors are generally understood to be the recombinant gene delivery system of choice for the transfer of exogenous genes in vivo, particularly into humans. In particular, adenovirus is particularly preferred in the instant invention because it preferentially targets the liver (e.g. the major site of gluconeogenesis) when administered systemically (greater than 90+%; (Antinozzi et al. (1999) *Annu. Rev. Nutr.* 19:511-544) for reasons that may have to do with the expression of viral receptors or the lack of vascular barriers in the liver. Alternatively they can be used for introducing exogenous genes ex vivo into liver cells in culture. These vectors provide efficient delivery of genes into liver cells, and the transferred nucleic acids are stably integrated into the chromosomal DNA of the host cell.

A major prerequisite for the use of viruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) is replaced by a gene of interest rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm.

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *Proc. Natl. Acad. Sci. USA* 86:9079-9083; Julan et al. (1992) *J. Gen. Virol.* 73:3251-3255; and Goud et al. (1983) *Virology* 163:251-254); or coupling cell surface receptor ligands to the viral env proteins (Neda et al. (1991) *J. Biol. Chem.* 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). Thus, in a specific embodiment of the invention, viral particles containing a nucleic acid molecule containing a gene of interest operably linked to appropriate regulatory elements, are modified for example according to the methods described above, such that they can specifically target subsets of liver cells. For example, the viral particle can be coated with antibodies to surface molecule that are specific to certain types of liver cells. This method is particularly useful when only specific subsets of liver cells are desired to be transfected.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *Biotechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109-127). Expression of the gene of interest comprised in the nucleic acid molecule can be under control of, for example, the E1A promoter, the major late promoter (MLP) and associated leader sequences, the E3 promoter, or exogenously added promoter sequences.

Yet another viral vector system useful for delivery of a nucleic acid molecule comprising a gene of interest is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics Microbiol. Immunol.* (1992) 158:97-129). Adeno-associated viruses exhibit a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as few as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into T cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790). Other viral vector systems that may have application in gene therapy have been derived from herpes virus, vaccinia virus, and several RNA viruses.

Other methods relating to the use of viral vectors in gene therapy can be found in, e.g., Kay, M. A. (1997) *Chest* 111(6 Supp.):138S-142S; Ferry, N. and Heard, J. M. (1998) *Hum. Gene Ther.* 9:1975-81; Shiratory, Y. et al. (1999) *Liver* 19:265-74; Oka, K. et al. (2000) *Curr. Opin. Lipidol.* 11:179-86; Thule, P. M. and Liu, J. M. (2000) *Gene Ther.* 7:1744-52; Yang, N. S. (1992) *Crit. Rev. Biotechnol.* 12:335-56; Alt, M. (1995) *J. Hepatol.* 23:746-58; Brody, S. L. and Crystal, R. G. (1994) *Ann. N.Y. Acad. Sci.* 716:90-101; Strayer, D. S. (1999) *Expert Opin. Invetig. Drugs* 8:2159-2172; Smith-Arica, J. R. and Bartlett, J. S. (2001) *Curr. Cardiol. Rep.* 3:43-49; and Lee, H. C. et al. (2000) *Nature* 408:483-8.

The pharmaceutical compositions can be included in a container, pack, or dispenser together with instructions for administration.

V. Uses and Methods of the Invention

The nucleic acid molecules, polypeptides, polypeptide homologues, modulators, and antibodies described herein can be used in one or more of the following methods: 1) drug screening assays; 2) diagnostic assays; and 3) methods of treatment. A PGC-1 protein of the invention has one or more of the activities described herein and can thus be used to, for example, modulate adipocyte differentiation, thermogenesis in brown adipocytes, and insulin sensitivity in various cells, e.g., muscle cells, liver cells, and adipocytes. The isolated nucleic acid molecules of the invention can be used to express PGC-1 protein (e.g., via a recombinant expression vector in a host cell in gene therapy applications), to detect PGC-1 mRNA (e.g., in a biological sample) or a genetic lesion in a PGC-1 gene, and to modulate PGC-1 activity, as described further below. In addition, the PGC-1 proteins can be used to screen drugs or compounds which modulate PGC-1 protein activity as well as to treat disorders characterized by insufficient excessive production of PGC-1 protein or production of PGC-1 protein forms which have increased or decreased activity compared to wild type PGC-1. Moreover, the anti-PGC-1 antibodies of the invention can be used to detect and isolate PGC-1 protein and modulate PGC-1 protein activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to PGC-1 proteins, have a stimulatory or inhibitory effect on, for example, PGC-1 expression or PGC-1 activity, or have a stimulatory or inhibitory effect on, for example, the expression or activity of a PGC-1 target molecule.

In one embodiment, the invention provides assays for screening candidate or test compounds which are target molecules of a PGC-1 protein or polypeptide or biologically active portion thereof. In another embodiment, the invention provides assays for screening candidate or test compounds which bind to or modulate the activity of a PGC-1 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:45).

Examples of methods for the synthesis of molecular libraries can be found in the art, for example, in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.).

In one embodiment, an assay is a cell-based assay in which a cell which expresses a PGC-1 protein or biologically active portion thereof is contacted with a test compound and the ability of the test compound to modulate PGC-1 activity is determined. Determining the ability of the test compound to modulate PGC-1 activity can be accomplished by monitoring, for example, PEPCK, glucose-6-phosphatase, and/or fructose-1,6-bisphosphatase expression; and/or glucose release into the culture medium in a cell which expresses PGC-1. The cell, for example, can be of mammalian origin, e.g., an Fao hepatoma cell.

The ability of the test compound to modulate PGC-1 binding to a target molecule (e.g., HNF-4α, FKHR, or the PEPCK promoter) or to bind to PGC-1 can also be determined. Determining the ability of the test compound to modulate PGC-1 binding to a target molecule can be accomplished, for example, by coupling the PGC-1 target molecule with a radioisotope or enzymatic label such that binding of the PGC-1 target molecule to PGC-1 can be determined by detecting the labeled PGC-1 target molecule in a complex. Alternatively, PGC-1 could be coupled with a radioisotope or enzymatic label to monitor the ability of a test compound to modulate PGC-1 binding to a PGC-1 target molecule in a complex. Determining the ability of the test compound to bind PGC-1 can be accomplished, for example, by coupling the compound with a radioisotope or enzymatic label such that binding of the compound to PGC-1 can be determined by detecting the labeled PGC-1 compound in a complex. For example, compounds (e.g., PGC-1 target molecules) can be labeled with $^{125}$I, $^{35}$S, $^{14}$C, or $^3$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a PGC-1 target molecule such as HNF-4α or FKHR) to interact with PGC-1 without the labeling of any of the interactants. For example, a microphysiometer can be used to detect the interaction of a compound with PGC-1 without the labeling of either the compound or the PGC-1. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and PGC-1.

In another embodiment, an assay is a cell-based assay comprising contacting a cell expressing a PGC-1 target molecule (e.g., HNF-4α, FKHR, or a PEPCK promoter reporter construct) with a test compound and determining the ability of the test compound to modulate (e.g. stimulate or inhibit) the activity of the PGC-1 target molecule. Determining the ability of the test compound to modulate the activity of a PGC-1 target molecule can be accomplished, for example, by determining the ability of a PGC-1 protein to bind to or interact with the PGC-1 target molecule (e.g., HNF-4α, FKHR, or the PEPCK promoter), or by determining the ability of a PGC-1 protein to induce expression from the PEPCK promoter reporter construct.

Determining the ability of the PGC-1 protein, or a biologically active fragment thereof, to bind to or interact with a PGC-1 target molecule can be accomplished by one of the methods described above for determining direct binding. In a preferred embodiment, determining the ability of the PGC-1 protein to bind to or interact with a PGC-1 target molecule can be accomplished by determining the activity of the target molecule. For example, the activity of the target molecule can be determined by detecting induction of a cellular response, detecting catalytic/enzymatic activity of the target molecule upon an appropriate substrate, detecting the induction of a reporter gene (comprising a target-responsive regulatory element operatively linked to a nucleic acid encoding a detectable marker, e.g., luciferase), or detecting a target-regulated cellular response (i.e., glucose output).

In yet another embodiment, an assay of the present invention is a cell-free assay in which a PGC-1 protein or biologically active portion thereof is contacted with a test compound and the ability of the test compound to bind to the PGC-1 protein or biologically active portion thereof is determined. Preferred biologically active portions of the PGC-1 proteins to be used in assays of the present invention include fragments which participate in interactions with HNF-4α, FKHR, or the PEPCK promoter. Binding of the test compound to the PGC-1 protein can be determined either directly or indirectly as described above. In a preferred embodiment, the assay includes contacting the PGC-1 protein or biologically active portion thereof with a known compound which binds PGC-1 to form an assay mixture, contacting the assay mixture with a test compound, and determining the ability of the test compound to interact with a PGC-1 protein, wherein determining the ability of the test compound to interact with a PGC-1 protein comprises determining the ability of the test compound to preferentially bind to PGC-1 or biologically active portion thereof as compared to the known compound.

In another embodiment, the assay is a cell-free assay in which a PGC-1 protein or biologically active portion thereof is contacted with a test compound and the ability of the test compound to modulate (e.g., stimulate or inhibit) the activity of the PGC-1 protein or biologically active portion thereof is determined. Determining the ability of the test compound to modulate the activity of a PGC-1 protein can be accomplished, for example, by determining the ability of the PGC-1 protein to bind to a PGC-1 target molecule by one of the methods described above for determining direct binding. Determining the ability of the PGC-1 protein to bind to a PGC-1 target molecule can also be accomplished using a technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a PGC-1 protein can be accomplished by determining the ability of the PGC-1 protein to further modulate the activity of a downstream effector of a PGC-1 target molecule. For example, the activity of the effector molecule on an appropriate target can be determined or the binding of the effector to an appropriate target can be determined as previously described.

In yet another embodiment, the cell-free assay involves contacting a PGC-1 protein or biologically active portion thereof with a known compound which binds the PGC-1 protein (e.g., HNF-4α, FKHR, or the PEPCK promoter) to form an assay mixture, contacting the assay mixture with a test compound, and determining the ability of the test compound to interact with the PGC-1 protein, wherein determining the ability of the test compound to interact with the PGC-1 protein comprises determining the ability of the PGC-1 protein to preferentially bind to or modulate the activity of a PGC-1 target molecule.

In more than one embodiment of the above assay methods of the present invention, it may be desirable to immobilize either PGC-1 or its target molecule to facilitate separation of complexed from uncomplexed forms of one or both of the proteins, as well as to accommodate automation of the assay. Binding of a test compound to a PGC-1 protein, or interaction of a PGC-1 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-5-transferase/PGC-1 fusion proteins or glutathione-S-transferase/target fusion proteins can be adsorbed onto glutathione sepharose beads (Sigma Chemical, St. Louis, Mo.) or glutathione derivatized micrometer plates, which are then combined with the test compound or the test compound and either the non-adsorbed target protein or PGC-1 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of PGC-1 binding or activity determined using standard techniques.

Other techniques for immobilizing proteins on matrices can also be used in the screening assays of the invention. For example, either a PGC-1 protein or a PGC-1 target molecule can be immobilized utilizing conjugation of biotin and streptavidin. Biotinylated PGC-1 protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with PGC-1 protein or target molecules but which do not interfere with binding of the PGC-1 protein to its target molecule can be derivatized to the wells of the plate, and unbound target or PGC-1 protein trapped in the wells by antibody conjugation. Methods for detecting such complexes, in addition to those described above for the GST-immobilized complexes, include immunodetection of complexes using antibodies reactive with the PGC-1 protein or target molecule, as well as enzyme-linked assays which rely on detecting an enzymatic activity associated with the PGC-1 protein or target molecule.

In another embodiment, modulators of PGC-1 expression are identified in a method wherein a cell is contacted with a candidate compound and the expression of PGC-1 mRNA or protein in the cell is determined. The level of expression of PGC-1 mRNA or protein in the presence of the candidate compound is compared to the level of expression of PGC-1 mRNA or protein in the absence of the candidate compound. The candidate compound can then be identified as a modulator of PGC-1 expression based on this comparison. For example, when expression of PGC-1 mRNA or protein is greater (statistically significantly greater) in the presence of the candidate compound than in its absence, the candidate compound is identified as a stimulator of PGC-1 mRNA or protein expression. Alternatively, when expression of PGC-1 mRNA or protein is less (statistically significantly less) in the presence of the candidate compound than in its absence, the candidate compound is identified as an inhibitor of PGC-1 mRNA or protein expression. The level of PGC-1 mRNA or protein expression in the cells can be determined by methods described herein for detecting PGC-1 mRNA or protein.

In yet another aspect of the invention, the PGC-1 proteins can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300) to identify other proteins which bind to or interact with PGC-1 ("PGC-1-binding proteins" or "PGC-1-bp") and are involved in PGC-1 activity. Such PGC-1-binding proteins are also likely to be involved in the propagation of signals by the PGC-1 proteins or PGC-1 targets as, for example, downstream elements of a PGC-1-mediated signaling pathway. Alternatively, such PGC-1-binding proteins may be PGC-1 inhibitors.

The two-hybrid system is based on the modular nature of most transcription factors, which consist of separable DNA-binding and activation domains. Briefly, the assay utilizes two different DNA constructs. In one construct, the gene that codes for a PGC-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PGC-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the PGC-1 protein.

In another aspect, the invention pertains to a combination of two or more of the assays described herein. For example, a modulating agent can be identified using a cell-based or a cell-free assay, and the ability of the agent to modulate the activity of a PGC-1 protein can be confirmed in vivo, e.g., in an animal such as an animal model for diabetes. Such an animal can be produced, for example, by treating a mouse or a rat with streptozotocin, as described in the examples section.

This invention further pertains to novel agents identified by the above-described screening assays. Accordingly, it is within the scope of this invention to further use an agent identified as described herein in an appropriate animal model. For example, an agent identified as described herein (e.g., a PGC-1 modulating agent, an antisense PGC-1 nucleic acid molecule, a PGC-1-specific antibody, or a PGC-1 binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

In yet another embodiment, the invention provides a method for identifying a compound (e.g., a screening assay) capable of use in the treatment of a disorder characterized by (or associated with) aberrant or abnormal PGC-1 nucleic acid expression or PGC-1 polypeptide activity. This method typically includes the step of assaying the ability of the compound or agent to modulate the expression of the PGC-1 nucleic acid or the activity of the PGC-1 protein thereby identifying a compound for treating a disorder characterized by aberrant or abnormal PGC-1 nucleic acid expression or PGC-1 polypeptide activity. Disorders characterized by aberrant or abnormal PGC-1 nucleic acid expression or PGC-1 protein activity are described herein. Methods for assaying the ability of the compound or agent to modulate the expression of the PGC-1 nucleic acid or activity of the PGC-1 protein are typically cell-based assays. For example, cells which are sensitive to ligands which transduce signals via a pathway involving PGC-1 can be induced to overexpress a PGC-1 protein in the presence and absence of a candidate compound. Candidate compounds which produce a statistically significant change in PGC-1-dependent responses (either stimulation or inhibition) can be identified. In one embodiment, expression of the PGC-1 nucleic acid or activity of a PGC-1 protein is modulated in cells and the effects of candidate compounds on the readout of interest (such as rate of cell proliferation or differentiation) are measured. For example, the expression of genes which are up- or down-regulated in response to a PGC-1 protein-dependent signal cascade (e.g., PEPCK, glucose-6-phosphatase, and/or fructose-1,6-bisphosphatase) can be assayed. In preferred embodiments, the regulatory regions of such genes, e.g., the 5' flanking promoter and enhancer regions, are operably linked to a detectable marker (such as luciferase) which encodes a gene product that can be readily detected. Phosphorylation of PGC-1 or PGC-1 target molecules can also be measured, for example, by immunoblotting.

Alternatively, modulators of PGC-1 nucleic acid expression (e.g., compounds which can be used to treat a disorder characterized by aberrant or abnormal PGC-1 nucleic acid expression or PGC-1 protein activity) can be identified in a method wherein a cell is contacted with a candidate compound and the expression of PGC-1 mRNA or protein in the cell is determined. The level of expression of PGC-1 mRNA or protein in the presence of the candidate compound is compared to the level of expression of PGC-1 mRNA or protein in the absence of the candidate compound. The candidate compound can then be identified as a modulator of PGC-1 nucleic acid expression based on this comparison and be used to treat a disorder characterized by aberrant PGC-1 nucleic acid expression. For example, when expression of PGC-1 mRNA or polypeptide is greater (statistically significantly greater) in the presence of the candidate compound than in its absence, the candidate compound is identified as a stimulator of PGC-1 nucleic acid expression. Alternatively, when PGC-1 nucleic acid expression is less (statistically significantly less) in the presence of the candidate compound than in its absence, the candidate compound is identified as an inhibitor of PGC-1 nucleic acid expression. The level of PGC-1 nucleic acid expression in the cells can be determined by methods described herein for detecting PGC-1 mRNA or protein.

Modulators of PGC-1 protein activity and/or PGC-1 nucleic acid expression identified according to these drug screening assays can be used to treat, for example, glucose homeostasis disorders such as diabetes (e.g., type 1 diabetes, type 2 diabetes, and maturity onset diabetes of the young (MODY)) and hepatic enzyme abnormalities that lead to hypoglycemia. Modulators of PGC-1 protein activity and/or PGC-1 nucleic acid expression may also be used to treat disorders related to other functions of PGC-1 unrelated to gluconeogenesis, such as weight disorders, e.g. obesity. These methods of treatment include the steps of administering the modulators of PGC-1 protein activity and/or nucleic acid expression, e.g., in a pharmaceutical composition as described in subsection IV above, to a subject in need of such treatment, e.g., a subject with a disorder described herein.

B. Diagnostic Assays:

The invention further provides a method for detecting the presence of PGC-1 in a biological sample. Such a method may be used to identify subjects with aberrant or abnormal PGC-1 nucleic acid expression or PGC-1 protein activity, e.g., diabetes. The method involves contacting the biological sample with a compound or an agent capable of detecting PGC-1 polypeptide or mRNA such that the presence of PGC-1 is detected in the biological sample. A preferred agent for detecting PGC-1 mRNA is a labeled or labelable nucleic acid probe capable of hybridizing to PGC-1 mRNA. The nucleic acid probe can be, for example, the full-length PGC-1 cDNA of SEQ ID NO:1 or 4, or a portion thereof, such as an oligonucleotide of at least 15, 30, 50, 100, 250 or 500 nucleotides in length and sufficient to specifically hybridize under stringent conditions to PGC-1 mRNA. A preferred agent for detecting PGC-1 protein is a labeled or labelable antibody capable of binding to PGC-1 protein. Antibodies can be polyclonal, or more preferably, monoclonal. An intact antibody, or a fragment thereof (e.g., Fab or $F(ab')_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect PGC-1 mRNA or protein in a biological sample in vitro as well as in vivo. For example, in vitro techniques for detection of PGC-1 mRNA include Northern hybridizations and in situ hybridizations. In vitro techniques for detection of PGC-1 protein include enzyme linked immunosorbent assays (ELISAs), Western blots, immunoprecipitations and immunofluorescence. Alternatively, PGC-1 protein can be detected in vivo in a subject by introducing into the subject a labeled anti-PGC-1 antibody. For example, the antibody can be labeled with a radioactive marker whose presence and location in a subject can be detected by standard imaging techniques.

The invention also encompasses kits for detecting the presence of PGC-1 in a biological sample. For example, the kit can comprise a labeled or labelable compound or agent capable of detecting PGC-1 protein or mRNA in a biological sample; means for determining the amount of PGC-1 in the sample; and means for comparing the amount of PGC-1 in the sample with a standard. The compound or agent can be packaged in a suitable container. The kit can further comprise instructions for using the kit to detect PGC-1 mRNA or protein.

The methods of the invention can also be used to detect genetic lesions in a PGC-1 gene, thereby determining if a subject with the lesioned gene is at risk for a disorder characterized by aberrant or abnormal PGC-1 nucleic acid expression or PGC-1 protein activity as defined herein. In preferred embodiments, the methods include detecting, in a sample of cells from the subject, the presence or absence of a genetic lesion characterized by at least one of an alteration affecting the integrity of a gene encoding a PGC-1 protein, or the misexpression of the PGC-1 gene. For example, such genetic lesions can be detected by ascertaining the existence of at least one of 1) a deletion of one or more nucleotides from a PGC-1 gene; 2) an addition of one or more nucleotides to a PGC-1 gene; 3) a substitution of one or more nucleotides of a PGC-1 gene, 4) a chromosomal rearrangement of a PGC-1 gene; 5) an alteration in the level of a messenger RNA transcript of a PGC-1 gene, 6) aberrant modification of a PGC-1 gene, such as of the methylation pattern of the genomic DNA, 7) the presence of a non-wild type splicing pattern of a messenger RNA transcript of a PGC-1 gene, 8) a non-wild type level of a PGC-1-protein, 9) allelic loss of a PGC-1 gene, and 10) inappropriate post-translational modification of a PGC-1-protein. As described herein, there are a large number of assay techniques known in the art which can be used for detecting lesions in a PGC-1 gene.

In certain embodiments, detection of the lesion involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the PGC-1-gene (see Abravaya et al. (1995) *Nucleic Acids Res.* 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a PGC-1 gene under conditions such that hybridization and amplification of the PGC-1-gene (if present) occurs, and detecting the presence or absence of an amplification product, or detecting the size of the amplification product and comparing the length to a control sample.

In an alternative embodiment, mutations in a PGC-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the PGC-1 gene and detect mutations by comparing the sequence of the sample PGC-1 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). A variety of automated sequencing procedures can be utilized when performing the diagnostic assays (Naeve et al. (1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the PGC-1 gene include methods in which protection from cleavage agents is used to detect mismatched bases in RNA/RNA or RNA/DNA duplexes (Myers et al. (1985) *Science* 230:1242); Cotton et al. (1988) *Proc. Natl. Acad. Sci. USA* 85:4397; Saleeba et al. (1992) *Methods Enzymol.* 217:286-295), electrophoretic mobility of mutant and wild type nucleic acid is compared (Orita et al. (1989) *Proc. Natl. Acad. Sci. USA* 86:2766; Cotton (1993) *Mutat. Res.* 285:125-144; and Hayashi (1992) *Genet. Anal. Tech. Appl.* 9:73-79), and movement of mutant or wild-type fragments in polyacrylamide gels containing a gradient of denaturant is assayed using denaturing gradient gel electrophoresis (Myers et al (1985) *Nature* 313:495). Examples of other techniques for detecting point mutations include, selective oligonucleotide hybridization, selective amplification, and selective primer extension.

This invention is further illustrated by the following examples which should not be construed as limiting. The contents of all references, patent applications, patents, and published patent applications, as well as the Figures and the Sequence Listing, cited throughout this application are hereby incorporated by reference.

EXAMPLES

Materials and Methods

Cell Culture

Primary rat hepatocytes were purchased from a commercial vendor (In vitro Technologies) and cultured in 10% fetal bovine serum (FBS) (Hyclone)-Dulbecco's modified Eagle medium (DMEM) (Cellgro) at 5% $CO_2$. For hormonal stimulation experiments, cells were incubated in serum-free DMEM overnight before addition of hormones. Fao rat hepatoma cells were maintained in 10% FBS-Roswell Park Memorial Institute 1640 medium (RPMI) (Cellgro) at 5% $CO_2$.

Animal Experiments

For the feeding experiments, male mice were either allowed free access to food or subjected to a 24 hour fast and sacrificed at the end of 24 hours. A third group was fasted for 24 hours and then fed ad libitum for another 24 hours prior to sacrifice. For the STZ-diabetic mouse experiments, 6-8 week old male mice (n=3 per group) were injected intraperitoneally for three consecutive days with either sodium citrate solution or streptozotocin (100 mg/g of body weight per injection). Animals were sacrificed after 10 days, at which point the mean blood glucose in the STZ-treated group rose to over 400 mg/dl. For the LIRKO mouse experiments, two-month-old female control (lox/lox) or LIRKO mice were divided into three groups (n=2 each) and subjected to the standard feeding protocol as described above.

Northern Analysis

Total RNA was prepared from cells or tissues with Trizol (Life Technologies) according to the manufacturer's instructions. Ten to twenty micrograms of total RNA was fractionated in a 1% agarose-formaldehyde gel, transferred onto nylon, and hybridized with cDNA probes labeled by random-primed labeling (Boehringer Mannheim) with $[-^{32}P]$-dCTP, using methods known in the art.

Adenoviral Infection

Primary hepatocytes were infected 48 hours after plating with adenoviruses constructed to express either green fluorescent protein (GFP) or PGC-1. Cells were harvested for RNA or protein isolation 48 to 72 hours after infection. Glucose production assays were performed 48 hours after infection.

Glucose Production Assay

Primary hepatocytes were cultured in 6 well plates (1.4 million cells per well) in 10% FBS-DMEM or, in the case of hormonal treatments, in serum-free DMEM. The medium was then replaced with 1 ml of glucose production buffer consisting of glucose-free DMEM (pH 7.4), without phenol red, supplemented with 20 mM sodium lactate and 2 mM sodium pyruvate. After a 3 hour incubation, 0.5 ml of medium was collected and the glucose concentration measured using a calorimetric glucose assay kit (Sigma). The readings were then normalized to the total protein content determined separately from the whole cell lysates.

Western Analysis

Whole cell extracts were prepared by lysing the cells in a buffer containing 100 mM Tris (pH 8.5), 250 mM NaCl, 1% NP-40, 1 mM EDTA, Complete™ protease inhibitors (Boehringer Mannheim), and 0.1% phenylmethylsulfonyl fluoride (PMSF), and were centrifuged at 14,000 g for 10 minutes to remove cellular debris. Tissue extracts were prepared by homogenizing in the lysis buffer with a Polytron homogenizer, followed by centrifugation to remove particulate matter. Proteins were separated by SDS-PAGE, transferred to Immobilon P membrane (Millipore), and probed with polyclonal antisera against PGC-1.

Transient Transfection and Reporter Assays

NIH 3T3 or Fao hepatoma cells were cultured in 10% FBS-RPMI and transfected at 70-90% confluency using Fugene 6 (Roche). The ratio of DNA:Fugene was 1:2. Culture medium was changed after 24 hours. Cells were collected 48 hours after transfection and β-galactosidase and luciferase assays were performed. Transfections were performed in duplicate and repeated at least twice.

Co-immunoprecipitation Experiments

Flag-tagged PGC-1 and/or pCMV-HNF-4α was transfected into BOSC23 cells using Fugene 6. Whole cell lysates were prepared 48 hours after transfection, incubated with a monoclonal antibody to Flag (Sigma) for 2 hours at 4° C., followed by an overnight incubation with protein A/G Sepharose beads. The immunoprecipitate was washed extensively with lysis buffer, separated by SDS-PAGE, and immunoblotted for PGC-1 and HNF-4α (Santa Cruz).

In Vitro Protein Interaction Assays

GST fusion proteins were produced in *E. coli* and purified on beads containing glutathione. $[^{35}S]$-HNF-4α was produced by TNT reticulocyte lysate in vitro transcription/translation kit (Promega). Approximately 1 mg of fusion protein was mixed with 5 ml of the in vitro translation in a binding buffer containing 20 mM HEPES (pH 7.7), 75 mM KCl, 0.1 mM EDTA, 2.5 mM $MgCl_2$, 0.05% NP40, 2 mM DTT, and 10% glycerol. Binding was performed for 1 h at room temperature, and the beads were then washed four times with the binding buffer and resuspended in SDS-PAGE sample buffer. After electrophoresis, the radiolabeled proteins were detected by autoradiography.

Adenovirus Infusions and Metabolic Measurements

Male Wistar rats (Charles River) were fed with standard laboratory food and weighed 300-350 g at the time of the studies. Animals were anesthetized by injection of 0.1 ml per 100 g body mass of a solution containing 25 mg/ml of xylazine (Phoenix Scientific) and 0.5 mg/ml of acepromazine (Fermenta Animal Health). CMV-GFP and CMV-PGC-1 adenoviruses were purified by CsCl gradient centrifugation as described in Becker, T. et al. (1994) *Methods Cell Biol.* 43:161-189. Pure recombinant virus ($1 \times 10^{12}$ plaque forming units), suspended in 0.5 ml of phosphate buffered saline (PBS), was injected into anesthetized rats through the tail vein. Animals were allowed to recover and were fed standard food ad libitum. Five days after adenovirus infusion, tail vein blood was collected at 14:00 for measurement of glucose concentration, using a β-glucose analyzer (HemoCue AB). After the measurement, animals were sacrificed. Blood samples were collected from the heart, centrifuged at 1300 g for 15 minutes at 4° C. in 15 ml centrifuge tubes containing 50 μl of 0.4 M EDTA, and stored at −20° C. before measurement of insulin concentrations with a rat insulin specific radioimmunoassay kit (Linco Research). Liver samples were collected, snap frozen in liquid nitrogen, and stored at −80° C. Aliquots of frozen liver samples were processed for northern blot or immunoblot analysis.

Example 1

Regulation of PGC-1 Gene Expression in Hepatocytes Coincides with Elevations of Gluconeogenic Hormones In Vivo and In Culture This example describes the regulation of PGC-1 levels by physiological changes in the liver. Male mice were divided into three experimental groups. The first two groups were either allowed free access to food or subjected to a 24 hour fast and sacrificed at the end of 12 hours. The third group was subjected to a 24 hour fast followed by a 24 hour refeeding, and sacrificed. Ten mg of total RNA extracted from pooled liver tissue (n=3 per group) was analyzed by Northern blotting. As expected, an overnight fast induced the expression of messenger RNA for the gluconeogenic proteins PEPCK and glucose-6-phosphatase. HNF-4α, which is known to be involved in the regulation of PEPCK (Hall, R. K. et al. (1995) *Proc. Natl. Acad. Sci. USA* 92:412-416), was also induced. Northern blotting also revealed a 3.7-fold increase in the PGC-1 mRNA in the liver after an overnight fast. All of these inductions were reversed by re-feeding.

The temporal relationship between the induction of mRNAs for PGC-1 and gluconeogenesis was examined by performing a time course of fasting. Male mice were divided into experimental groups of feeding and fasting (during the night), and sacrificed at 2 hours, 5 hours, and 16 hours. Liver RNA was extracted and pooled from 2-3 animals per group and subjected to Northern analysis. An increase in PGC-1 mRNA was first observed after 2 hours and peaked 5 hours after food deprivation. Induction of PEPCK mRNA was also first detected at 2 hours, increasing at 5 and 16 hours. Thus, the induction of PGC-1 mRNA is a relatively early event, consistent with a role in the control of gluconeogenic genes.

In order to determine if PGC-1 can be induced in liver by cAMP, a molecule known to rise in the liver during fasting, PGC-1 expression was examined in primary hepatocytes treated with cAMP. Primary hepatocytes isolated from rats were cultured in serum-free DMEM and treated with 1 mM 8-bromo cAMP, 1 mM dexamethasone, or a combination of both. Total RNA was isolated from cells 6-8 hours after initiation of treatment. Northern analysis revealed that while dexamethasone produced a barely detectable increase in the PGC-1 mRNA, 8-bromo cAMP treatment caused a more substantial elevation in the PGC-1 transcript, and a combination of cAMP and dexamethasone had a markedly greater effect, demonstrating a synergy between these two hormones. These observations mirrored the known effects of these hormones on the hepatic responses to fasting, including gluconeogenesis, raising the possibility that activation of PGC-1 during fasting may contribute to these processes.

Example 2

Hepatic Levels of PGC-1 Gene Expression In Vivo are Elevated in Animal Models of Insulin Deficiency In the opposite situation from fasting, e.g., following a meal, plasma glucagon levels fall precipitously, but the basal levels are still sufficient to maintain a low rate of gluconeogenesis (Shulman, G. I. et al. (1990) *Am. J. Physiol.* 259: E335; Radziuk, J. (1989) *Am. J. Physiol.* 257:E158-169). However, a simultaneous rise in insulin stimulates glycogen synthase and inhibits glycogen phosphorylase, causing the glucose-6-phosphate to be diverted into glycogen instead of being released as glucose. Insulin also opposes the stimulatory effects of glucagon on some gluconeogenic enzymes, such as PEPCK. Thus insulin, the principal hormone of the anabolic state, is an effective suppressor of hepatic glucose output, and therefore whether PGC-1 levels could be regulated by insulin in vivo was determined.

The liver-specific insulin receptor knock-out (LIRKO) mouse is a useful model of insulin resistance in the liver and is associated with severe diabetes and the failure of insulin to suppress hepatic glucose production (Michael, M. D. et al. (2000) *Mol. Cell* 6:87-97). LIRKO mice were previously reported to display increased levels of gluconeogenic enzymes in the liver, in particular PEPCK and glucose-6-phosphatase. Two-month-old female control (lox/lox) or LIRKO mice were subjected to ad libitum feeding, a 24-hour fast, or a 24-hour fast and 24 hours of refeeding. They were then sacrificed and liver tissue was extracted. When liver tissues from these animals were evaluated for PGC-1 expression, a striking elevation in the null animals was consistently detected relative to the lox control animals, correlating well with the elevated levels of gluconeogenic enzymes in these animals. The differences between the knockout and control mice was most apparent in the fed and refed states, although it was still apparent in the fasted state. These data suggest that PGC-1 expression, like gluconeogenesis itself, is suppressed by the action of the insulin receptor.

The levels of PGC-1 in the livers of streptozotocin (STZ)-diabetic mice, which is the most commonly used experimental model of type 1 diabetes (McNeill, J. H., ed. (1999) *Experimental Models of Diabetes*. Boca Raton, Fla.: CRC Press. pp. 3-18), was also examined. Six-to-eight week old male mice received intraperitoneal injections daily with sodium citrate solution (control group) or streptozotocin (100 mg/g of body weight) for three consecutive days. After 10 days, the animals (n=3 per group) were sacrificed.

Northern analysis was performed on total RNA isolated from liver and revealed that PGC-1 was consistently increased in the livers of the STZ-diabetic mice. Because STZ selectively targets the pancreatic P-cells and causes systemic insulinopenia, this result is also consistent with the interpretation that PGC-1 is negatively regulated by insulin in vivo.

Mice homozygous for the obesity (ob) gene are obese, severely insulin resistant, and widely used as a model of type 2 diabetes. Three-month-old male ob/ob or lean littermates fed ad libitum were sacrificed, and RNA was extracted from the liver. PGC-1 mRNA is elevated in the livers of ob/ob mice, as compared with lean controls.

Example 3

Figure 2:
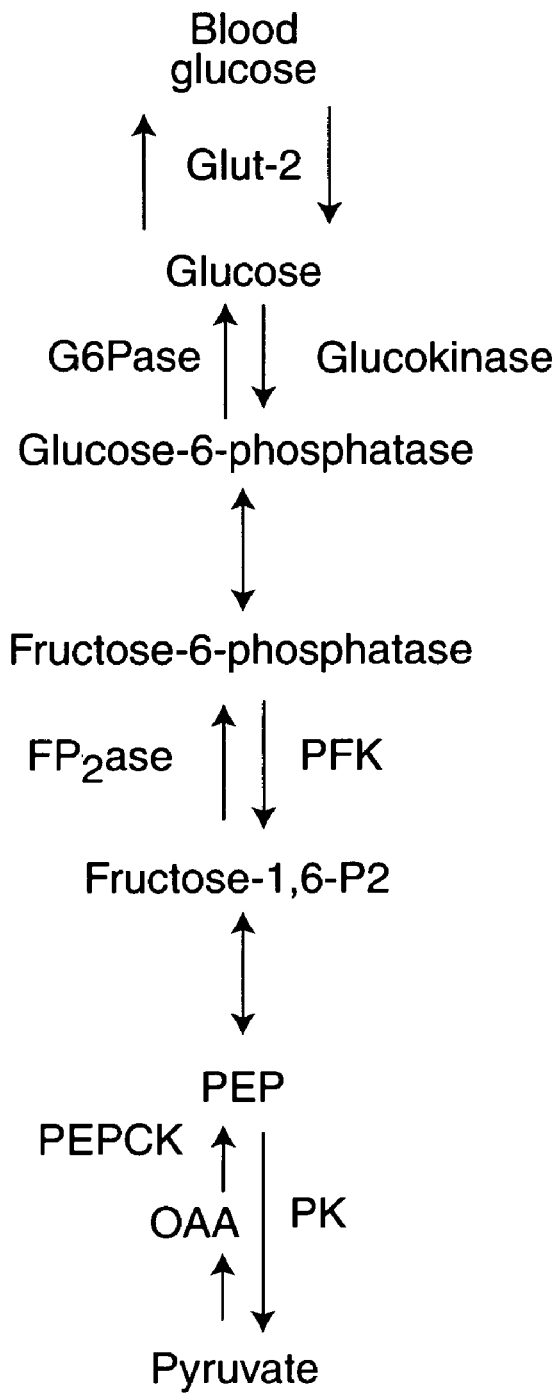
FIG. 2 depicts a schematic diagram of the gluconeogenic pathway. Fructose-1,6-P2=fructose-1,6-bisphosphate. PFK=phosphofructokinase. PEP=phosphoenolpyruvate. OAA=oxaloacetate. PK=pyruvate kinase. PEPCK=phosphoenolpyruvate carboxykinase. FP2ase=fructose-1,6-bisphosphatase.

Expression of PGC-1 Increases Glucose Output from Hepatocytes by Activating Multiple Genes of the Gluconeogenic Pathway To address the possibility that PGC-1 may regulate aspects of hepatic glucose metabolism, PGC-1 was expressed in cultured primary rat hepatocytes using an adenoviral vector. Primary hepatocytes were maintained in 10% FBS-DMEM, and at 48 hours after plating were infected with control adenovirus expressing GFP or an adenoviral vector expressing both GFP and PGC-1 at a multiplicity of infection (MOI) of 30. Primary cells were chosen because they respond well to hormonal stimulation and therefore provide a good model of physiological regulation. This titer was sufficient to achieve over 90% infection rate, as determined by GFP fluorescence. Total RNA was isolated from cells 48 hours after infection and was analyzed by Northern blotting. The Northern analysis revealed that PGC-1 expression markedly increased the levels of several key gluconeogenic enzymes, including PEPCK and glucose-6-phosphatase, which catalyze the first committed step and the terminal step of the gluconeogenic pathway, respectively. Fructose-1,6-bisphosphatase was also elevated several-fold. Together, these three enzymes comprise the three major control points of the gluconeogenic pathway (Nordlie, R. C. et al. (1999) Annu. Rev. Nutr. 19:379-406; Pilkis, S. J. and Granner, D. K. (1992) Annu. Rev. Physiol. 54:885-909; see FIG. 2 for a schematic illustration of the gluconeogenic pathway). Glucocorticoids caused an additional induction of gluconeogenic genes in cells expressing PGC-1.

Primary hepatocytes were then infected with increasing titers of GFP or PGC-1 adenovirus (MOI=0, 5, 10, 30, 60) and the cells were harvested for RNA or protein 48 to 72 hours post infection. Total RNA was probed for the expression of gluconeogenic enzymes (PEPCK and G6 Pase), and total cellular protein was immunoblotted for PGC-1 protein expression. This showed that regulation of gluconeogenic genes was dose-dependent; it was possible to detect a significant increase in the target genes even when the hepatocytes were infected at a relatively low multiplicity of infection (MOI). For example, an MOI of 5 produced a robust increase in the glucose-6-phosphatase transcript, and an MOI of 30 readily elevated the PEPCK levels. Expression of these genes reached a plateau at an MOI of 60. These adenovirus titers resulted in physiological levels of PGC-1 protein; an MOI of 60 resulted in a level of PGC-1 that approaches but does not exceed the level present in fasted liver. Thus, a dose-dependent activation of the hepatic gluconeogenic enzymes was achieved by titrating the amount of the PGC-1 expression in cells. Furthermore, the elevation of PGC-1 stimulated the expression of gluconeogenic genes in the physiological range of this coactivator.

Figure 3:
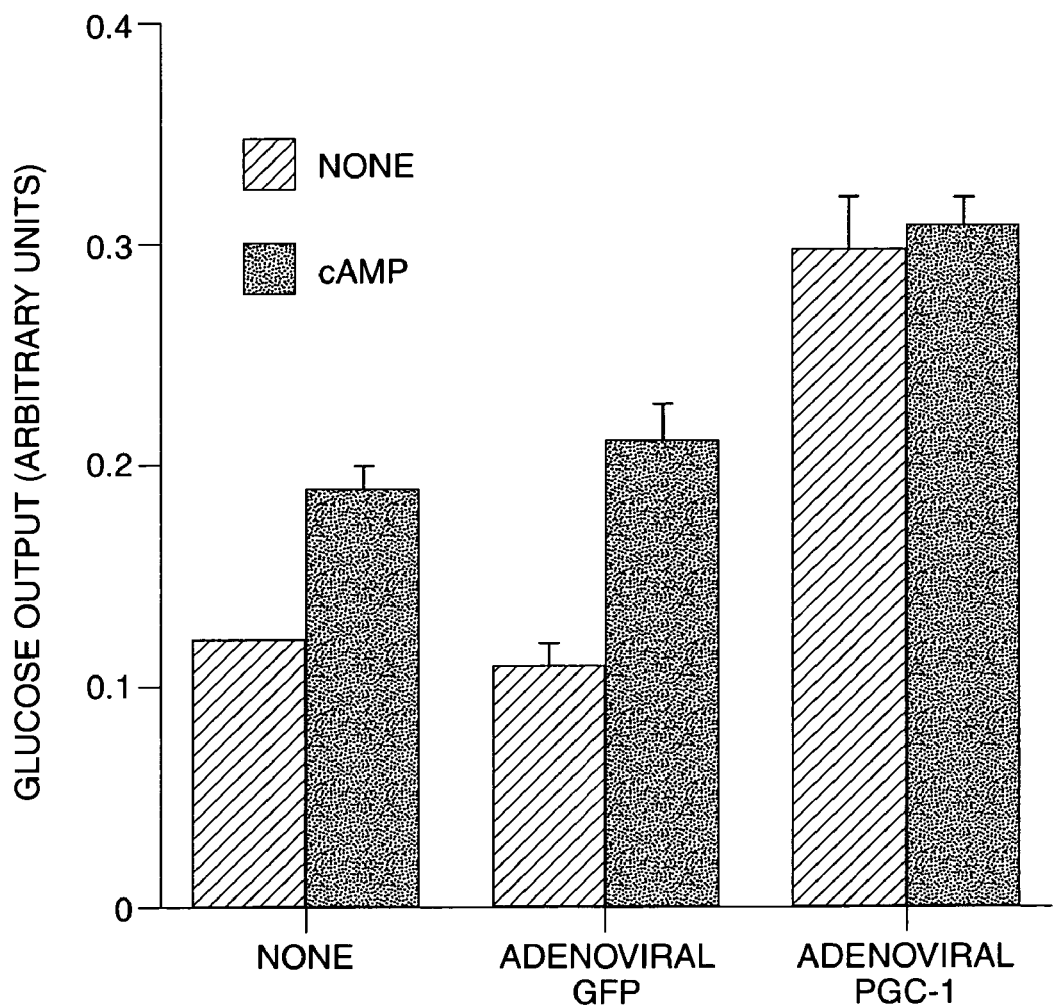
FIG. 3 depicts the results of a glucose production assay in primary hepatocytes infected with adenoviruses expressing either GFP (control) or PGC-1, in the presence or absence of cAMP.

It was next determined whether expression of PGC-1 could enhance the net glucose production by hepatocytes. Primary hepatocytes were infected with GFP or PGC-1 expressing adenovirus and were subsequently cultured in serum-free DMEM with or without 1 mM cAMP treatment. Forty eight hours after infection, cells were washed twice in phosphate-buffered saline and were incubated in glucose production buffer for a 3 hour period, at the end of which the medium was collected for a measurement of the glucose concentration. Measurements of the glucose released into the culture medium, which initially contained gluconeogenic precursors but no glucose, revealed that the overexpression of PGC-1 by itself (MOI of 60) is sufficient to increase the basal glucose production by 3-fold in the absence of any exogenous hormonal stimulation (FIG. 3). In addition, the PGC-1 expression largely blunted the cAMP response (the addition of 8-bromo-cAMP did not further enhance this response), consistent with the induction of PGC-1 as a major component of cAMP action in this process. These data directly demonstrate the ability of PGC-1, at physiological concentrations, to potentiate the hepatic glucose output via transcriptional regulation of the gluconeogenic enzymes.

Example 4

PGC-1 Activates the PEPCK Promoter in Interaction with HNF-4α

To investigate the mechanisms underlying the activation of the gluconeogenic enzymes, PEPCK gene promoter was used. The PEPCK promoter has been extensively studied (Hanson, R. W. and Reshef, L. (1997) Annu. Rev. Biochem. 66:581-611; Pilkis and Granner (1992) supra). Thought by many to catalyze the rate-limiting step of gluconeogenesis, the activity of this enzyme is regulated primarily at the transcriptional level by a number of hormones, including glucagon (via cAMP), glucocorticoids, retinoic acid, thyroid hormone, and insulin. Correspondingly, a number of regulatory elements in the PEPCK promoter that serve as putative transcription factor binding sites have been identified using transient transfection assays in hepatoma cell lines (Hall, R. K. et al. (1995) Proc. Natl. Acad. Sci. USA 92:412-416; Hanson and Reshef (1997) supra; Mitchell J. et al. (1994) Mol. Endocrinol. 8:585-594; Park, E. A. et al. (1999) J. Biol. Chem. 274(1):211-217; Roesler, W. J. et al. (1994) J. Biol. Chem. 269(19):14276-14283; Scott, D. K. et al. (1996) J. Biol. Chem. 271(50):31909-31904; Yeagley, D. et al. (1998) J. Biol. Chem. 273(30):18743-18750). A commonly invoked model based on these functional analyses depicts a set of multiple cis-regulatory elements, termed a hormone response unit, being required for an optimal response to a given hormonal stimulus, with overlaps often seen among different response units. For example, the glucocorticoid response unit contains at least six discrete elements, including two relatively weak glucocorticoid receptor (GR) binding sites (GR1, GR2), a cAMP response element (CRE), and three accessory transcription factor binding sites called AF1, AF2, and AF3; each of the six sites is necessary for a full glucocorticoid response (Sugiyama, T. et al. (2000) J. Biol. Chem. 275(5):3446-3454). AF1 and AF3, however, also belong to the retinoic acid response unit, and AF3 is a part of the thyroid hormone response unit as well. Therefore, there are many opportunities for crosstalk between different hormonal responses, and a regulation under a more physiological context likely involves a complex and coordinated integration of these response units in the face of multiple environmental stimuli.

Figure 4:
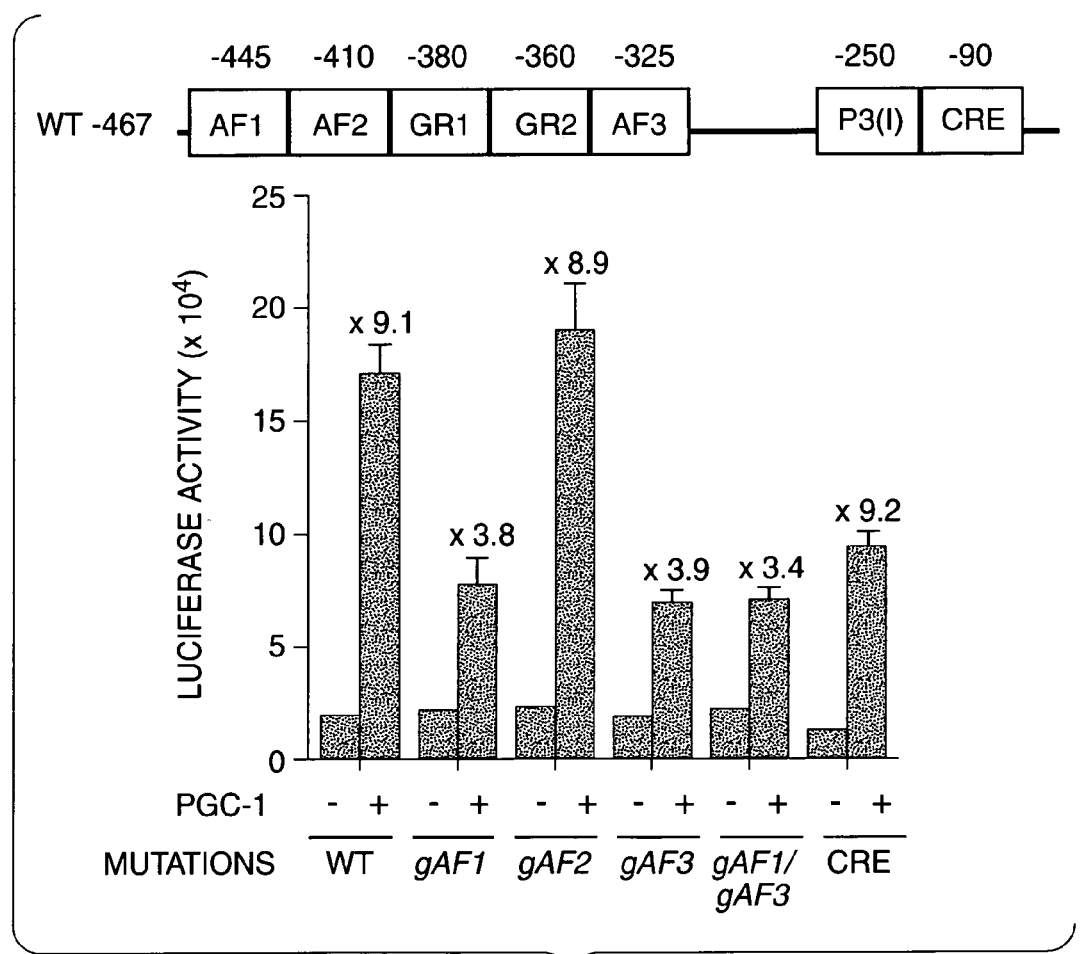
FIG. 4 depicts a comparison of the ability of PGC-1 to activate the wild-type (WT) PEPCK gene promoter and various mutant constructs. The locations within the PEPCK promoter of the various response elements is shown at the top.

The ability of PGC-1 to activate the PEPCK-promoter (using a luciferase reporter gene) in hepatoma cells was examined. Fao rat hepatoma cells were maintained in 10% FBS-RPMI and transfected in a 6 well format with 200 ng of pPL32-PEPCK-luciferase (or pGL3-PEPCK-luciferase), 100 ng CMV β-galactosidase, and 1 mg of pCMV or pCMV-PGC-1 per well. Cells were harvested for luciferase assays 48 hours after transfection, and the readings were normalized by β-galactosidase activity. The Fao cell line is a well-differentiated rat hepatoma cell line that possesses a relatively active gluconeogenic pathway. The 467 base pair fragment of the PEPCK promoter used in the study has been shown to closely mimic the responses of the full-length endogenous PEPCK promoter to various hormones, including cAMP and glucocorticoids. In the transient transfection assays described above, PGC-1 activated the wild-type PEPCK promoter-reporter gene by approximately 10-fold (FIG. 4).

To identify the regulatory elements mediating the effect of PGC-1 on this promoter, mutant constructs were utilized in which various regulatory elements within the PEPCK-luciferase reporter construct were substituted by a yeast Gal4 DNA binding element (FIG. 1; Wang, J. C. et al. (1999) *Mol. Endocrinol.* 13:604-618). As reported previously, mutations in distal sites such as the AF elements did not affect the basal reporter activity. However, mutation of the AF1 or AF3 site (or both) each reduced the PGC-1-mediated activation by 50-60%; a combination of the AF1-to-Gal4 substitution and additional block mutations in the GR binding sites (GR1, GR2) led to a small but significant further decrease. In contrast, a mutation in the AF2 or the CRE site did not produce an appreciable effect on the magnitude of the activation. A replacement of the P3 (I) site, an element shared by the cAMP and thyroid hormone response units, by the Gal4 DNA binding element caused a modest (25%) reduction in the PGC-1 mediated activation of the PEPCK reporter. These results imply that the interactions between PGC-1 and the AF1 and AF3 sites are quantitatively the most important among the regulatory elements tested in this study. Although the AF1 and the AF3 elements are clearly not redundant, the fact that the AF1/AF3 double mutant shows no greater decrease in activity than the single mutants suggests that they mediate functionally overlapping effects. It also appears that there are other unidentified regulatory elements on the PEPCK promoter through which PGC-1 can produce a partial activation.

Figure 5:
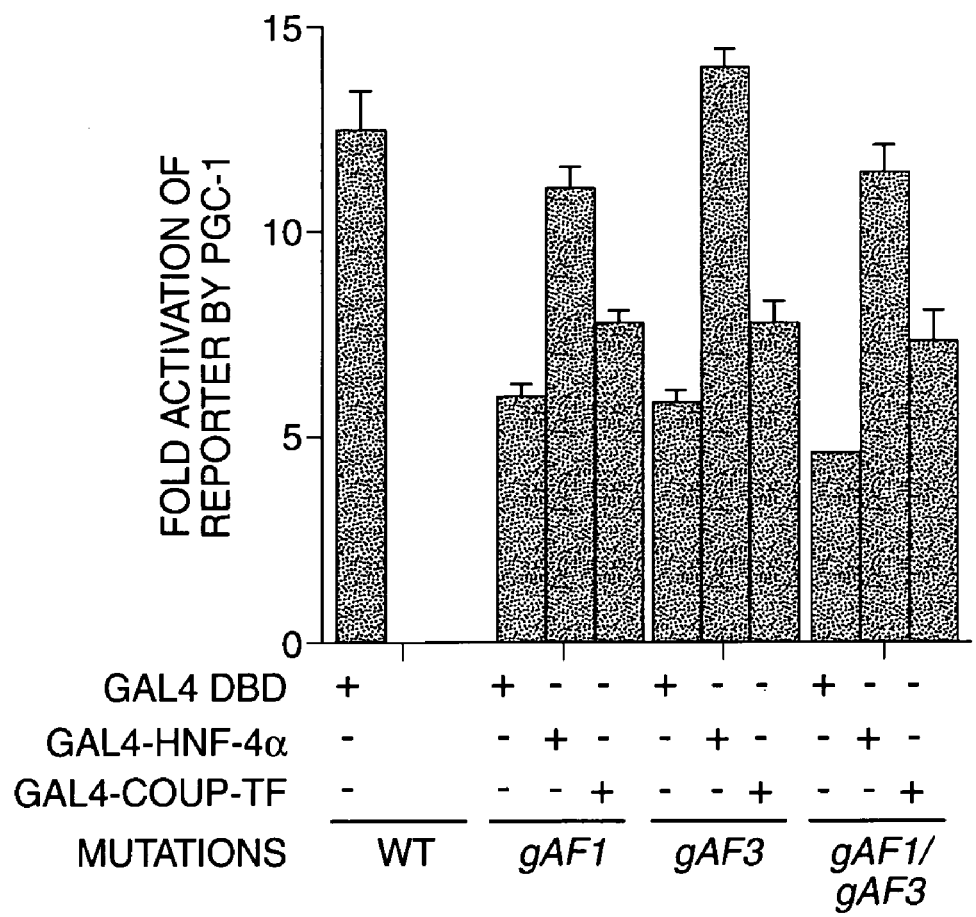
FIG. 5 depicts the restoration of the full PGC-1 activity on the AF1 and AF3 mutant promoters by cotransfection of HNF-4α.

The AF1 and AF3 sites are both DR-1 type sequences that can bind several nuclear receptors. Using hepatocyte extracts, the AF1 element has previously been shown to bind HNF-4α and COUP-TF, both orphan nuclear receptors (Hall et al. (1995) supra; Sugiyama et al. (2000) supra). The AF3 element has also been associated with COUP-TF binding (Scott et al (1996) supra). While the AF3 site has not been associated with HNF-4α binding, PGC-1 is able to coactivate HNF-4α via a multimerized (3×) AF3 element, suggesting that a simultaneous presence of PGC-1 may allow for significant binding to take place. Vectors encoding the Gal4 DBD, Gal4 DBD-HNF-4α, or Gal4 DBD-COUP-TF fusion proteins (500 ng per well) were cotransfected with the mutant receptors, containing a substitution of a particular element within the Gal4 DBD, to determine whether they can rescue the PGC-1 activity. When a Gal4-HNF-4α construct encoding the Gal4 DNA binding domain (DBD) fused to the ligand binding/transactivation domain of HNF-4α was cotransfected with the AF1 or AF3 mutant or the AF1/AF3 double mutant PEPCK constructs, the full PGC-1 activity was restored (FIG. 5). In contrast, cotransfection of a Gal4-COUP-TF construct produced only a partial restoration (approximately 20-30% of that achieved by HNF-4α), and cotransfection of the Gal4 DBD alone had virtually no effect on the PGC-1 mediated activation. Very similar results were obtained at the AF3 site. These data suggest that the coactivation of HNF-4α by PGC-1 via the AF1 element (and probably the AF3) constitutes a major mechanism of control at this promoter.

Figure 6:
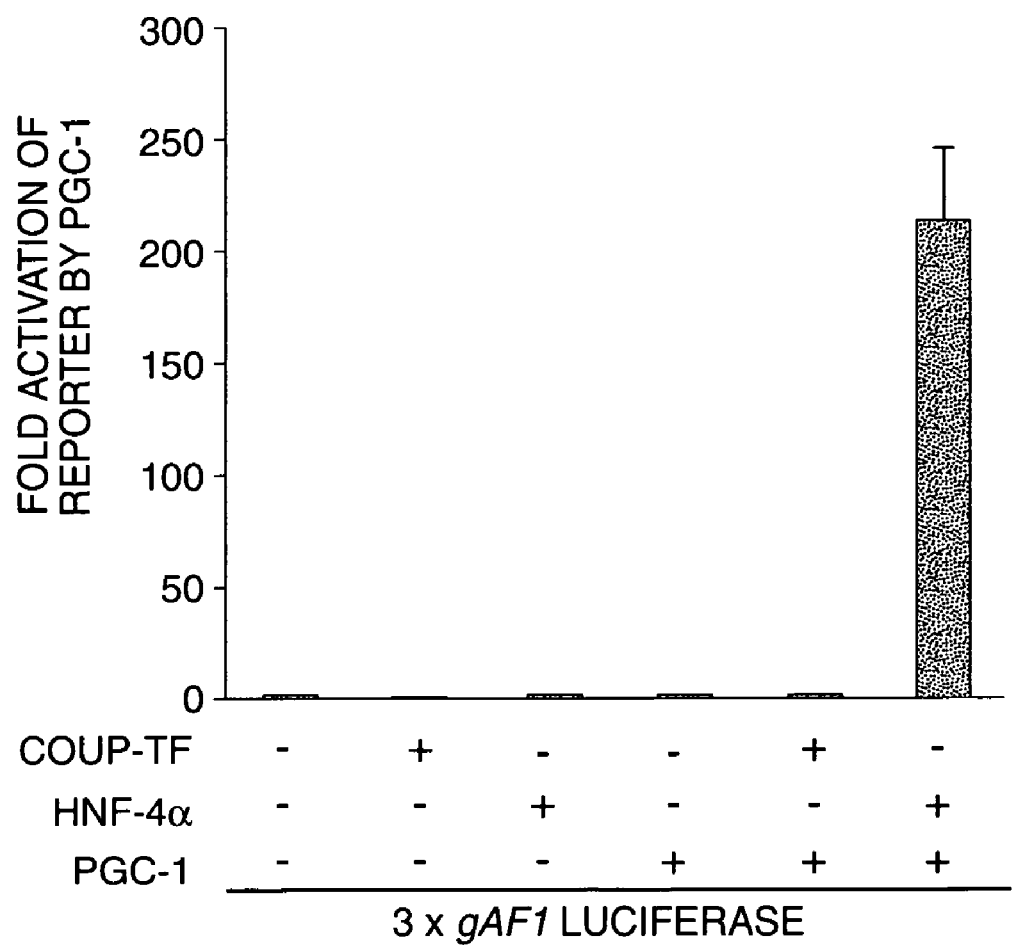
FIG. 6 depicts the strong coactivation of HNF-4α, but not COUP-TF, by PGC-1 on an AF1 multimerized reporter construct.

To examine these functional interactions at the AF1 site with intact transcription factors, reporter gene assays were performed using PGC-1, wild-type HNF-4α and COUP-TF proteins, and a multimerized AF1 response element. To avoid interference with endogenous liver factors, these experiments were done in NIH 3T3 fibroblasts. Transfections were done as described above for FIG. 4. Neither HNF-4α, COUP-TF, nor PGC-1 activates these target sequences alone (FIG. 6). Although PGC-1 has no ability to coactivate COUP-TF, it dramatically coactivates HNF-4α without addition of any hormone or HFN-4 ligand.

Figure 7:
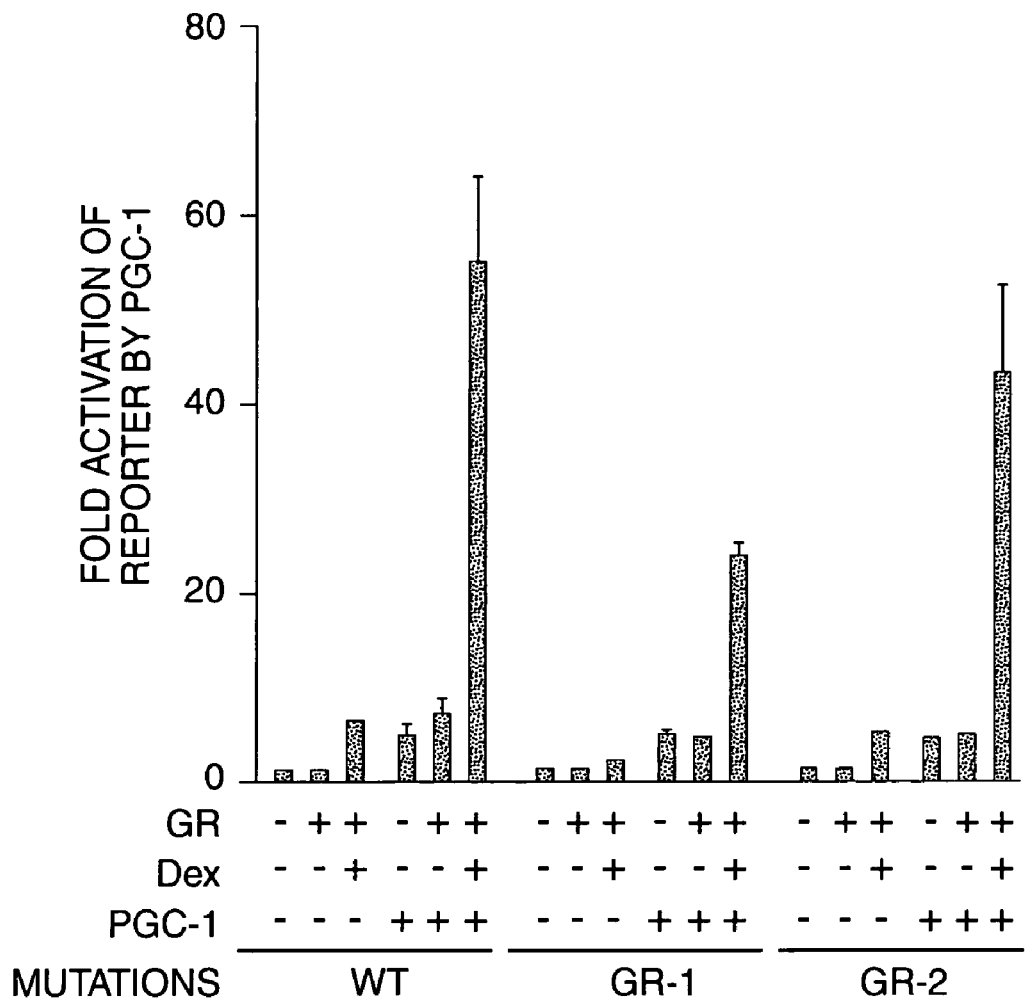
FIG. 7 depicts the coactivation of the glucocorticoid receptor (GR) by PGC-1 on the PEPCK promoter.

The role of the glucocorticoid response elements in the PEPCK promoter was also examined. PGC-1 has been shown to bind to and coactivate the glucocorticoid receptor in a ligand-dependant manner (Knutti, D. et al. (2000) *Mol. Cell. Biol.* 20:2411-2422). Fao hepatoma cells were transfected as described above for FIG. 4. Dexamethasone (dex, 1 µM final concentration) was added for the final 24 hours. PGC-1 coactivates the PEPCK promoter through the glucocorticoid receptor also in a ligand dependant manner (FIG. 7). This effect is substantially reduced by mutation at the glucocorticoid receptor-1 (GR-1) site, but the GR-2 site, consistent with data indicating a more important regulatory role for the GR-1 site (Scott, D. K., et al. (1996) *J. Biol. Chem.* 271:31909-31904).

PEPCK is a tissue-restricted enzyme that catalyzes the first committed step of gluconeogenesis, involving the formation of phosphoenolpyruvate from oxaloacetate. PEPCK is not known to be regulated allosterically or by covalent modification, and its activity is primarily controlled at the transcriptional level by a number of hormones, particularly glucagon (via cAMP). A chemical inhibitor of PEPCK has been reported to produce hypoglycemia in fasted animals (DiTullio, N. W. et al. (1974) *Biochem. J.* 138:387-394), and transgenic mice overexpressing PEPCK display hyperglycemia, hyperinsulinemia, and reduced glucose tolerance, all features resembling type 2 diabetes (Valvera, A., et al. (1994) *Proc. Natl. Acad. Sci. USA* 91:9151-9154). In addition, several animal models of diabetes are associated with significantly elevated levels of PEPCK and concomitantly increased hepatic glucose production, possibly indicative of a defective hormonal regulation of PEPCK expression (Friedman, J. E. et al. (1997) *J. Biol. Chem.* 272(50):31475-31481; Noguchi, T. T. et al. (1993) *FEBS Lett.* 328:145-148; Shafrir, E. (1988) in *Frontiers in diabetes research: Lessons learned from animal diabetes*. (E. Shafrir and A. E. Reynolds, eds) 2nd ed. Pp. 304-315. John Libbey and Co.). There is no known example of genetic mutations in either the PEPCK gene itself or the promoter region associated with documented cases of diabetes, but a clinical syndrome may result from a defect in the function of regulatory protein(s) acting on the promoter or further upstream (e.g., PGC-1).

Because the regulation of the PEPCK gene is of such critical importance in gluconeogenesis and is readily accessible to mechanistic approaches at the promoter level, various mutant alleles of the PEPCK promoter were examined to localize the potential cis-regulatory elements involved in mediating the PGC-1 effect. It was determined that the binding of HNF-4α to the previously identified AF1 and AF3 sites is required for full activation of the PEPCK promoter. HNF-4α is a liver-enriched orphan nuclear receptor better known for its association with maturity onset diabetes of the young (MODY) type 1, which is due to an insulin secretory defect of the pancreatic β cells. In the liver, HNF-4α has been shown to be required for hepatocyte differentiation and regulation of multiple liver-specific genes (Li, J. et al. (2000) *Genes Dev.* 14(4);464-474). Its involvement in hepatic glucose metabolism is underscored by the fact that it serves as an accessory factor in the glucocorticoid-mediated induction of the PEPCK gene by acting through the AF1 site (Hall, R. K. et al. (1995) *Proc. Natl. Acad. Sci. USA* 92:412-416). Its gene expression also coincides with increased gluconeogenesis, being induced by glucocorticoids and glucagon, and repressed by insulin in primary hepatocytes (Oyadomari, S. et al. (2000) *FEBS Lett.* 478:141-146). In addition, HNF-4α levels in the liver were found to be elevated in streptozotocin-induced diabetic rats, with normalization by insulin (Oyadomari et al. (2000) supra). Taken together, these data paint a picture of HNF-4α as a transacting regulatory factor that acts in concert with PGC-1 in the liver to carry out the transcriptional program of gluconeogenesis.

The identification of PGC-1 as a regulator of the PEPCK promoter is significant in the sense that this promoter has up to now been studied mainly in the context of individual regulatory elements. Under physiological conditions, the regulatory elements function in a coordinated fashion to respond to a highly complex and continuously changing hormonal milieu and therefore detailed analyses of individual elements and the bound transcription factors do not necessarily provide information about the interactions between the different elements. A physiologically regulated coactivator such as PGC-1, which can form protein complexes with multiple transcriptional activators, may provide valuable clues on some of the important protein-protein interactions that take place at the promoter.

Another major target of PGC-1 is glucose-6-phosphatase (G6 Pase), also a gluconeogenic enzyme with a limited tissue distribution. In fact, the G6 Pase gene appears to be even more sensitive than PEPCK to PGC-1, as very low titers of PGC-1 can produce a striking elevation in G6 Pase. G6 Pase is thought to be a multisubunit, multifunctional enzyme embedded in the ER membrane and until recently, the lack of information on the enzyme at the molecular level has hampered understanding of its regulation (Nordlie and Foster (1999) supra). The cloning of the catalytic subunit has allowed the identification of cAMP and glucocorticoids as positive regulators of the G6 Pase gene (the catalytic subunit) transcription and insulin as a negative regulator (Argaud, D. et al. (1996) *Diabetes* 45(11):1563-1571). It has been noted that in primary hepatocytes, the stimulatory effect of dexamethasone or cAMP is most readily seen when both hormones are added (Argaud et al. (1996) supra), possibly mirroring the induction of the PGC-1 gene. In primary hepatocytes, overexpression of G6 Pase using adenoviral vectors caused increased rates of gluconeogenesis and glucose-6-phosphate hydrolysis (Seoane, J. K. et al. (1997) *J. Biol. Chem.* 272: 26972-26977) and animals infused with the G6 Pase adenovirus developed hyperglycemia and hyperinsulinemia, and mild glucose intolerance (Trinh, K. et al. (1998) *J. Biol. Chem.* 273:31615-31620). The G6 Pase mRNA and activity in vivo are increased in acute insulinopenic diabetes, which is ameliorated by insulin treatment (Liu, Z. et al. (1994) *Biochem. Biophys. Res. Comm.* 205 (1):680-686).

Multiple lines of evidence therefore indicate that an excessive level of gluconeogenic enzyme(s) such as PEPCK or G6 Pase by itself is sufficient to substantially increase the hepatic gluconeogenic flux and cause systemic hyperglycemia. In parallel with these observations, various animal models of diabetes often display abnormally high levels of these enzymes. The expression of the fructose-1,6-bisphosphatase gene is likewise increased in the livers from fasted and diabetic rats, and insulin treatment decreases the mRNA (El-Maghrabi, M. R. et al. (1991) *J. Biol. Chem.* 266:2115-2120).

Example 5

PGC-1 Coactivates HNF-4α on the G6PASE Promoter

Figure 10:
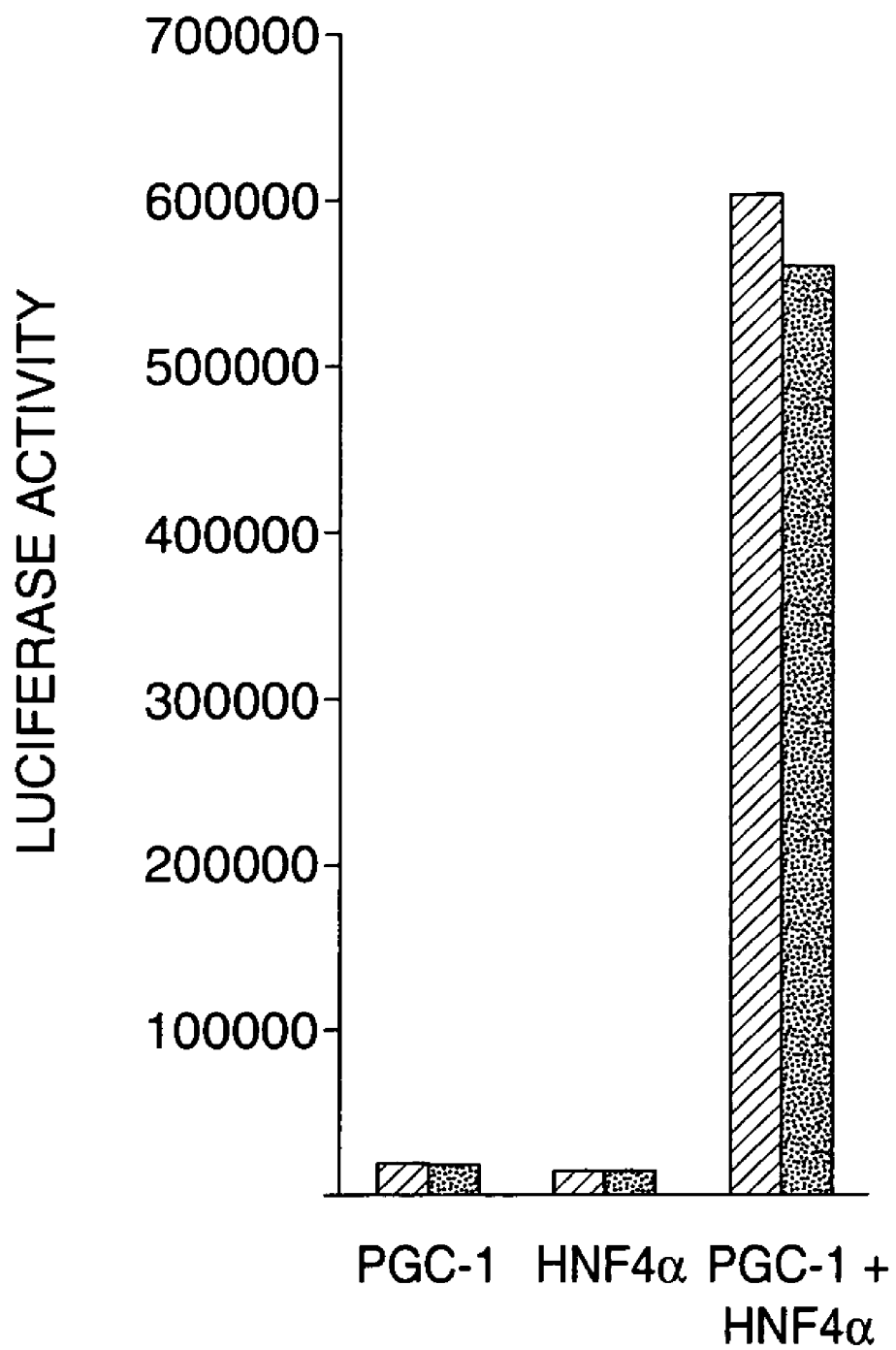
FIG. 10 depicts the ability of PGC-1 to coactivate HNF-4α on the G6 Pase promoter using a luciferase reporter gene. The results of duplicate experiments are shown.

PGC-1 and/or HNF-4α were cotransfected into SV40 transformed hepatocytes, and the ability to coactivate the glucose-6-phosphatase (G6 Pase) promoter was determined using a luciferase reporter gene. Experiments were performed in duplicate. As shown in FIG. 10, transfection of PGC-1 or HNF-4α alone showed no activation of a the G6 Pase promoter-luciferase reporter construct. However, cotransfection of PGC-1 and HNF-4α together resulted in a strong coactivation of the G6 Pase promoter. Gel shift experiments indicated that HNF-4α binds directly to the G6 Pase promoter.

Example 6

Physical Interaction with HNF-4α Requires the LXXLL Motif in the Amino Terminus of PGC-1

To determine whether a direct physical interaction between PGC-1 and HNF-4α might be responsible for the functional interactions described above, co-immunoprecipitation experiments were carried out with whole cell extracts. A Flag-tagged full-length PGC-1 expression construct and a CMV-driven HNF-4α construct were transfected into BOSC23 cells. Whole cell extracts were made 48 hours after transfection, and immunoprecipitates with monoclonal antibodies against the Flag tag were analyzed by protein immunoblotting with polyclonal antisera against PGC-1 or HNF-4α. Immunoprecipates with anti-Flag antibodies contained significant amounts of the HNF-4α protein, as assessed by western analysis, but only when both PGC-1 and HNF-4α were transfected. This indicates that PGC-1 can indeed form a complex with HNF-4α in transfected cells.

A series of in vitro interaction studies was also performed to localize the domains of PGC-1 that are relevant to the HNF-4α interaction. Using an [$^{35}$S]-labeled in vitro translation product of HNF-4α and glutathione S-transferase (GST) fusion proteins of PGC-1, it was determined that the amino-terminal 190 amino acids of PGC-1 (SEQ ID NO:2) are sufficient to mediate a strong interaction with HNF-4α, with a recovery of over 50% of the input. This region has previously been shown to be involved in ligand-dependent interactions with the activation function 2 (AF-2) domains of several nuclear receptors, including estrogen receptor α (ERα), peroxisome proliferator activated receptor α (PPARα), and glucocorticoid receptor (GR) (Tcherepanova, I., P. et al. (2000) *J. Biol. Chem.* 275(21):16302-16308;

Knutti, D. et al. (2000) *Mol. Cell Biol.* 20(7): 2411-2422; Vega, R. B. et al. (2000) *Mol. Cell Biol.* 20(5):1868-1876). In contrast, PGC-1 interacts with PPARγ in a ligand-independent fashion in vitro via PGC-1 amino acid residues 338-403 of PGC-1 (SEQ ID NO:2) (Puigserver, P. et al. (1998) *Cell* 92:829-839).

Because the LXXLL sequence (SEQ ID NO:3) located at amino acid residues 142-146 of PGC-1 (SEQ ID NO:2) had been found to be required for the binding of PGC-1 to ERα and PPARα, a mutant construct of amino acid residues 1-190 of SEQ ID NO:2, in which the LXXLL sequence was mutated by substituting the leucine residue at the fourth position with alanine, was also tested. Radiolabeled HNF-4α protein was produced by in vitro translation with [$^{35}$S]-methionine, and were incubated in a binding buffer with GST control, GST-PGC-1 (amino acids 1-190 and 1-190 with a substitution of Leu$^{145}$ to Ala), or GST-PGC-1 (amino acids 1-400) fusion proteins immobilized on glutathione beads. After extensively washing the beads, the [$^{35}$S]-labeled HNF-4α protein was eluted, separated by SDS-PAGE, and detected by autoradiography. This mutation largely eliminated the binding of PGC-1 to HNF-4α, identifying this motif as a critical mediator of the physical interaction between PGC-1 and HNF-4α. To determine whether the loss of ability of the LXXLL mutant to bind HNF-4α was a specific effect or due to a general loss of proper protein folding, the ability of this mutant to interact with the coactivator SRC-1 was determined. The immunoprecipitation experiments were performed as described above using in vitro translated SRC-1. The ability to interact with SRC-1 is unaltered in this mutant, suggesting that the PGC-1-HNF-4α association is indeed mediated by the LXXLL motif.

Figure 8:
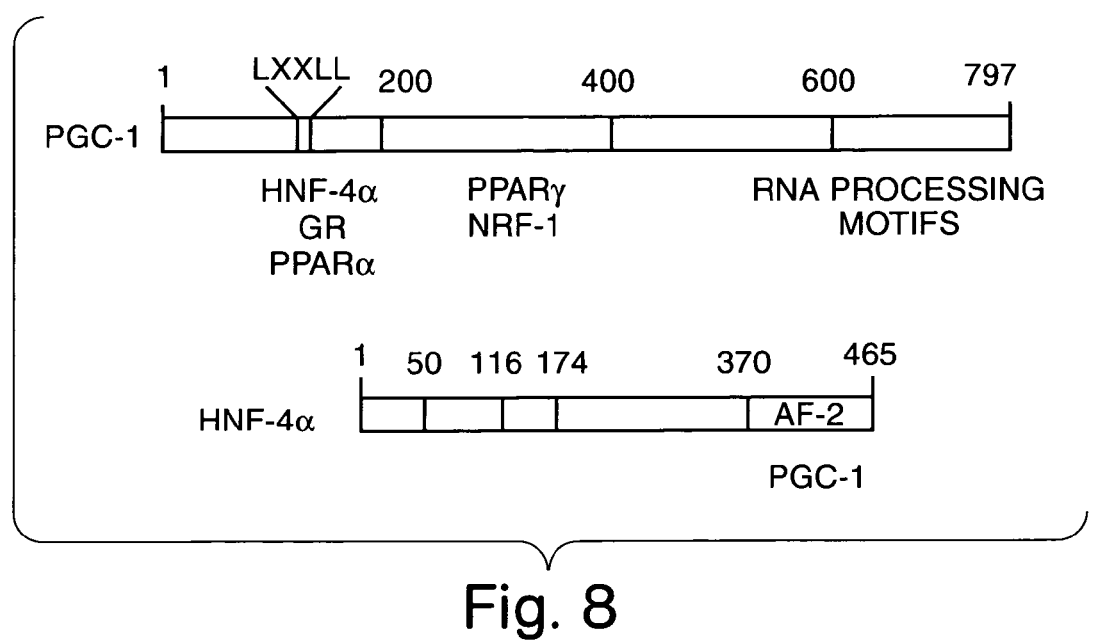
FIG. 8 depicts a schematic representation of the interaction domains in PGC-1 and HNF-4α.

LXXLL motifs in coactivators of nuclear receptors have been shown to interact with the carboxy terminal AF-2 domains on the receptors. A radiolabeled C-terminal-deleted HNF-4α gene (the N terminal 360 amino acid residues) lacking the AF-2 domain expressed HNF-4α with no ability to bind to PGC-1. Thus, these data strongly suggest that the interaction between PGC-1 and HNF-4α is mediated by the LXXLL-AF-2 interaction, an interaction that does not require the addition of exogenous HNF-4α ligand. FIG. 8 depicts a schematic representation of the interaction domains in PGC-1 and HNF-4α.

Interestingly, the LXXLL motif in nuclear coactivators has so far been described only in the context of ligand-dependent interactions with nuclear receptors, because the AF2 domains of receptors require ligand binding to assume the proper conformation needed to interact with the amphipathic α-helices formed from the LXXLL motifs. That HNF-4α is able to interact with the LXXLL motif within the PGC-1 molecule in the absence of exogenous ligands is consistent with the well-documented observation that HNF-4α is able to transactivate in transient transfection assays without added ligands.

Example 7

PGC-1 Stimulation of Gluconeogenesis, but not Ketogenesis or Beta-Oxidation, Requires HNF-4α

The ability of PGC-1 to induce mRNA expression of gluconeogenic, ketogenic, and beta-oxidation genes was examined in cells lacking HNF-4α. Control (floxed) or HNF-4α null cells (primary hepatocytes) were infected with adenoviruses containing GFP (control) or PGC-1 and were either untreated, serum-starved, or treated with dexamethasone and cAMP. PGC-1 induced expression of the ketogenic gene HMG CoA Lyase to similar levels in both the presence and absence of HNF-4α. PGC-1 also induced expression of the beta-oxidation genes carnitine palmitoyl transferase 1 (CPT1) and medium chain fatty acyl CoA dehydrogenase (MCAD) to similar levels in both the presence and absence of HNF-4α. However, PGC-1 was only able to induce the gluconeogenic genes glucose-6-phosphatase and PEPCK in the presence, but not the absence, of HNF-4α, indicating that HNF-4α is required for PGC-1 stimulated gluconeogenesis, but not ketogenesis or beta-oxidation.

Example 8

Insulin Downregulates PGC-1 Medated Gluconeogenesis through FKHR

This example describes experiments designed to determine whether insulin acts directly to suppress PGC-1 expression or function. The levels of PGC-1 mRNA were first examined in cells treated with various combinations of insulin, forskolin, and dexamethasone. While mRNA levels of the gluconeogenic gene G6 Pase was downregulated by insulin treatment, PGC-1 mRNA levels do not change in the presence of insulin treatment. These results indicate that insulin mediated downregulation of gluconeogenesis does not act through downregulation of PGC-1 mRNA.

However, PGC-1 function is negatively regulated by insulin in cultured liver cells. FKHR (also referred to alternatively herein as FOXO1) is a member of the winged-helix transcription factor family, which has been shown to be downstream of the insulin signaling pathway. FKHR is regulated directly by Akt via phosphorylation. Stimulation by insulin results in activation of Akt, which phosphorylates FKHR, which in turn inactivates FKHR by causing it to exit the nucleus. Insulin treatment downregulates the ability of PGC-1 to induce the gluconeogenic genes PEPCK and glucose-6-phosphatase. PGC-1 induced expression of the genes was unchanged when a constitutively active FKHR was used, while a dominant-negative FKHR also downregulates the ability of PGC-1 to induce these genes, even in the absence of insulin.

Figure 11:
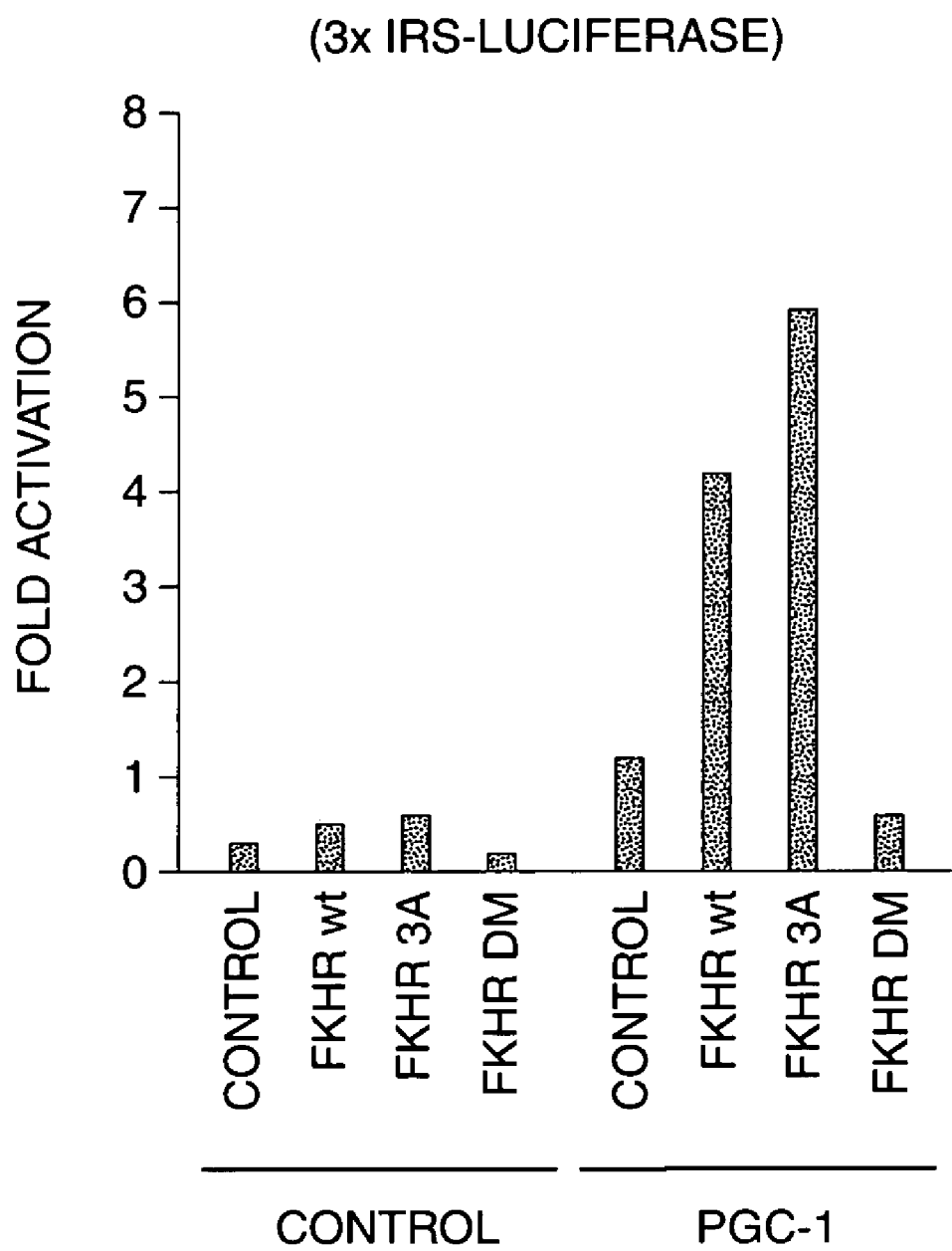
FIG. 11 depicts the ability of PGC-1 to coactivate FKHR on an insulin responsive promoter (3×IRS promoter-luciferase reporter construct). wt=wild type; FKHR 3A=constitutively active mutant of FKHR; FKHR DM=dominant negative mutant of FKHR.

In order to determine whether PGC-1 can coactivate FKHR, PGC-1 was cotransfected with wild-type or mutant forms of FKHR and a 3×IRS (insulin response sequence) promoter-luciferase reporter construct. As shown in FIG. 11, PGC-1 can coactivate FKHR on the insulin responsive promoter. A constitutively active FKHR (three phosphorylatable amino acids changed to alanine) showed increased activation of the reporter. A dominant negative FKHR suppressed all PGC-1 mediated activation of this reporter.

Figure 12A:
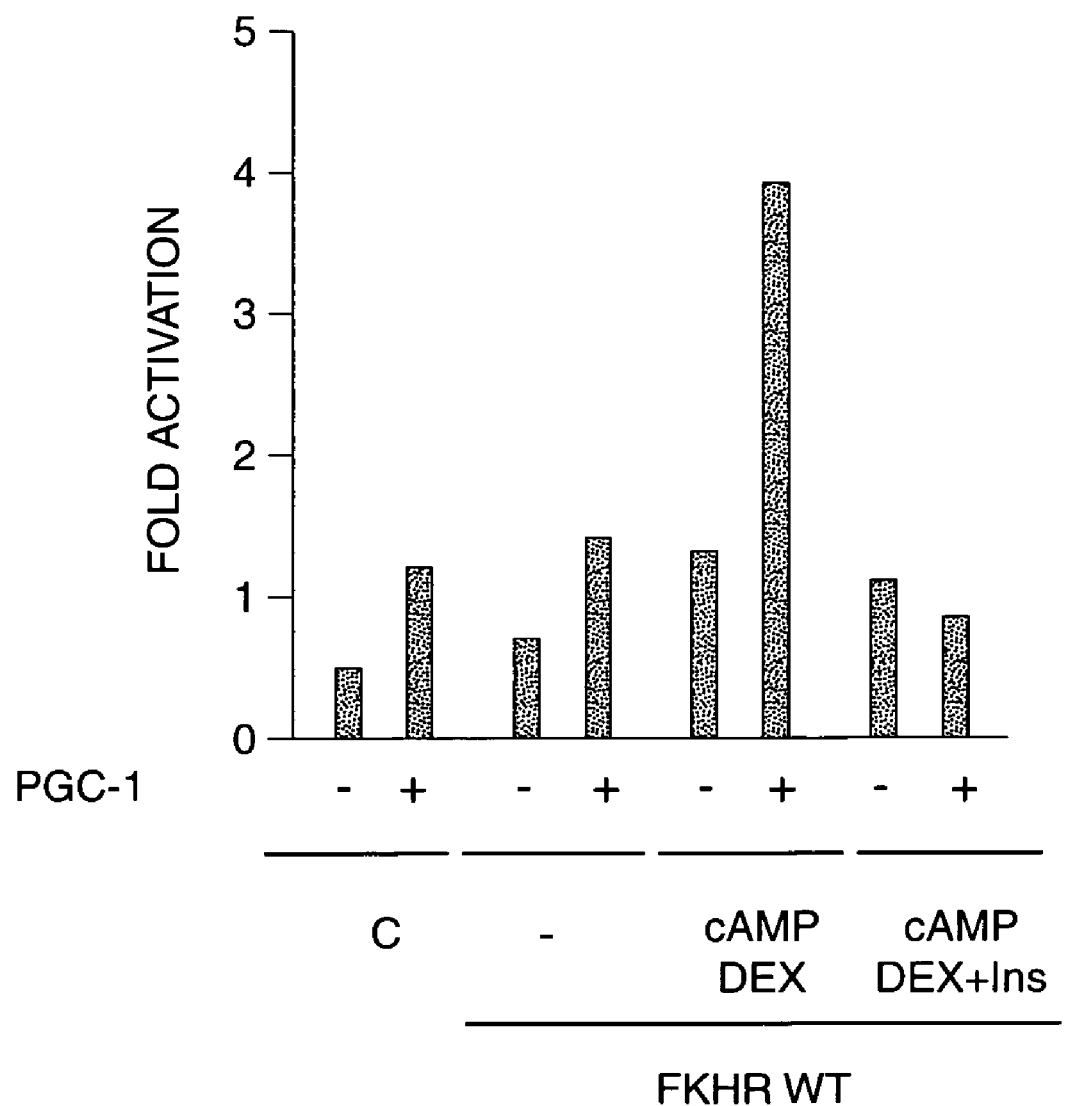
FIGS. 12A-12B depict the ability of PGC-1 to coactivate FKHR on the glucose-6-phosphatase (G6 Pase) promoter.
Figure 12B:
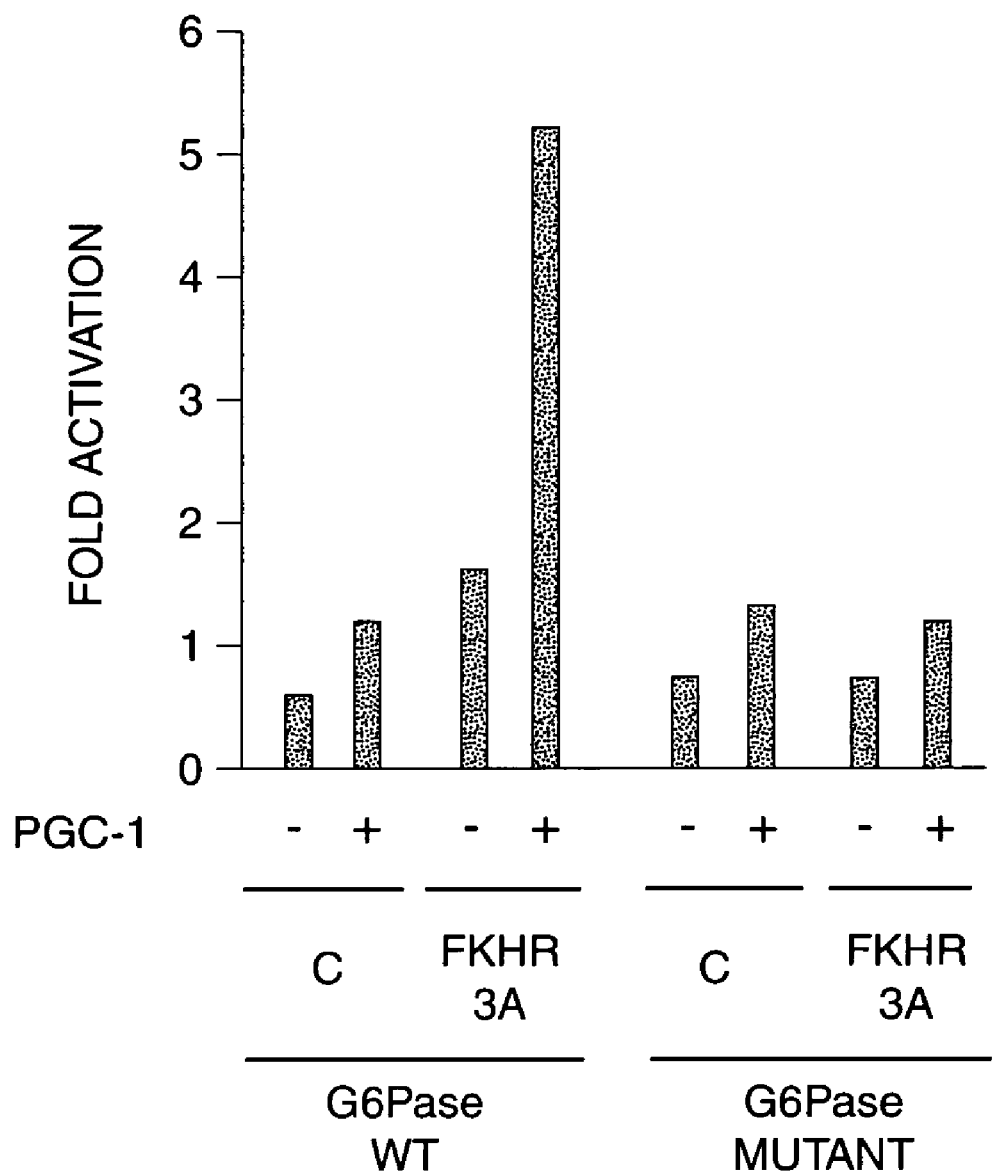

When PGC-1 was cotransfected with wild-type FKHR and a G6 Pase promoter-reporter construct, PGC-1 also coactivated FKHR (FIG. 12A). The constitutively active FKHR further increased the PGC-1 mediated coactivation on the wild type G6 Pase promoter, while no increased coactivation was seen when a mutant G6 Pase promoter (missing the insulin response unit) was used (FIG. 12B).

In vitro interaction experiments demonstrated that PGC-1 and FKHR interact physically through the C-terminal domain of PGC-1. GST fusion constructs of amino acid residues 400-497 of PGC-1 (SEQ ID NO:2), but not residues 1-190 or 200-400, could physically interact with in vitro translated FKHR.

Example 9

PGC-1 Alters Gluconeogenesis In Vivo

Adenoviral vectors were used to examine whether the elevation of PGC-1 levels could activate gluconeogenesis in vivo. Systemic infusion of recombinant adenoviruses into rats through the tail vein has been shown to result primarily in expression in peripheral tissues such as muscle, fat, kidney, or brain (Trinh, K. et al. (1998) *J. Biol. Chem.* 273:31615-31620; O'Doherty, R. M. et al. (1999) *Diabetes* 48:2022-2027). Viruses containing the cDNA encoding PGC-1 (CMV-PGC-1 adenovirus) or green fluorescent protein (CMV-GFP adenovirus) were infused into normal Wistar rats. Five days after virus administration, rats fed ad libitum were sacrificed during the day for collection of liver and blood samples. Assays of blood aspartate aminotransferase activity ensured that there was no hepatotoxicity evident in these experiments. Immunoblot analysis revealed that animals who received the CMV-PGC-1 adenovirus had an average increase in PGC-1 protein of 260% relative to animals infused with CMV-GFP. The PGC-1 level in these fed rats was bout equal to the levels observed in fasted animals.

Figure 9:
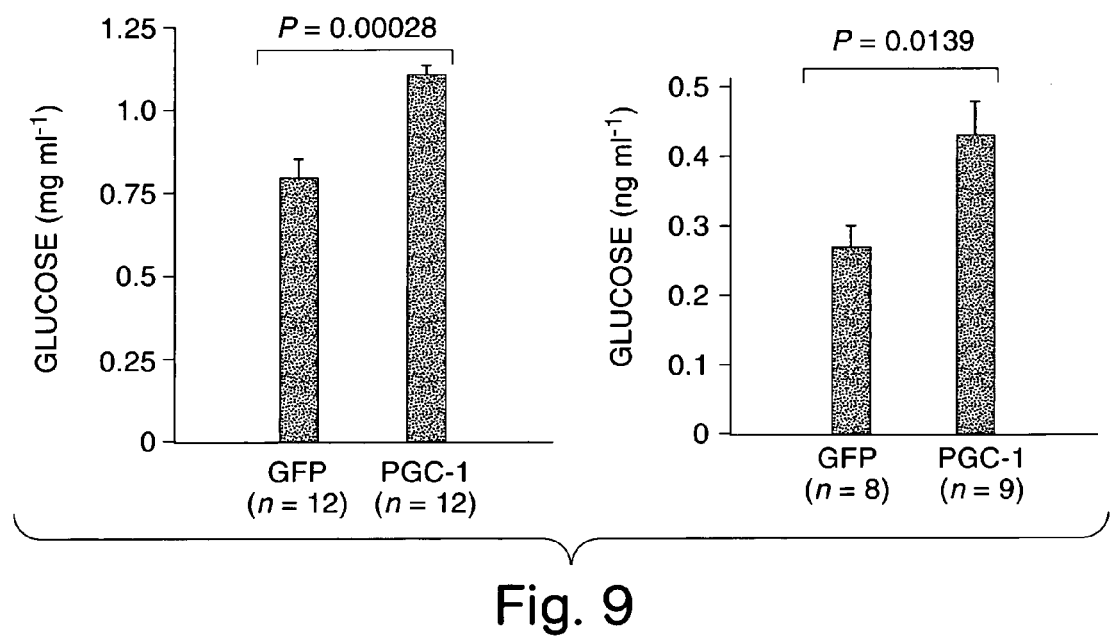
FIG. 9 depicts the activation of glucose production in vivo in rats infected with PGC-1 expressing adenovirus.

CMV-GFP-infused control rats had blood glucose levels of 0.79±0.06 mg/ml (mean±s.d.) and insulin levels of 0.27±0.03 ng/ml. In contrast, rats receiving the CMV-PGC-1 adenovirus had glucose levels of 1.10±0.03 mg/ml, a 39% increase (P=0.00028), and 0.43±0.05 ng/ml of insulin, a 66% increase (P=0.0139) (FIG. 9). Elevated glucose and a compensatory increase of insulin are hallmarks of increased hepatic glucose output in non-diabetic animals; these data closely match what has been observed in overexpression of PEPCK (Valera, A. et al. (1994) *Proc. Natl. Acad. Sci. USA* 91:9151-9154) or the catalytic subunit of glucose-6-phosphatase (Seoane, J. K. et al. (1997) *J. Biol. Chem.* 272: 26972-26977) in the liver of normal rodents by transgenic and adenoviral methods.

To investigate correlative changes in gene expression in the liver, mRNA levels were examined by Northern blotting. The ectopic PGC-1 expression resulted in a dramatic and uniform elevation in mRNA for glucose-6-phosphatase, reaching levels equivalent to those observed in fasting animals. There was also an increased expression of PEPCK mRNA, although one control rat also had elevated PEPCK mRNA. These data together show that modulation of PGC-1 levels in the physiological range promotes expression of gluconeogenic genes and changes in glucose homeostasis.

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed is:

1. A method for identifying a compound capable of modulating gluconeogenesis comprising:
   a) contacting a cell with a compound; and
   b) assaying the ability of the compound to modulate the expression of a PGC-1 nucleic acid molecule by measuring the PGC-1 nucleic acid molecule level or the activity of a PGC-1 polypeptide by measuring the PGC-1 polypeptide level or by measuring the PGC-1 polypeptide activity
      to thereby identify a compound that modulates gluconeogenesis.

2. The method of claim 1, wherein PGC-1 expression or activity is increased.

3. The method of claim 1, wherein PGC-1 expression or activity is decreased.

4. The method of claim 1, wherein PGC-1 expression is measured by Northern blotting, in situ hybridization, enzyme linked immunosorbent assay, Western blotting, immunoprecipitations, or immunofluorescence.

5. The method of claim 1, wherein expression is measured by Northern blotting.

6. The method of claim 1, wherein the cell is a hepatocyte.

7. The method of claim 6, wherein the hepatocyte is selected from the group consisting of a primary hepatocyte and a Fao hepatoma cell.

8. A method for identifying a compound capable of modulating gluconeogenesis comprising:
   a) contacting a cell with a compound; and
   b) assaying the ability of the compound to modulate the expression of a PGC-1 nucleic acid molecule by Northern blotting
      to thereby identify a compound that modulates gluconeogenesis.

* * * * *

SEQUENCE LISTING

```
<160> NUMBER OF SEQ ID NOS: 5

<210> SEQ ID NO 1
<211> LENGTH: 3066
<212> TYPE: DNA
<213> ORGANISM: Mus musculus
<220> FEATURE:
<221> NAME/KEY: CDS
<222> LOCATION: (92)..(2482)

<400> SEQUENCE: 1
aattcggcac gaggttgcct gcatgagtgt gtgctgtgtg tcagagtgga ttggagttga        60
aaaagcttga ctggcgtcat tcgggagctg g atg gct tgg gac atg tgc agc       112
                                   Met Ala Trp Asp Met Cys Ser
                                     1               5 caa gac tct gta tgg agt gac ata gag tgt gct gct ctg gtt ggt gag       160
Gln Asp Ser Val Trp Ser Asp Ile Glu Cys Ala Ala Leu Val Gly Glu
         10                  15                  20 gac cag cct ctt tgc cca gat ctt cct gaa ctt gac ctt tct gaa ctt       208
Asp Gln Pro Leu Cys Pro Asp Leu Pro Glu Leu Asp Leu Ser Glu Leu
     25                  30                  35 gat gtg aat gac ttg gat aca gac agc ttt ctg ggt gga ttg aag tgg       256
Asp Val Asn Asp Leu Asp Thr Asp Ser Phe Leu Gly Gly Leu Lys Trp
 40                  45                  50                  55 tgt agc gac caa tcg gaa atc ata tcc aac cag tac aat aat gag cct       304
Cys Ser Asp Gln Ser Glu Ile Ile Ser Asn Gln Tyr Asn Asn Glu Pro
                 60                  65                  70 gcg aac ata ttt gag aag ata gat gaa gag aat gag gca aac ttg cta       352
Ala Asn Ile Phe Glu Lys Ile Asp Glu Glu Asn Glu Ala Asn Leu Leu
             75                  80                  85 gcg gtc ctc aca gag aca ctg gac agt ctc ccc gtg gat gaa gac gga       400
Ala Val Leu Thr Glu Thr Leu Asp Ser Leu Pro Val Asp Glu Asp Gly
         90                  95                 100
```

-continued

```
           90                  95                 100
ttg ccc tca ttt gat gca ctg aca gat gga gcc gtg acc act gac aac    448
Leu Pro Ser Phe Asp Ala Leu Thr Asp Gly Ala Val Thr Thr Asp Asn
    105                 110                 115 gag gcc agt cct tcc tcc atg cct gac ggc acc cct ccc cct cag gag    496
Glu Ala Ser Pro Ser Ser Met Pro Asp Gly Thr Pro Pro Pro Gln Glu
120                 125                 130                 135 gca gaa gag ccg tct cta ctt aag aag ctc tta ctg gca cca gcc aac    544
Ala Glu Glu Pro Ser Leu Leu Lys Lys Leu Leu Leu Ala Pro Ala Asn
                140                 145                 150 act cag ctc agc tac aat gaa tgc agc ggt ctt agc act cag aac cat    592
Thr Gln Leu Ser Tyr Asn Glu Cys Ser Gly Leu Ser Thr Gln Asn His
                155                 160                 165 gca gca aac cac acc cac agg atc aga aca aac cct gcc att gtt aag    640
Ala Ala Asn His Thr His Arg Ile Arg Thr Asn Pro Ala Ile Val Lys
            170                 175                 180 acc gag aat tca tgg agc aat aaa gcg aag agc att tgt caa cag caa    688
Thr Glu Asn Ser Trp Ser Asn Lys Ala Lys Ser Ile Cys Gln Gln Gln
185                 190                 195 aag cca caa aga cgt ccc tgc tca gag ctt ctc aag tat ctg acc aca    736
Lys Pro Gln Arg Arg Pro Cys Ser Glu Leu Leu Lys Tyr Leu Thr Thr
200                 205                 210                 215 aac gat gac cct cct cac acc aaa ccc aca gaa aac agg aac agc agc    784
Asn Asp Asp Pro Pro His Thr Lys Pro Thr Glu Asn Arg Asn Ser Ser
                220                 225                 230 aga gac aaa tgt gct tcc aaa aag aag tcc cat aca caa ccg cag tcg    832
Arg Asp Lys Cys Ala Ser Lys Lys Lys Ser His Thr Gln Pro Gln Ser
                235                 240                 245 caa cat gct caa gcc aaa cca aca act tta tct ctt cct ctg acc cca    880
Gln His Ala Gln Ala Lys Pro Thr Thr Leu Ser Leu Pro Leu Thr Pro
            250                 255                 260 gag tca cca aat gac ccc aag ggt tcc cca ttt gag aac aag act att    928
Glu Ser Pro Asn Asp Pro Lys Gly Ser Pro Phe Glu Asn Lys Thr Ile
265                 270                 275 gag cga acc tta agt gtg gaa ctc tct gga act gca ggc cta act cct    976
Glu Arg Thr Leu Ser Val Glu Leu Ser Gly Thr Ala Gly Leu Thr Pro
280                 285                 290                 295 ccc aca act cct cct cat aaa gcc aac caa gat aac cct ttc aag gct   1024
Pro Thr Thr Pro Pro His Lys Ala Asn Gln Asp Asn Pro Phe Lys Ala
                300                 305                 310 tcg cca aag ctg aag ccc tct tgc aag acc gtg gtg cca ccg cca acc   1072
Ser Pro Lys Leu Lys Pro Ser Cys Lys Thr Val Val Pro Pro Pro Thr
            315                 320                 325 aag agg gcc cgg tac agt gag tgt tct ggt acc caa ggc agc cac tcc   1120
Lys Arg Ala Arg Tyr Ser Glu Cys Ser Gly Thr Gln Gly Ser His Ser
            330                 335                 340 acc aag aaa ggg ccc gag caa tct gag ttg tac gca caa ctc agc aag   1168
Thr Lys Lys Gly Pro Glu Gln Ser Glu Leu Tyr Ala Gln Leu Ser Lys
345                 350                 355 tcc tca ggg ctc agc cga gga cac gag gaa agg aag act aaa cgg ccc   1216
Ser Ser Gly Leu Ser Arg Gly His Glu Glu Arg Lys Thr Lys Arg Pro
360                 365                 370                 375 agt ctc cgg ctg ttt ggt gac cat gac tac tgt cag tca ctc aat tcc   1264
Ser Leu Arg Leu Phe Gly Asp His Asp Tyr Cys Gln Ser Leu Asn Ser
                380                 385                 390 aaa acg gat ata ctc att aac ata tca cag gag ctc caa gac tct aga   1312
Lys Thr Asp Ile Leu Ile Asn Ile Ser Gln Glu Leu Gln Asp Ser Arg
                395                 400                 405 caa cta gac ttc aaa gat gcc tcc tgt gac tgg cag ggg cac atc tgt   1360
```

-continued

```
              Gln Leu Asp Phe Lys Asp Ala Ser Cys Asp Trp Gln Gly His Ile Cys
                  410                 415                 420 tct tcc aca gat tca ggc cag tgc tac ctg aga gag act ttg gag gcc      1408
Ser Ser Thr Asp Ser Gly Gln Cys Tyr Leu Arg Glu Thr Leu Glu Ala
425                 430                 435 agc aag cag gtc tct cct tgc agc acc aga aaa cag ctc caa gac cag      1456
Ser Lys Gln Val Ser Pro Cys Ser Thr Arg Lys Gln Leu Gln Asp Gln
440                 445                 450                 455 gaa atc cga gcg gag ctg aac aag cac ttc ggt cat ccc tgt caa gct      1504
Glu Ile Arg Ala Glu Leu Asn Lys His Phe Gly His Pro Cys Gln Ala
                460                 465                 470 gtg ttt gac gac aaa tca gac aag acc agt gaa cta agg gat ggc gac      1552
Val Phe Asp Asp Lys Ser Asp Lys Thr Ser Glu Leu Arg Asp Gly Asp
                475                 480                 485 ttc agt aat gaa caa ttc tcc aaa cta cct gtg ttt ata aat tca gga      1600
Phe Ser Asn Glu Gln Phe Ser Lys Leu Pro Val Phe Ile Asn Ser Gly
                490                 495                 500 cta gcc atg gat ggc cta ttt gat gac agt gaa gat gaa agt gat aaa      1648
Leu Ala Met Asp Gly Leu Phe Asp Asp Ser Glu Asp Glu Ser Asp Lys
                505                 510                 515 ctg agc tac cct tgg gat ggc acg cag ccc tat tca ttg ttc gat gtg      1696
Leu Ser Tyr Pro Trp Asp Gly Thr Gln Pro Tyr Ser Leu Phe Asp Val
520                 525                 530                 535 tcg cct tct tgc tct tcc ttt aac tct ccg tgt cga gac tca gtg tca      1744
Ser Pro Ser Cys Ser Ser Phe Asn Ser Pro Cys Arg Asp Ser Val Ser
                540                 545                 550 cca ccg aaa tcc tta ttt tct caa aga ccc caa agg atg cgc tct cgt      1792
Pro Pro Lys Ser Leu Phe Ser Gln Arg Pro Gln Arg Met Arg Ser Arg
                555                 560                 565 tca aga tcc ttt tct cga cac agg tcg tgt tcc cga tca cca tat tcc      1840
Ser Arg Ser Phe Ser Arg His Arg Ser Cys Ser Arg Ser Pro Tyr Ser
                570                 575                 580 agg tca aga tca agg tcc cca ggc agt aga tcc tct tca aga tcc tgt      1888
Arg Ser Arg Ser Arg Ser Pro Gly Ser Arg Ser Ser Ser Arg Ser Cys
585                 590                 595 tac tac tat gaa tca agc cac tac aga cac cgc aca cac cgc aat tct      1936
Tyr Tyr Tyr Glu Ser Ser His Tyr Arg His Arg Thr His Arg Asn Ser
600                 605                 610                 615 ccc ttg tat gtg aga tca cgt tca agg tca ccc tac agc cgt agg ccc      1984
Pro Leu Tyr Val Arg Ser Arg Ser Arg Ser Pro Tyr Ser Arg Arg Pro
                620                 625                 630 agg tac gac agc tat gaa gcc tat gag cac gaa agg ctc aag agg gat      2032
Arg Tyr Asp Ser Tyr Glu Ala Tyr Glu His Glu Arg Leu Lys Arg Asp
                635                 640                 645 gaa tac cgc aaa gag cac gag aag cgg gag tct gaa agg gcc aaa cag      2080
Glu Tyr Arg Lys Glu His Glu Lys Arg Glu Ser Glu Arg Ala Lys Gln
                650                 655                 660 aga gag agg cag aag cag aaa gca att gaa gag cgc cgt gtg att tac      2128
Arg Glu Arg Gln Lys Gln Lys Ala Ile Glu Glu Arg Arg Val Ile Tyr
                665                 670                 675 gtt ggt aaa atc aga cct gac aca acg cgg aca gaa ttg aga gac cgc      2176
Val Gly Lys Ile Arg Pro Asp Thr Thr Arg Thr Glu Leu Arg Asp Arg
680                 685                 690                 695 ttt gaa gtt ttt ggt gaa att gag gaa tgc acc gta aat ctg cgg gat      2224
Phe Glu Val Phe Gly Glu Ile Glu Glu Cys Thr Val Asn Leu Arg Asp
                700                 705                 710 gat gga gac agc tat ggt ttc atc acc tac cgt tac acc tgt gac gct      2272
Asp Gly Asp Ser Tyr Gly Phe Ile Thr Tyr Arg Tyr Thr Cys Asp Ala
                715                 720                 725
```

-continued

| | | |
|---|---|---|
| ttc gct gct ctt gag aat gga tat act tta cgc agg tcg aac gaa act<br>Phe Ala Ala Leu Glu Asn Gly Tyr Thr Leu Arg Arg Ser Asn Glu Thr<br>730                        735                        740 | | 2320 |
| gac ttc gag ctg tac ttt tgt gga cgg aag caa ttt ttc aag tct aac<br>Asp Phe Glu Leu Tyr Phe Cys Gly Arg Lys Gln Phe Phe Lys Ser Asn<br>745                        750                        755 | | 2368 |
| tat gca gac cta gat acc aac tca gac gat ttt gac cct gct tcc acc<br>Tyr Ala Asp Leu Asp Thr Asn Ser Asp Asp Phe Asp Pro Ala Ser Thr<br>760                        765                        770                        775 | | 2416 |
| aag agc aag tat gac tct ctg gat ttt gat agt tta ctg aag gaa gct<br>Lys Ser Lys Tyr Asp Ser Leu Asp Phe Asp Ser Leu Leu Lys Glu Ala<br>                        780                        785                        790 | | 2464 |
| cag aga agc ttg cgc agg taacgtgttc ccaggctgag gaatgacaga<br>Gln Arg Ser Leu Arg Arg<br>795 | | 2512 |
| gagatggtca atacctcatg ggacagcgtg tcctttccca agactcttgc aagtcatact | | 2572 |
| taggaatttc tcctacttta cactctctgt acaaaaataa acaaacaa aacaacaata | | 2632 |
| acaacaacaa caacaacaat aacaacaaca accataccag aacaagaaca acggtttaca | | 2692 |
| tgaacacagc tgctgaagag gcaagagaca gaatgataat ccagtaagca cacgtttatt | | 2752 |
| cacgggtgtc agctttgctt tccctggagg ctcttggtga cagtgtgtgt gcgtgtgtgt | | 2812 |
| gtgtgggtgt gcgtgtgtgt atgtgtgtgt gtgtacttgt ttggaaagta catatgtaca | | 2872 |
| catgtgagga cttgggggca cctgaacaga acgaacaagg gcgacccctt caaatggcag | | 2932 |
| catttccatg aagacacact taaaacctac aacttcaaaa tgttcgtatt ctatacaaaa | | 2992 |
| ggaaaataaa taaatataaa aaaaaaaaaa aaaaactcg agagatctat gaatcgtaga | | 3052 |
| tactgaaaaa cccc | | 3066 |

<210> SEQ ID NO 2
<211> LENGTH: 797
<212> TYPE: PRT
<213> ORGANISM: Mus musculus

<400> SEQUENCE: 2

Met Ala Trp Asp Met Cys Ser Gln Asp Ser Val Trp Ser Asp Ile Glu
1                   5                   10                 15

Cys Ala Ala Leu Val Gly Glu Asp Gln Pro Leu Cys Pro Asp Leu Pro
                 20                   25                   30

Glu Leu Asp Leu Ser Glu Leu Asp Val Asn Asp Leu Asp Thr Asp Ser
                 35                   40                   45

Phe Leu Gly Gly Leu Lys Trp Cys Ser Asp Gln Ser Glu Ile Ile Ser
    50                   55                   60

Asn Gln Tyr Asn Asn Glu Pro Ala Asn Ile Phe Glu Lys Ile Asp Glu
65                  70                   75                   80

Glu Asn Glu Ala Asn Leu Leu Ala Val Leu Thr Glu Thr Leu Asp Ser
                 85                   90                   95

Leu Pro Val Asp Glu Asp Gly Leu Pro Ser Phe Asp Ala Leu Thr Asp
                   100                105              110

Gly Ala Val Thr Thr Asp Asn Glu Ala Ser Pro Ser Ser Met Pro Asp
               115                120              125

Gly Thr Pro Pro Pro Gln Glu Ala Glu Glu Pro Ser Leu Leu Lys Lys
         130                135              140

Leu Leu Leu Ala Pro Ala Asn Thr Gln Leu Ser Tyr Asn Glu Cys Ser
145                150                155              160

Gly Leu Ser Thr Gln Asn His Ala Ala Asn His Thr His Arg Ile Arg

-continued

```
                165                 170                 175
Thr Asn Pro Ala Ile Val Lys Thr Glu Asn Ser Trp Ser Asn Lys Ala
            180                 185                 190
Lys Ser Ile Cys Gln Gln Gln Lys Pro Gln Arg Arg Pro Cys Ser Glu
            195                 200                 205
Leu Leu Lys Tyr Leu Thr Thr Asn Asp Asp Pro Pro His Thr Lys Pro
            210                 215                 220
Thr Glu Asn Arg Asn Ser Ser Arg Asp Lys Cys Ala Ser Lys Lys Lys
225                 230                 235                 240
Ser His Thr Gln Pro Gln Ser Gln His Ala Gln Ala Lys Pro Thr Thr
            245                 250                 255
Leu Ser Leu Pro Leu Thr Pro Glu Ser Pro Asn Asp Pro Lys Gly Ser
            260                 265                 270
Pro Phe Glu Asn Lys Thr Ile Glu Arg Thr Leu Ser Val Glu Leu Ser
            275                 280                 285
Gly Thr Ala Gly Leu Thr Pro Pro Thr Thr Pro His Lys Ala Asn
            290                 295                 300
Gln Asp Asn Pro Phe Lys Ala Ser Pro Lys Leu Lys Pro Ser Cys Lys
305                 310                 315                 320
Thr Val Val Pro Pro Thr Lys Arg Ala Arg Tyr Ser Glu Cys Ser
            325                 330                 335
Gly Thr Gln Gly Ser His Ser Thr Lys Lys Gly Pro Glu Gln Ser Glu
            340                 345                 350
Leu Tyr Ala Gln Leu Ser Lys Ser Ser Gly Leu Ser Arg Gly His Glu
            355                 360                 365
Glu Arg Lys Thr Lys Arg Pro Ser Leu Arg Leu Phe Gly Asp His Asp
            370                 375                 380
Tyr Cys Gln Ser Leu Asn Ser Lys Thr Asp Ile Leu Ile Asn Ile Ser
385                 390                 395                 400
Gln Glu Leu Gln Asp Ser Arg Gln Leu Asp Phe Lys Asp Ala Ser Cys
            405                 410                 415
Asp Trp Gln Gly His Ile Cys Ser Ser Thr Asp Ser Gly Gln Cys Tyr
            420                 425                 430
Leu Arg Glu Thr Leu Glu Ala Ser Lys Gln Val Ser Pro Cys Ser Thr
            435                 440                 445
Arg Lys Gln Leu Gln Asp Gln Glu Ile Arg Ala Glu Leu Asn Lys His
            450                 455                 460
Phe Gly His Pro Cys Gln Ala Val Phe Asp Asp Lys Ser Asp Lys Thr
465                 470                 475                 480
Ser Glu Leu Arg Asp Gly Asp Phe Ser Asn Glu Gln Phe Ser Lys Leu
            485                 490                 495
Pro Val Phe Ile Asn Ser Gly Leu Ala Met Asp Gly Leu Phe Asp Asp
            500                 505                 510
Ser Glu Asp Glu Ser Asp Lys Leu Ser Tyr Pro Trp Asp Gly Thr Gln
            515                 520                 525
Pro Tyr Ser Leu Phe Asp Val Ser Pro Ser Cys Ser Ser Phe Asn Ser
            530                 535                 540
Pro Cys Arg Asp Ser Val Ser Pro Lys Ser Leu Phe Ser Gln Arg
545                 550                 555                 560
Pro Gln Arg Met Arg Ser Arg Ser Arg Ser Phe Ser Arg His Arg Ser
            565                 570                 575
Cys Ser Arg Ser Pro Tyr Ser Arg Ser Arg Ser Arg Ser Pro Gly Ser
            580                 585                 590
```

-continued

```
Arg Ser Ser Ser Arg Ser Cys Tyr Tyr Tyr Glu Ser Ser His Tyr Arg
        595                 600                 605

His Arg Thr His Arg Asn Ser Pro Leu Tyr Val Arg Ser Arg Ser Arg
    610                 615                 620

Ser Pro Tyr Ser Arg Arg Pro Arg Tyr Asp Ser Tyr Glu Ala Tyr Glu
625                 630                 635                 640

His Glu Arg Leu Lys Arg Asp Glu Tyr Arg Lys Glu His Glu Lys Arg
            645                 650                 655

Glu Ser Glu Arg Ala Lys Gln Arg Glu Arg Gln Lys Gln Lys Ala Ile
        660                 665                 670

Glu Glu Arg Arg Val Ile Tyr Val Gly Lys Ile Arg Pro Asp Thr Thr
    675                 680                 685

Arg Thr Glu Leu Arg Asp Arg Phe Glu Val Phe Gly Glu Ile Glu Glu
    690                 695                 700

Cys Thr Val Asn Leu Arg Asp Asp Gly Asp Ser Tyr Gly Phe Ile Thr
705                 710                 715                 720

Tyr Arg Tyr Thr Cys Asp Ala Phe Ala Ala Leu Glu Asn Gly Tyr Thr
            725                 730                 735

Leu Arg Arg Ser Asn Glu Thr Asp Phe Glu Leu Tyr Phe Cys Gly Arg
        740                 745                 750

Lys Gln Phe Phe Lys Ser Asn Tyr Ala Asp Leu Asp Thr Asn Ser Asp
        755                 760                 765

Asp Phe Asp Pro Ala Ser Thr Lys Ser Lys Tyr Asp Ser Leu Asp Phe
770                 775                 780

Asp Ser Leu Leu Lys Glu Ala Gln Arg Ser Leu Arg Arg
785                 790                 795

<210> SEQ ID NO 3
<211> LENGTH: 5
<212> TYPE: PRT
<213> ORGANISM: Mus musculus
<220> FEATURE:
<221> NAME/KEY: VARIANT
<222> LOCATION: 2, 3
<223> OTHER INFORMATION: Xaa = Any Amino Acid

<400> SEQUENCE: 3

Leu Xaa Xaa Leu Leu
  1               5

<210> SEQ ID NO 4
<211> LENGTH: 3023
<212> TYPE: DNA
<213> ORGANISM: Homo sapiens
<220> FEATURE:
<221> NAME/KEY: CDS
<222> LOCATION: (89)..(2482)

<400> SEQUENCE: 4
caggtggctg gttgcctgca tgagtgtgtg ctctgtgtca ctgtggattg gagttgaaaa      60
agcttgactg gcgtcattca ggagctgg atg gcg tgg gac atg tgc aac cag        112
                              Met Ala Trp Asp Met Cys Asn Gln
                                1               5 gac tct gag tct gta tgg agt gac atc gag tgt gct gct ctg gtt ggt       160
Asp Ser Glu Ser Val Trp Ser Asp Ile Glu Cys Ala Ala Leu Val Gly
 10                  15                  20 gaa gac cag cct ctt tgc cca gat ctt cct gaa ctt gat ctt tct gaa       208
Glu Asp Gln Pro Leu Cys Pro Asp Leu Pro Glu Leu Asp Leu Ser Glu
 25                  30                  35                  40
```

-continued

| | |
|---|---|
| cta gat gtg aac gac ttg gat aca gac agc ttt ctg ggt gga ctc aag<br>Leu Asp Val Asn Asp Leu Asp Thr Asp Ser Phe Leu Gly Gly Leu Lys<br>45                  50                      55 | 256 |
| tgg tgc agt gac caa tca gaa ata ata tcc aat cag tac aac aat gag<br>Trp Cys Ser Asp Gln Ser Glu Ile Ile Ser Asn Gln Tyr Asn Asn Glu<br>        60                      65                      70 | 304 |
| cct tca aac ata ttt gag aag ata gat gaa gag aat gag gca aac ttg<br>Pro Ser Asn Ile Phe Glu Lys Ile Asp Glu Glu Asn Glu Ala Asn Leu<br>75                      80                      85 | 352 |
| cta gca gtc ctc aca gag aca cta gac agt ctc cct gtg gat gaa gac<br>Leu Ala Val Leu Thr Glu Thr Leu Asp Ser Leu Pro Val Asp Glu Asp<br>        90                      95                     100 | 400 |
| gga ttg ccc tca ttt gat gcg ctg aca gat gga gac gtg acc act gac<br>Gly Leu Pro Ser Phe Asp Ala Leu Thr Asp Gly Asp Val Thr Thr Asp<br>105                     110                     115                     120 | 448 |
| aat gag gct agt cct tcc tcc atg cct gac ggc acc cct cca ccc cag<br>Asn Glu Ala Ser Pro Ser Ser Met Pro Asp Gly Thr Pro Pro Pro Gln<br>        125                     130                     135 | 496 |
| gag gca gaa gag ccg tct cta ctt aag aag ctc tta ctg gca cca gcc<br>Glu Ala Glu Glu Pro Ser Leu Leu Lys Lys Leu Leu Leu Ala Pro Ala<br>            140                     145                     150 | 544 |
| aac act cag cta agt tat aat gaa tgc agt ggt ctc agt acc cag aac<br>Asn Thr Gln Leu Ser Tyr Asn Glu Cys Ser Gly Leu Ser Thr Gln Asn<br>            155                     160                     165 | 592 |
| cat gca aat cac aat cac agg atc aga aca aac cct gca att gtt aag<br>His Ala Asn His Asn His Arg Ile Arg Thr Asn Pro Ala Ile Val Lys<br>170                     175                     180 | 640 |
| act gag aat tca tgg agc aat aaa gcg aag agt att tgt caa cag caa<br>Thr Glu Asn Ser Trp Ser Asn Lys Ala Lys Ser Ile Cys Gln Gln Gln<br>185                     190                     195                     200 | 688 |
| aag cca caa aga cgt ccc tgc tcg gag ctt ctc aaa tat ctg acc aca<br>Lys Pro Gln Arg Arg Pro Cys Ser Glu Leu Leu Lys Tyr Leu Thr Thr<br>            205                     210                     215 | 736 |
| aac gat gac cct cct cac acc aaa ccc aca gag aac aga aac agc agc<br>Asn Asp Asp Pro Pro His Thr Lys Pro Thr Glu Asn Arg Asn Ser Ser<br>            220                     225                     230 | 784 |
| aga gac aaa tgc acc tcc aaa aag aag tcc cac aca cag tcg cag tca<br>Arg Asp Lys Cys Thr Ser Lys Lys Lys Ser His Thr Gln Ser Gln Ser<br>        235                     240                     245 | 832 |
| caa cac tta caa gcc aaa cca aca act tta tct ctt cct ctg acc cca<br>Gln His Leu Gln Ala Lys Pro Thr Thr Leu Ser Leu Pro Leu Thr Pro<br>250                     255                     260 | 880 |
| gag tca cca aat gac ccc aag ggt tcc cca ttt gag aac aag act att<br>Glu Ser Pro Asn Asp Pro Lys Gly Ser Pro Phe Glu Asn Lys Thr Ile<br>265                     270                     275                     280 | 928 |
| gaa cgc acc tta agt gtg gaa ctc tct gga act gca ggc cta act cca<br>Glu Arg Thr Leu Ser Val Glu Leu Ser Gly Thr Ala Gly Leu Thr Pro<br>            285                     290                     295 | 976 |
| ccc acc act cct cct cat aaa gcc aac caa gat aac cct ttt agg gct<br>Pro Thr Thr Pro Pro His Lys Ala Asn Gln Asp Asn Pro Phe Arg Ala<br>            300                     305                     310 | 1024 |
| tct cca aag ctg aag tcc tct tgc aag act gtg gtg cca cca cca tca<br>Ser Pro Lys Leu Lys Ser Ser Cys Lys Thr Val Val Pro Pro Pro Ser<br>        315                     320                     325 | 1072 |
| aag aag ccc agg tac agt gag tct tct ggt aca caa ggc aat aac tcc<br>Lys Lys Pro Arg Tyr Ser Glu Ser Ser Gly Thr Gln Gly Asn Asn Ser<br>330                     335                     340 | 1120 |
| acc aag aaa ggg ccg gag caa tcc gag ttg tat gca caa ctc agc aag<br>Thr Lys Lys Gly Pro Glu Gln Ser Glu Leu Tyr Ala Gln Leu Ser Lys | 1168 |

```
                        -continued
345                 350                 355                 360
tcc tca gtc ctc act ggt gga cac gag gaa agg aag acc aag cgg ccc      1216
Ser Ser Val Leu Thr Gly Gly His Glu Glu Arg Lys Thr Lys Arg Pro
                    365                 370                 375 agt ctg cgg ctg ttt ggt gac cat gac tat tgc cag tca att aat tcc      1264
Ser Leu Arg Leu Phe Gly Asp His Asp Tyr Cys Gln Ser Ile Asn Ser
                380                 385                 390 aaa acg gaa ata ctc att aat ata tca cag gag ctc caa gac tct aga      1312
Lys Thr Glu Ile Leu Ile Asn Ile Ser Gln Glu Leu Gln Asp Ser Arg
            395                 400                 405 caa cta gaa aat aaa gat gtc tcc tct gat tgg cag ggg cag att tgt      1360
Gln Leu Glu Asn Lys Asp Val Ser Ser Asp Trp Gln Gly Gln Ile Cys
        410                 415                 420 tct tcc aca gat tca gac cag tgc tac ctg aga gag act ttg gag gca      1408
Ser Ser Thr Asp Ser Asp Gln Cys Tyr Leu Arg Glu Thr Leu Glu Ala
425                 430                 435                 440 agc aag cag gtc tct cct tgc agc aca aga aaa cag ctc caa gac cag      1456
Ser Lys Gln Val Ser Pro Cys Ser Thr Arg Lys Gln Leu Gln Asp Gln
                    445                 450                 455 gaa atc cga gcc gag ctg aac aag cac ttc ggt cat ccc agt caa gct      1504
Glu Ile Arg Ala Glu Leu Asn Lys His Phe Gly His Pro Ser Gln Ala
                460                 465                 470 gtt ttt gac gac gaa gca gac aag acc ggt gaa ctg agg gac agt gat      1552
Val Phe Asp Asp Glu Ala Asp Lys Thr Gly Glu Leu Arg Asp Ser Asp
            475                 480                 485 ttc agt aat gaa caa ttc tcc aaa cta cct atg ttt ata aat tca gga      1600
Phe Ser Asn Glu Gln Phe Ser Lys Leu Pro Met Phe Ile Asn Ser Gly
        490                 495                 500 cta gcc atg gat ggc ctg ttt gat gac agc gaa gat aaa agt gat aaa      1648
Leu Ala Met Asp Gly Leu Phe Asp Asp Ser Glu Asp Lys Ser Asp Lys
505                 510                 515                 520 ctg agc tac cct tgg gat ggc acg caa tcc tat tca ttg ttc aat gtg      1696
Leu Ser Tyr Pro Trp Asp Gly Thr Gln Ser Tyr Ser Leu Phe Asn Val
                    525                 530                 535 tct cct tct tgt tct tct ttt aac tct cca tgt aga gat tct gtg tca      1744
Ser Pro Ser Cys Ser Ser Phe Asn Ser Pro Cys Arg Asp Ser Val Ser
                540                 545                 550 cca ccc aaa tcc tta ttt tct caa aga ccc caa agg atg cgc tct cgt      1792
Pro Pro Lys Ser Leu Phe Ser Gln Arg Pro Gln Arg Met Arg Ser Arg
            555                 560                 565 tca agg tcc ttt tct cga cac agg tcg tgt tcc cga tca cca tat tcc      1840
Ser Arg Ser Phe Ser Arg His Arg Ser Cys Ser Arg Ser Pro Tyr Ser
        570                 575                 580 agg tca aga tca agg tct cca ggc agt aga tcc tct tca aga tcc tgc      1888
Arg Ser Arg Ser Arg Ser Pro Gly Ser Arg Ser Ser Ser Arg Ser Cys
585                 590                 595                 600 tat tac tat gag tca agc cac tac aga cac cgc acg cac cga aat tct      1936
Tyr Tyr Tyr Glu Ser Ser His Tyr Arg His Arg Thr His Arg Asn Ser
                    605                 610                 615 ccc ttg tat gtg aga tca cgt tca aga tcg ccc tac agc cgt cgg ccc      1984
Pro Leu Tyr Val Arg Ser Arg Ser Arg Ser Pro Tyr Ser Arg Arg Pro
                620                 625                 630 agg tat gac agc tac gag gaa tat cag cac gag agg ctg aag agg gaa      2032
Arg Tyr Asp Ser Tyr Glu Glu Tyr Gln His Glu Arg Leu Lys Arg Glu
            635                 640                 645 gaa tat cgc aga gag tat gag aag cga gag tct gag agg gcc aag caa      2080
Glu Tyr Arg Arg Glu Tyr Glu Lys Arg Glu Ser Glu Arg Ala Lys Gln
        650                 655                 660 agg gag agg cag agg cag aag gca att gaa gag cgc cgt gtg att tat      2128
```

-continued

| | | | | | | | | | | | | | | | |
|---|---|---|---|---|---|---|---|---|---|---|---|---|---|---|---|
|Arg|Glu|Arg|Gln|Arg|Gln|Lys|Ala|Ile|Glu|Glu|Arg|Val|Ile|Tyr| |
|665| | | |670| | | |675| | | |680| | | | gtc ggt aaa atc aga cct gac aca aca cgg aca gaa ctg agg gac cgt    2176
Val Gly Lys Ile Arg Pro Asp Thr Thr Arg Thr Glu Leu Arg Asp Arg
                685                 690                 695 ttt gaa gtt ttt ggt gaa att gag gag tgc aca gta aat ctg cgg gat    2224
Phe Glu Val Phe Gly Glu Ile Glu Glu Cys Thr Val Asn Leu Arg Asp
            700                 705                 710 gat gga gac agc tat ggt ttc att acc tac cgt tat acc tgt gat gct    2272
Asp Gly Asp Ser Tyr Gly Phe Ile Thr Tyr Arg Tyr Thr Cys Asp Ala
        715                 720                 725 ttt gct gct ctt gaa aat gga tac act ttg cgc agg tca aac gaa act    2320
Phe Ala Ala Leu Glu Asn Gly Tyr Thr Leu Arg Arg Ser Asn Glu Thr
    730                 735                 740 gac ttt gag ctg tac ttt tgt gga cgc aag caa ttt ttc aag tct aac    2368
Asp Phe Glu Leu Tyr Phe Cys Gly Arg Lys Gln Phe Phe Lys Ser Asn
745                 750                 755                 760 tat gca gac cta gat tca aac tca gat gac ttt gac cct gct tcc acc    2416
Tyr Ala Asp Leu Asp Ser Asn Ser Asp Asp Phe Asp Pro Ala Ser Thr
                765                 770                 775 aag agc aag tat gac tct ctg gat ttt gat agt tta ctg aaa gaa gct    2464
Lys Ser Lys Tyr Asp Ser Leu Asp Phe Asp Ser Leu Leu Lys Glu Ala
            780                 785                 790 cag aga agc ttg cgc agg taacatgttc cctagctgag gatgacagag            2512
Gln Arg Ser Leu Arg Arg
        795 ggatggcgaa tacctcatgg gacagcgcgt ccttccctaa agactattgc aagtcatact    2572 taggaatttc tcctacttta cactctctgt acaaaaacaa aacaaaacaa caacaataca    2632 acaagaacaa caacaacaat aacaacaatg gtttacatga acacagctgc tgaagaggca    2692 agagacagaa tgatatccag taagcacatg tttattcatg ggtgtcagct ttgcttttcc    2752 tggagtctct tggtgatgga gtgtgcgtgt gtgcatgtat gtgtgtgtgt atgtatgtgt    2812 gtggtgtgtg tgcttggttt aggggaagta tgtgtgggta catgtgagga ctgggggcac    2872 ctgaccagaa tgcgcaaggg caaaccattt caaatggcag cagttccatg aagcacacct    2932 taaaacctag aacttcaaaa tgttcgtatt ctattcaaaa ggaaaaatat atatatatat    2992 atatatatat aaattaaaaa aaaaaaaaaa a                                   3023

<210> SEQ ID NO 5
<211> LENGTH: 798
<212> TYPE: PRT
<213> ORGANISM: Homo sapiens

<400> SEQUENCE: 5

Met Ala Trp Asp Met Cys Asn Gln Asp Ser Glu Ser Val Trp Ser Asp
 1               5                  10                  15

Ile Glu Cys Ala Ala Leu Val Gly Glu Asp Gln Pro Leu Cys Pro Asp
                20                  25                  30

Leu Pro Glu Leu Asp Leu Ser Glu Leu Asp Val Asn Asp Leu Asp Thr
            35                  40                  45

Asp Ser Phe Leu Gly Gly Leu Lys Trp Cys Ser Asp Gln Ser Glu Ile
        50                  55                  60

Ile Ser Asn Gln Tyr Asn Asn Glu Pro Ser Asn Ile Phe Glu Lys Ile
 65                 70                  75                  80

Asp Glu Glu Asn Glu Ala Asn Leu Leu Ala Val Leu Thr Glu Thr Leu
                85                  90                  95

-continued

```
Asp Ser Leu Pro Val Asp Glu Asp Gly Leu Pro Ser Phe Asp Ala Leu
            100                 105                 110
Thr Asp Gly Asp Val Thr Thr Asp Asn Glu Ala Ser Pro Ser Ser Met
        115                 120                 125
Pro Asp Gly Thr Pro Pro Gln Glu Ala Glu Pro Ser Leu Leu
    130                 135                 140
Lys Lys Leu Leu Leu Ala Pro Ala Asn Thr Gln Leu Ser Tyr Asn Glu
145                 150                 155                 160
Cys Ser Gly Leu Ser Thr Gln Asn His Ala Asn His Asn His Arg Ile
                165                 170                 175
Arg Thr Asn Pro Ala Ile Val Lys Thr Glu Asn Ser Trp Ser Asn Lys
            180                 185                 190
Ala Lys Ser Ile Cys Gln Gln Lys Pro Gln Arg Arg Pro Cys Ser
        195                 200                 205
Glu Leu Leu Lys Tyr Leu Thr Thr Asn Asp Asp Pro Pro His Thr Lys
    210                 215                 220
Pro Thr Glu Asn Arg Asn Ser Ser Arg Asp Lys Cys Thr Ser Lys Lys
225                 230                 235                 240
Lys Ser His Thr Gln Ser Gln Ser Gln His Leu Gln Ala Lys Pro Thr
                245                 250                 255
Thr Leu Ser Leu Pro Leu Thr Pro Glu Ser Pro Asn Asp Pro Lys Gly
            260                 265                 270
Ser Pro Phe Glu Asn Lys Thr Ile Glu Arg Thr Leu Ser Val Glu Leu
        275                 280                 285
Ser Gly Thr Ala Gly Leu Thr Pro Pro Thr Thr Pro Pro His Lys Ala
    290                 295                 300
Asn Gln Asp Asn Pro Phe Arg Ala Ser Pro Lys Leu Lys Ser Ser Cys
305                 310                 315                 320
Lys Thr Val Val Pro Pro Pro Ser Lys Lys Pro Arg Tyr Ser Glu Ser
                325                 330                 335
Ser Gly Thr Gln Gly Asn Asn Ser Thr Lys Lys Gly Pro Glu Gln Ser
            340                 345                 350
Glu Leu Tyr Ala Gln Leu Ser Lys Ser Ser Val Leu Thr Gly Gly His
        355                 360                 365
Glu Glu Arg Lys Thr Lys Arg Pro Ser Leu Arg Leu Phe Gly Asp His
    370                 375                 380
Asp Tyr Cys Gln Ser Ile Asn Ser Lys Thr Glu Ile Leu Ile Asn Ile
385                 390                 395                 400
Ser Gln Glu Leu Gln Asp Ser Arg Gln Leu Glu Asn Lys Asp Val Ser
                405                 410                 415
Ser Asp Trp Gln Gly Gln Ile Cys Ser Ser Thr Asp Ser Asp Gln Cys
            420                 425                 430
Tyr Leu Arg Glu Thr Leu Glu Ala Ser Lys Gln Val Ser Pro Cys Ser
        435                 440                 445
Thr Arg Lys Gln Leu Gln Asp Gln Glu Ile Arg Ala Glu Leu Asn Lys
    450                 455                 460
His Phe Gly His Pro Ser Gln Ala Val Phe Asp Glu Ala Asp Lys
465                 470                 475                 480
Thr Gly Glu Leu Arg Asp Ser Asp Phe Ser Asn Glu Gln Phe Ser Lys
                485                 490                 495
Leu Pro Met Phe Ile Asn Ser Gly Leu Ala Met Asp Gly Leu Phe Asp
            500                 505                 510
Asp Ser Glu Asp Lys Ser Asp Lys Leu Ser Tyr Pro Trp Asp Gly Thr
```

-continued

```
            515                 520                 525
Gln Ser Tyr Ser Leu Phe Asn Val Ser Pro Ser Cys Ser Phe Asn
        530                 535                 540
Ser Pro Cys Arg Asp Ser Val Ser Pro Pro Lys Ser Leu Phe Ser Gln
545                 550                 555                 560
Arg Pro Gln Arg Met Arg Ser Arg Ser Arg Ser Phe Ser Arg His Arg
                565                 570                 575
Ser Cys Ser Arg Ser Pro Tyr Ser Arg Ser Arg Ser Arg Ser Pro Gly
                580                 585                 590
Ser Arg Ser Ser Ser Arg Ser Cys Tyr Tyr Glu Ser Ser His Tyr
        595                 600                 605
Arg His Arg Thr His Arg Asn Ser Pro Leu Tyr Val Arg Ser Arg Ser
        610                 615                 620
Arg Ser Pro Tyr Ser Arg Arg Pro Arg Tyr Asp Ser Tyr Glu Glu Tyr
625                 630                 635                 640
Gln His Glu Arg Leu Lys Arg Glu Glu Tyr Arg Glu Tyr Glu Lys
                645                 650                 655
Arg Glu Ser Glu Arg Ala Lys Gln Arg Glu Arg Gln Arg Gln Lys Ala
                660                 665                 670
Ile Glu Glu Arg Arg Val Ile Tyr Val Gly Lys Ile Arg Pro Asp Thr
                675                 680                 685
Thr Arg Thr Glu Leu Arg Asp Arg Phe Glu Val Phe Gly Glu Ile Glu
        690                 695                 700
Glu Cys Thr Val Asn Leu Arg Asp Asp Gly Asp Ser Tyr Gly Phe Ile
705                 710                 715                 720
Thr Tyr Arg Tyr Thr Cys Asp Ala Phe Ala Ala Leu Glu Asn Gly Tyr
                725                 730                 735
Thr Leu Arg Arg Ser Asn Glu Thr Asp Phe Glu Leu Tyr Phe Cys Gly
                740                 745                 750
Arg Lys Gln Phe Phe Lys Ser Asn Tyr Ala Asp Leu Asp Ser Asn Ser
            755                 760                 765
Asp Asp Phe Asp Pro Ala Ser Thr Lys Ser Lys Tyr Asp Ser Leu Asp
770                 775                 780
Phe Asp Ser Leu Leu Lys Glu Ala Gln Arg Ser Leu Arg Arg
785                 790                 795
```